US 9,708,374 B2
Jul. 18, 2017

(12) United States Patent
Mechaly et al.

(10) Patent No.: US 9,708,374 B2
(45) Date of Patent: Jul. 18, 2017

(54) MODIFIED MICROBIAL TOXIN RECEPTOR FOR DELIVERING AGENTS INTO CELLS

(71) Applicant: President and Fellows of Harvard College, Cambridge, MA (US)

(72) Inventors: Adva Mechaly, Ness-Ziona (IL); Andrew J. McCluskey, Shrewsbury, MA (US); R. John Collier, Wellesley Hills, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 72 days.

(21) Appl. No.: 14/625,386

(22) Filed: Feb. 18, 2015

(65) Prior Publication Data

US 2016/0052976 A1  Feb. 25, 2016
US 2016/0362458 A9  Dec. 15, 2016

Related U.S. Application Data

(63) Continuation of application No. 14/380,423, filed as application No. PCT/US2013/027307 on Feb. 22, 2013, now abandoned.

(60) Provisional application No. 61/602,218, filed on Feb. 23, 2012.

(51) Int. Cl.
| | |
|---|---|
| A61K 39/02 | (2006.01) |
| A61K 39/07 | (2006.01) |
| A61K 39/00 | (2006.01) |
| C07K 14/32 | (2006.01) |
| C07K 16/32 | (2006.01) |
| C07K 14/21 | (2006.01) |
| C07K 14/25 | (2006.01) |
| C07K 14/28 | (2006.01) |
| C07K 14/33 | (2006.01) |
| C07K 14/34 | (2006.01) |
| C07K 16/28 | (2006.01) |
| C07K 16/40 | (2006.01) |

(52) U.S. Cl.
CPC ............ *C07K 14/32* (2013.01); *C07K 14/21* (2013.01); *C07K 14/25* (2013.01); *C07K 14/28* (2013.01); *C07K 14/33* (2013.01); *C07K 14/34* (2013.01); *C07K 16/2863* (2013.01); *C07K 16/32* (2013.01); *C07K 16/40* (2013.01); *C07K 2317/73* (2013.01); *C07K 2318/00* (2013.01); *C07K 2319/00* (2013.01); *C07K 2319/33* (2013.01); *C07K 2319/55* (2013.01); *C07K 2319/75* (2013.01)

(58) Field of Classification Search
CPC .......... A61K 39/00; A61K 39/02; A61K 39/07
USPC ...... 424/9.1, 9.2, 184.1, 192.1, 234.1, 236.1, 424/246.1
See application file for complete search history.

(56) References Cited

U.S. PATENT DOCUMENTS

| | | | |
|---|---|---|---|
| 5,591,631 A | * | 1/1997 | Leppla ............ A61K 47/48276 435/252.3 |
| 6,287,556 B1 | | 9/2001 | Portnoy et al. |
| 6,592,872 B1 | | 7/2003 | Klimpel et al. |
| 6,846,484 B2 | | 1/2005 | Vallera et al. |
| 6,916,917 B1 | | 7/2005 | Baltimore et al. |
| 2003/0124147 A1 | | 7/2003 | Vallera et al. |
| 2003/0202989 A1 | | 10/2003 | Collier et al. |
| 2009/0142794 A1 | | 6/2009 | Leppla et al. |
| 2010/0215575 A1 | | 8/2010 | O'Neill et al. |
| 2010/0311105 A1 | | 12/2010 | Lu et al. |

FOREIGN PATENT DOCUMENTS

| | | |
|---|---|---|
| CN | 1264861 A | 8/2000 |
| WO | 9418332 A2 | 8/1994 |
| WO | 0050872 A2 | 8/2000 |
| WO | 2008/011157 A2 | 1/2008 |
| WO | 2011/133704 A2 | 10/2011 |
| WO | 2012/096926 A2 | 7/2012 |

OTHER PUBLICATIONS

Bunt et al., Optical Fluorescence Microscopy, Springer-Verlag Berlin Heidelberg, 111-130 (2011). "Chapter 7: Site-Specific Labeling of Proteins in Living Cells using synthetic fluorescent dyes."
Sakamoto et al., Bioconjugate Chem., 21:2227-2233 (2010). "Enzyme-Mediated Site-Specific Antibody Protein modification using a ZZ domain as a linker."
Shapira et al., Toxins, 2:2519-2583 (2010). "Toxin-based therapeutic approaches".
Wu et al., Journal of Carbohydrate Chemistry, 31(1):48-66 (Epub. 2012). "Sortase-mediated transpeptidation for site-specific modification of peptides, glycopeptides and proteins."
Abrami et al., The Journal of Cell Biology, 166(5):645-651 (2004). "Membrane insertion of anthrax protective antigen and cytoplasmic delivery of lethal factor occur at different stages of the endocytic pathway."
Antos et al., J. Am. Chem. Soc.130(48):16338-43 (2008). "Lipid modification of proteins through sortase-catalyzed transpeptidation."
Antos et al., J. Am. Chem. Soc. 131(31):10800-1 (2009). "Site-specific N- and C-terminal labeling of a single polypeptide using sortases of different specificity."
Arteaga et al., Nat. Rev. Clin. Oncol. 9(1):16-32 (2012). "Treatment of HER2-positive breast cancer: current status and future perspectives."
Basilio et al., J. Gen. Physiol., 133(3):307-314 (2009). "Evidence for a Proton-Protein Symport Mechanism in the Anthrax Toxin Channel."

(Continued)

*Primary Examiner* — Rodney P Swartz
(74) *Attorney, Agent, or Firm* — Nixon Peabody LLP; David S. Resnick; Tari W. Mills

(57) ABSTRACT

We described a novel system of targeted cell therapy with a protein toxin, such as anthrax toxin, that has been modified to re-direct it to a desired cell target instead of its natural cell target. The system can be used for, e.g., targeted killing of undesired cells in a population of cells, such as cancer or overly active immune system cells.

14 Claims, 18 Drawing Sheets

(56) References Cited

OTHER PUBLICATIONS

Berchuck et al., Cancer Res.50(13): 4087-4091 (1990). "Overexpression of HER-2/neu is associated with poor survival in advanced epithelial ovarian cancer."

Bradley et al., Nature, 414:225-229 (2001). "Identification of the cellular receptor for anthrax toxin."

Cao et al., Cancer Res. 69(23): 8987-8995 (2009). Construction and characterization of novel, recombinant immunotoxins targeting the Her2/neu oncogene product: in vitro and in vivo studies.

Cao et al., Mol. Cancer Ther. 12,979-991 (2013). Construction and characterization of novel, completely human serine protease therapeutics targeting Her2/neu.

Carter et al., Proc Natl Acad Sci U S A 89:4285-9 (1992). "Humanization of an anti-p185HER2 antibody for human cancer therapy."

Chen et al., Proc Natl Acad Sci U S A, 108(28):11399-404 (2011). "A general strategy for the evolution of bond-forming enzymes using yeast display."

Collier, J. Mol. Bio, 25,83-98 (1967). "Effect of diphtheria toxin on protein synthesis: inactivation of one of the transfer factors."

Collier et al., Science. 164,1179-1181 (1969). Diphtheria toxin subunit active in vitro.

Collier et al., Mol. Aspect Med. 30, 413-422 (2009). "Membrane translocation by anthrax toxin."

Cunningham et al., Proc Natl Acad Sci U S A 99:7049-53 (2002). "Mapping the lethal factor and edema factor binding sites on oligomeric anthrax protective antigen."

Dawson et al., Science, 266:776-778 (1994). "Synthesis of Proteins by Native Chemical Ligation."

Duesbery et al., Science, 280:734-737 (1998). "Proteolytic Inactivation of MAP-Kinase-Kinase by Anthrax Lethal Factor."

Finkelstein, Phil. Trans. R. Soc. B, 364:209-215 (2009). "Proton-coupled protein transport through the anthrax toxin channel."

Gravalos et al., Ann. Oncol. 19, 1523-1529 (2008). "HER2 in gastric cancer: a new prognostic factor and a novel therapeutic target."

Guimaraes et al., J Cell Biol. 195, 751-764 (2011). "Identification of host cell factors required for intoxication through use of modified cholera toxin."

Llanogovan et al. Proc Natl Acad Sci U S A. 98:6056-61 (2001). "Structure of sortase, the transpeptidase that anchors proteins to the cell wall of *Staphylococcus aureus*."

Katayama et al., Nature Structural and Molecular Biology, 15(7):754-760 (2008). "GroEL as a molecular scaffold for structural analysis of the anthrax toxin pore."

Kintzer et al., J. Mol. Biol., 392:614-629 (2009). "The Protective Antigen Component of Anthrax Toxin Forms Functional Octameric Complexes."

Klimpel et al., Proc. Natl. Acad. Sci., 89:10277-10281 (1992). "Anthrax toxin protective antigen is activated by a cell surface protease with the sequence specificity and catalytic properties of furin."

Kobashigawa et al., J Biomol NMR 43:145-50 (2009). "Attachment of an NMR-invisible solubility enhancement tag using a sortase-mediated protein ligation method."

Krantz et al., Science, 309:777-781 (2005). "A Phenylalanine Clamp Catalyzes Protein Translocation Through the Anthrax Toxin Pore."

Krantz et al., J. Mol. Biol., 355:968-979 (2006). "Protein Translocation through the Anthrax Toxin Transmembrane Pore is Driven by a Proton Gradient."

Kruger et al., Biochemistry 43:1541-51 (2004). "Analysis of the substrate specificity of the *Staphylococcus aureus* sortase transpeptidase SrtA."

Leppla, Proc. Natl. Acad. Sci., 79:3162-3166 (1982). "Anthrax toxin edema factor: A bacterial adenylate cyclase that increases cyclic AMP concentrations in eukaryotic cells."

Leppla, et al, J. Appl. Microbiol. 87(2): 284 (1999). "Anthrax toxin fusion proteins for intracellular delivery of macromolecules."

Levary et al., PLoS One, 6(4): e18342 (2011). "Protein-protein fusion catalyzed by sortase A."

Liao et al., ChemBioChem. 15: 2458-2466 (2014). "Delivery of antibody mimics into mammalian cells via anthrax toxin protective antigen."

Ling et al., J Am Chem Soc 134: 10749-52 (2012). "Protein thioester synthesis enabled by sortase."

Mao et al., J Am Chem Soc. 126:2670-2671 (2004). "Sortase-mediated protein ligation: a new method for protein engineering."

Milne et al., The Journal of Biological Chemistry, 269(32):20607-20612 (1994). "Anthrax Protective Antigen Forms Oligomers during Intoxication of Mammalian Cells."

Mogridge et al., Proc Natl Acad Sci U S A, 99:7045-8 (2002). "The lethal and edema factors of anthrax toxin bind only to oligometric forms of the protective antigen."

Molloy et al., The Journal of Biological Chemistry, 267(23):16369-16402 (1992). "Human Furin Is a Calcium-dependent Serine Endoprotease That Recognizes the Sequence Arg-X-X-Arg and Efficiently Cleaves Anthrax Toxin Protective Antigen."

Orlova et al., Cancer Res 66:4339-48 (2006). "Tumor imaging using a picomolar affinity HER2 binding affibody molecule."

Pentelute et al., ACS Chemical Biology, 5(4):359-364 (2010). "A Semisynthesis Platform for Investigating Structure—Function Relationship in the N-Terminal Domain of the Anthrax Lethal Factor."

Pentelute et al., 50(10):2294-2296 (2011). "Chemical dissection of protein translocation through the anthrax toxin pore."

Popp et al., Nat Chem Biol, 3: 707-708 (2007). "Sortagging: a versatile method for protein labeling."

Pritz et al., J Org Chem, 72:3909-3912 (2007). "Synthesis of biologically active peptide nucleic acid-peptide conjugates by sortase-mediated ligation."

Rabideau et al., The Royal Society of Chemistry, DOI: 10.1039/c4sc02078b. "Delivery of mirror image polypeptides into cells." (First published online on Sep. 25, 2014).

Rosovitz et al., J. Biol. Chem. 278,30936-30944 (2003). "Alanine-scanning mutations in domain 4 of anthrax toxin protective antigen reveal residues important for binding to the cellular receptor and to a neutralizing monoclonal antibody."

Samantaray et al., J Am Chem Soc. 130: 2132-2133 (2008). "Peptide-sugar ligation catalyzed by transpeptidase sortase: a facile approach to neoglycoconjugate synthesis."

Schnolzer et al., Int. J. Peptide Protein Res., 40:180-193 (1992). "In situ neutralization in Box-chemistry solid phase peptide synthesis."

Scobie et al., PNAS, 100(9):5170-5174 (2003). "Human capillary morphogenesis protein 2 functions as an anthrax toxin receptor."

Sellman et al., The Journal of Biological Chemistry, 276(11):8371-8376 (2001). "Point Mutations in Anthrax Protective Antigen That Block Translocation."

Slamon et al., Science, 244,707-712 (1989). "Studies of the HER-2/neu proto-oncogene in human breast and ovarian cancer."

Ton-That et al., Proc Natl Acad Sci U S A 96:12424-9 (1999). "Purification and characterization of sortase, the transpeptidase that cleaves surface proteins of *Staphylococcus aureus* at the LPXTG motif."

Vitale et al., Biochemical and Biophysical Research Communications, 248:706-711 (1998). "Anthrax Lethal Factor Cleaves the N-Terminus of MAPKKs and Induces Tyrosine/Threonine Phosphorylation of MAPKs in Cultured Macrophages."

Venkataraman et al, PLOS Biology. 7(4): 0720-0729 (2009). "Reawakening Retrocyclins: Ancestral Human Defensins Active Against HIV-1."

Wesche et al, Biochemistry, 37(45): 15737-15746 (1998). "Characterization of membrane translocation by anthrax protective antigen."

Young et al., Annu. Rev. Biochem., 76:243-265 (2007). "Anthrax Toxin: Receptor Binding, Internalization, Pore Formation, and Translocation."

Zielinski et al., Clin. Cancer Res. 17(15): 5071-5081 (2001). "HER2-affitoxin: a potent therapeutic agent for the treatment of HER2-overexpressing tumors."

Zhang et al., PNAS, 101(48):16756-16761 (2004). "Evidence that translocation of anthrax toxin's lethal factor is initiated by entry of its N terminus into the protective antigen channel."

(56) References Cited

OTHER PUBLICATIONS

McCluskey et al., Molecular Oncology, 7(3):440-451 (2012). "Targeting HER2-positive cancer cells with receptor-redirected anthrax protective antigen."
Mechaly et al., mBio, 3(3):ppe00088-12 (2012). "Changing the receptor specificity of anthrax toxin."
Rogers et al., Cancer Research, 67(20):9980-9985 (2007). "Mutant anthrax toxin B moiety (protective antigen) inhibits angiogenesis and tumor growth."
Williams et al., Protein Engineering, 1(6):493-498 (1987). "Diphtheria toxin receptor binding domain substitution with interleukin-2: genetic construction and properties of a diphtheria toxin-related interluekin-2 fusion protein."
Kaiser et al., Infection and Immunity, 79(10:3913-3921 (2011). "Membrane Translocation of Binary Actin-ADP-Ribosylating Toxins from Clostridium difficile and Clostridiun perfringens is Facilitated by Cyclophilin A and Hsp90", Infection and Immunity, 79(10)3913-3921 (2011).
Liu et al., "Targeting of Tumor Cells by Cell Surface Urokinase Plasminogen Activator-Dependent Antrhax Toxin", The Journal of Biological Chemistry, 276(21):17976-17984 (2001).
Singh, et al., The Carboxyl-terminal End of Protective Antigen is Required for Receptor Binding and Antrhax Toxin Activity, The Journal of Biological Chemistry, 266(23):15493-15497 (1991).

\* cited by examiner

MODIFIED MICROBIAL TOXIN RECEPTOR FOR DELIVERING AGENTS INTO CELLS

CROSS-REFERENCE TO RELATED APPLICATIONS

This application is continuation of U.S. patent application Ser. No. 14/380,423 filed Aug. 22, 2014, now abandoned, which is a 35 U.S.C. §371 National Phase Entry Application of International Application No. PCT/US13/27307 filed Feb. 22, 2013, which designated the U.S., and claims benefit under 35 U.S.C. §119(e) of U.S. provisional Patent Application Ser. No. 61/602,218 filed on Feb. 23, 2012, the contents of which are incorporated herein by reference in their entirety.

GOVERNMENT SUPPORT

This invention was made with government support under AI 022021 awarded by National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Feb. 21, 2013, is named 002806-073301-PCT_SL.txt and is 17,750 bytes in size.

FIELD

The present invention relates to molecular genetics and molecular biology. More specifically, the present embodiments provide for compositions and methods for restructuring a binary bacterial toxin, such as anthrax toxin, to bind with a targeted cellular receptor, form a pore, and deliver proteinaceous molecules, such as cytotoxins, into the targeted cell.

BACKGROUND

An important goal for researchers and pharmaceutical companies is to identify ways to use proteinaceous delivery vehicles to introduce novel molecules into the cytosol of cells, particularly into mammalian cells. Although there are a number of methods for the delivery of bioactive peptides and proteins into mammalian cells for therapeutic and biotechnological purposes, there is still a specific need for methods to deliver larger molecules, such as proteins, enzymes or cytotoxins, that cannot traverse the plasma membrane by a simple diffusive process.

The current technologies used to gain therapeutic access to the cytosol are limited in that they require large quantities of sample, have limited selectivity, and tend to not escape the intracellular endosome. Hence, efficient delivery of the novel therapeutics remains a hurdle in drug development.

SUMMARY

We provide for a cell-specific, efficient delivery of bioactive molecules into cells. More specifically we have designed, binary "AB" toxins such that the B component binds to a heterologous, specific cell receptor on a target cell, and the A component interacts with the B component to deliver a biologically active molecule to the target cell cytosol via translocation through the cell membrane. For example, the receptor specificity of the transport protein of anthrax toxin, PA, can be altered as a means to deliver active toxin, such as anthrax toxin, to the cytosol of targeted cancer cells. Any cell, such as a cancer cell can be targeted so long as the cell expresses a specific marker or a marker that is significantly enriched in such cell. The present system is useful for both research purposes and medical applications calling for modification or eradication of selected populations of cells. For example, the systems and compositions described, can be used in reducing the number or eradicating cancer cells or reducing the number of over-reactive immune cells, e.g., in a human subject.

The present invention harnesses a major subclass of bacterial AB toxins, termed binary toxins, which use a transporter protein (B or binding unit or B-component) that actively translocates the catalytic portion of the toxin (A unit or A-component) into the cell. Although separate, the proteins having the A and B functions interact during the intoxication of cells. Examples of binary toxins include anthrax toxin, *Clostridium perfringens* Iota-toxin, *Clostridium botulinum* C2 toxin, and *Clostridium spiroforme* Iota-like toxin.

In the present embodiments, the native receptor-binding ligand of the B unit is typically ablated but not replaced, and the B unit fused with a ligand that binds specifically to a receptor on a target cell, e.g., a cancer cell or an immune cell. Thus, the B unit retains determinants needed for the cytoplasmic delivery of the A units, but specific cell targeting can be selected. The native A-component contains the catalytic activity, and translocates to the target cell cytosol via the B-component.

In the present embodiments, the A-component can also be altered, e.g., fused to a cytotoxin. Further cytotoxic domains of enzymatic protein toxins produced by bacteria, plants and animals, that can be harnessed using the delivery systems of the present embodiments include anthrax toxin, shiga toxin, shiga-like toxin 1 and 2, ricin, abrin, gelonin, pokeweed antiviral protein, saporin, trichsanthin, pepcin, maize RIP, alpha-sarcin, *Clostridium perfringens* epsilon toxin, *Botulinum* neurotoxins, *Staphylococcus* enterotoxins, *Clostridium difficile* toxins, pertussis toxins, or *pseudomonas* exotoxins.

A variety of specific cell receptors can be targeted using the compositions and methods of the present embodiments, as long as the receptor is one of those that internalize their ligands and traffic them to an acidic intracellular compartment, which facilitates proper folding of the translocated components. Receptors that can be targeted by the engineered binary toxins according to the present invention include, for example, HER1, HER2, HER3 and HER4 EGF receptors; vascular endothelial growth factor receptors VEGFR-1, VEGFR-2 and VEGFR-3; insulin-like growth factor 1 receptors; fibroblast growth factor receptors; thrombospondin 1 receptors; estrogen receptors; urokinase receptors; progesterone receptors; testosterone receptors; carcinoembryonic antigens; prostate-specific antigens; farnesoid X receptors; transforming growth factor receptors; transferrin receptors; hepatocyte growth factor receptors; or vasoactive intestinal polypeptide receptors 1 and 2.

Further delivery systems comprising altered binary or AB, pore-forming protein toxins can be selected from, for example, *Clostridium perfringens* toxins (alpha, beta, epsilon, iota); *Clostridium botulinum* C2 toxin; or *Clostridium spiroforme* Iota-like toxin.

For example, anthrax toxin is a member of the so-called binary toxins, a class in which the A and B functions inhabit separate proteins. Anthrax toxin uses a homopolymeric pore structure formed by the B moiety, protective antigen (PA), for the delivery of two alternative A moieties, edema factor (EF) and lethal factor (LF) into the cytoplasm. The receptor-targeted PA variants of the present embodiments can deliver a wide variety of therapeutic proteins, both nontoxic and toxic, to chosen class or classes of cells including the toxic native A-moieties (EF and LF). For example, the therapeutic protein is fused to the N-terminal portion of the lethal factor of anthrax toxin ($LF_N$), and undergoes unfolding during translocation through the PA variant to the target cell cytosol. Example toxins that can be fused to $LF_N$ for use according to the present embodiments include the catalytic domain of diphtheria toxin (DTA), the catalytic domain of shiga toxin, and the catalytic domain of *pseudomonas* exotoxin A. Some nontoxic proteins that can be fused to $LF_N$ for use according to the present embodiments include beta-lactamase, dihydrofolate reductase (DHFR), and ciliary neurotrophic factor.

BRIEF DESCRIPTION OF THE DRAWINGS

FIG. 2A shows Western blot analysis with anti-PA and anti-EGF antibodies, demonstrates the presence of both the PA and EGF proteins in the purified fusion protein. FIG. 2B shows Conversion of PA63 oligomers from the SDS-dissociable prepore state (black arrow) to the SDS-resistant pore state (arrow) at different pH values. Samples (5 µg) of native (83) and proteolytically-activated ($[63]_7$) forms of WT PA, mPA, and mPA-EGF were separated by SDS-PAGE and visualized by Coomassie blue staining.

FIG. 3A shows A431 or CHOK1 cells ($3.5 \times 10^4$) were incubated with 10 nM PA or PA variant mPA-EGF plus $LF_N$-DTA at the concentrations indicated. After a 4-hour (A431 cells) or overnight (CHOK1) incubation, the medium was replaced with medium containing 1 µCi of 3H-leucine/ml. Following a 1-hour incubation, incorporated $^3$H-leucine was determined by scintillation counting. FIG. 3B and FIG. 3C show assays were performed as described for panel 3A, but soluble EGF (500 nM) or PA-binding VWA domain of ANTRX2 (ANTRX2; 100 nM) was present during a 4 hour incubation with A431 cells (Panel B) or an overnight incubation period with CHOK1 cells (Panel C). Each point on the curves represents the average of three experiments.

FIG. 4A shows A431 cells ($1 \times 10^6$) were treated with 100 nM LF plus 10 nM PA or PA variant mPA-EGF for 3 hours. Cell lysates were prepared, fractionated by SDS-PAGE and transferred to PVDF membrane, and MEK1 cleavage was evaluated by Western blot with anti-MEK1 antibody. As a control, GAPDH was monitored with anti-GAPDH antibodies. FIG. 4B shows A431 cells ($3.5 \times 10^4$) were exposed to 50 nM EF plus 10 nM PA or PA variant mPA-EGF for 1 hour. A competition enzyme-linked immunoassay was performed to detect the intracellular concentration of cAMP, based on a standard curve, following the manufacturers protocol (Cell Signaling Technology). The column designated "Control" corresponds to A431 cells treated with EF in the absence of PA. Each bar represents the average of experiments performed in quadruplicate.

FIGS. 5A and 5B show the characterization of mPA-DTR. FIG. 5A shows Western blot analysis with anti-PA and anti-DTR antibodies demonstrating the presence of both PA and DTR in the purified mPA-DTR fusion. In FIG. 5B, CHOK1 cells ($3.5 \times 10^4$) were exposed overnight to a range of concentrations of $LF_N$-DTA in the presence of WT PA or mPA-DTR, in the presence or absence of excess soluble DTR. Protein synthesis was determined by $^3$H-leucine incorporation. Each point on the curve corresponds to the average of three experiments.

In FIG. 7 A, cells were incubated with a fixed concentration of mPA-ZHER2 (20 nM) plus various concentrations of $LF_N$-DTA for 4 h and then with medium containing [$^3$H]-leucine for 1 h. Protein synthesis was measured by scintillation counting and normalized against cells treated with mPA-ZHER2 alone. In FIG. 7B, HER2 receptor levels were determined by flow cytometry with a FITC-labeled anti-HER2 Affibody. Mean fluorescence intensity was calculated using the FloJo software package and plotted versus the log $EC_{50}$ for [$LF_N$-DTA]. In FIG. 7C, cells were exposed to the same conditions as FIG. 7A. After 48 h, cell viability was measured by XTT cytotoxicity assay and normalized against cells treated with mPA-ZHER2 alone. In FIG. 7D, apoptosis was assessed after exposing cells to either mPA-ZHER2 alone (minus sign "−"; open bars) or mPA-ZHER2 plus 10 nM $LF_N$-DTA (plus sign "+"; filled bars) for 24 h and measuring caspase 3/7 activation. Values corresponding to relative light units (RLU), generated by caspase 3/7 cleavage of a pre-luminescent substrate were extracted from dose-response curves. In all panels, cell lines with high, moderate, low, and no detectable HER2 receptor levels are indicated solid square, solid and open circle, solid triangle, and solid and open diamonds, respectively. Each point on the graphs represents the average of four experiments.

In FIG. 10A, the JIMT-1 tumor cell line was incubated with mPA-ZHER2 in combination with increasing amounts of $LF_N$-DTA (circle) or $LF_N$-RTA (square) for 4 h, and the effects on [$^3$H]-leucine incorporation were measured as described in FIG. 7. In FIG. 10B, FACS analysis using a FITC-conjugated HER2 Affibody confirms the expression of HER2 on the surface of JIMT-1 cells. The mean fluorescence was calculated using the FlowJo software package and plotted in the GRAPHPAD PRISM® software package (left panel) from the raw data presented in the histogram (right panel), which displays the shift in fluorescence (solid peak on the right of the histogram) compared to unstained cells (dashed peak on the left of the histogram). In FIG. 10C, JIMT-1 cells were exposed to the same conditions as FIG. 10A. After 48 or 72 h, cell viability was measured by XTT assay and plotted as percent cell viability normalized against control cells treated with mPA-ZHER2 alone. In FIG. 10D, Caspase 3/7 activation, an indicator of apoptosis, was measured after a 24 and 48 h exposure to 20 nM mPA-ZHER2 and $LF_N$-DTA, at the indicated concentrations. The cleavage of a pre-luminescent caspase 3/7 substrate generated RLU's that are plotted versus $LF_N$-DTA concentration. Control cells treated with mPA-ZHER2 alone are indicated with an X.

In FIG. 13A, cells were exposed to 20 nM mPA-EGF and $LF_N$-DTA at the concentrations indicated for 4 h and protein synthesis was measured as in experiments described above. Percent protein synthesis was normalized against cells treated with mPA-EGF alone. Cell lines expressing high amount of EGFR are MDA-MB-468, A431 and MDA-MB-231; low amount of EGFR is BT-474; and substantially no EGFR are SKBR-3 and CHO-K1. Each point on the curves represents the average of four experiments. In FIG. 13B, populations of fluorescent cells were mixed and exposed to a lethal dose of mPA-EGF and $LF_N$-DTA or mPA+LFN-DTA as a control; the control FACS data are identical to those in FIGS. 11A and 14A, as all of the experiments were conducted simultaneously. After 24 h, cells were washed with PBS and imaged with a fluorescence microscope or detached with trypsin and quantified by FACS (FIG. 13B). Each bar represents the average of experiments performed in triplicate. In FIG. 13C, a panel of cancer cell lines were plated in chambered slides overnight. The following day the chambers were removed and cells were exposed to the same treatments as described in Fig. B. Following intoxication for 4 h, cells were processed, and protein synthesis was quantified as described in FIG. 13A.

In FIGS. 14A (control) and 14B (cells exposed to the re-directed fusion toxin), various fluorescent cells were mixed in equal numbers and exposed to $LF_N$-DTA plus an equimolar mixture of mPA-ZHER2 and mPA-EGF. $LF_N$-DTA plus mPA was used as control (the control FACS data are identical to those in FIGS. 11A and 13C, as all of the experiments were conducted simultaneously). After 24 h, cell populations were detached with trypsin and quantified by FACS (FIGS. 14A and 14B) or washed with PBS and imaged with a fluorescence microscope (data not shown). Each bar represents the average of experiments performed in triplicate using SKBR3 (red), A431 (cyan), MDA-MB-468 (green), and CHO-K1 (unlabeled) cells. In FIG. 14B, a larger panel of cancer cell lines were plated in separate compartments of a chambered slide overnight. The following day, the partition was removed and cells were exposed to the same treatments as described above. Following intoxication for 4-hours, cells were incubated with medium supplemented with [3H]-leucine for 1-hour, and protein synthesis was quantified by scintillation counting. Percent protein synthesis was normalized against cells treated with mPA and LFN-DTA.

DETAILED DESCRIPTION

Figure 1:
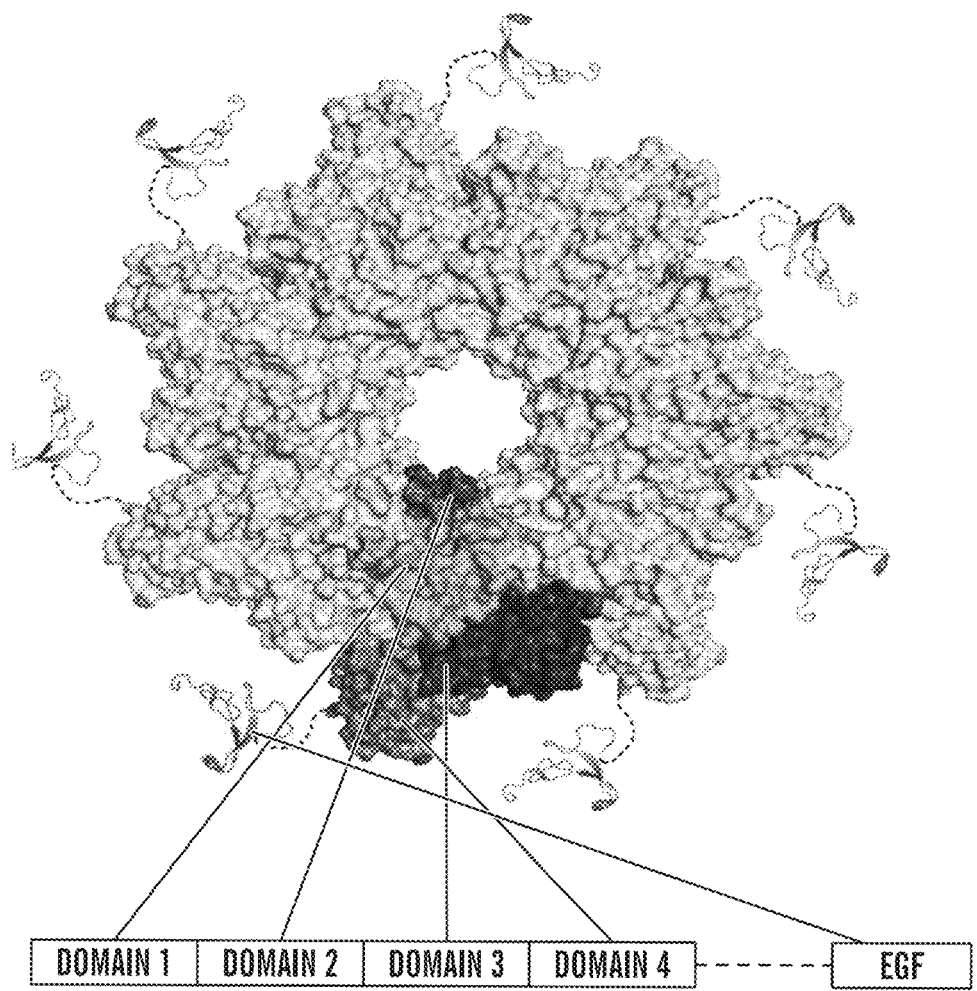
FIG. 1 shows a composite representation of the heptameric prepore formed by PA63 (PDB#1TZO) with EGF (PDB#1JL9) linked to the C terminus. Axial view, with domains 1, 2, 3, and 4 in a single subunit of PA63. Broken lines represent an 8 amino acid linker (SPGHKTQP) (SEQ ID NO:1) connecting the N terminus of EGF to the C terminus of PA63.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. The term "or" is inclusive unless modified, for example, by "either." Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Many pathogenic bacteria have evolved protein machinery that efficiently delivers potent enzymes to the cytosol of mammalian cells. Some infectious bacteria secrete protein toxins that reach the cytosolic compartment of host cells and disrupt homeostasis. A major class of bacterial toxins, termed AB toxins, use a receptor-binding domain (B or binding unit) that, in the case of some binary toxins, can actively translocate the catalytic portion of the toxin (A unit) into the cell. More specifically, the "A" component is usually the "active" portion, and the "B" component is usually the "binding" portion of the toxin. Thus, the A moiety or component contains the catalytic activity, while the B moiety or component possesses determinants needed for the cytoplasmic delivery of the A moieties into target cells. These delivery determinants include receptor binding activity, and often, but not always, membrane penetration activity, such the formation of a pore which translocates the A moiety. Examples of AB toxins include anthrax toxin, botulinum neurotoxin, diphtheria toxin, shiga toxin, shiga like toxin, exotoxin A, and cholera toxin. The A and B components of these and a variety of other toxins are well known. See, e.g., PCT US2012/20731. The nucleic acid sequences encoding these toxins and well as the amino acid sequences of these toxins are also known.

For example, anthrax toxin is one member of the so-called binary toxins, a class in which the A and B functions inhabit separate proteins. Although separate, the proteins having the A and B functions interact during the intoxication of cells. Anthrax toxin uses a single B moiety, protective antigen (PA; 83 kDa), for the delivery of two alternative A moieties, edema factor (EF; 89 kDa) and lethal factor (LF; 89 kDa) into the cytoplasm.

Bacterial toxin B components, in general, can be used to deliver bioactive moieties into the cytosol of the cells when the bioactive moiety is attached to the A component or a surrogate A component of the bacterial toxin, as long as the bioactive moiety unfolds correctly (if such is required for activity) during translocation. In addition to the anthrax B component, PA, the B components of *Clostridium perfringens* toxins (alpha, beta, epsilon, iota), *C. botulinum* C2 toxin, and *C. spiroforme* Iota-like toxins can be used in the systems, compositions and methods as described herein.

A bioactive peptide or cytotoxic domain can be attached to an A component of the binary system, such as the nontoxic PA-binding domain of LF ($LF_N$), and the fusion protein thus formed passes through the pore into the cytosol of a cell. See PCT US2012/20731. Cytotoxic domains can be derived from shiga toxin, shiga-like toxin 1 and 2, ricin, abrin, gelonin, pokeweed antiviral protein, saporin, trichsanthin, pepcin, maize RIP, alpha-sarcin, *Clostridium perfringens* epsiolon toxin, *Botulinum* neurotoxins, *Staphylococcus* enterotoxins, *difficile* toxins, pertussis toxins, or *pseudomonas* exotoxins.

The actions of the binary toxins depend on their ability to bind to one or more cell-surface receptors. Anthrax toxin acts by a sequence of events that begins when the Protective-Antigen (PA) moiety of the toxin binds to either of two cell-surface proteins, ANTXR1 and ANTXR2, and is proteolytically activated. The activated PA self-associates to form oligomeric pore precursors, which, in turn, bind the enzymatic moieties of the toxin and transport them to the cytosol. More specifically, the PA63 prepore binds up to three or four molecules of LF, forming complexes that are then endocytosed. Upon acidification of the endosome, protective antigen prepore undergoes a conformational rearrangement to form a membrane-spanning, ion-conductive pore, which transports lethal factor from the endosome to the cytosol. $LF_N$, the N-terminal domain of lethal factor, has nanomolar binding affinity for the pore, and this domain alone can be used for translocation of chemical moieties. Additionally, small positively charged peptide segments that mimic $LF_N$ can be used to aid in translocating these molecules through PA pore. These mimics may comprise at least one non-natural amino acid. See PCT US2012/20731. Engineered binary toxin B components, such as PA fusion proteins with altered receptor specificity, are useful in biological research and have practical applications, including perturbation or ablation of selected populations of cells in vivo.

An embodiment of the present invention provides for a genetically modified PA, carrying a double mutation into domain 4 of PA to ablate its native receptor-binding function and fused epidermal growth factor (EGF) to the C terminus of the mutated protein. The resulting fusion protein transported enzymatic effector proteins into a cell line that expressed the EGF receptor (A431 cells), but not into a line lacking this receptor (CHO-K1 cells). Addition of excess free EGF blocked transport of effector proteins into A431 cells via the fusion protein, but not via native PA. Additionally, fusing the diphtheria toxin receptor-binding domain to the C terminus of the mutated PA channeled effector-protein transport through the diphtheria toxin receptor.

Based on our examples, receptor binding domain of any of the AB toxins can be modified to ablate the native receptor binding domain and to fuse them with a desired receptor binding domain.

Accordingly, we provide a system or a composition comprising an altered binary toxin system for delivery of an active molecule to a target cell comprising: a fusion protein comprising a receptor-ablated pore-forming binary toxin unit fused to a non-toxin-associated receptor-binding ligand specific for a target cell, and a complementary toxin unit capable of associating with the pore-forming toxin unit for delivery of a therapeutic protein to the cytosol of the target cell.

Additional cell receptors that can be targeted and that are useful according to the present invention include HER1, HER2, HER3 and HER4 EGF receptors; vascular endothelial growth factor receptors VEGFR-1, VEGFR-2 and VEGFR-3; insulin-like growth factor 1 receptor; fibroblast growth factor receptors; thrombospondin 1 receptor; estrogen receptor; urokinase receptor; progesterone receptor; testosterone receptor; carcinoembryonic antigen; prostate-specific antigen; farnesoid X receptor; transforming growth factor receptors; transferring receptor; hepatocyte growth factor receptor; or vasoactive intestinal polypeptide receptor 1 and 2.

The targeting moieties can be, e.g., ligands, antibodies or Affibodies that specifically bind to any one of the receptors. Such ligands, antibodies and affibodies are either well known, or can be made using routine methods known to one of ordinary skill in the art.

Targeting of toxic proteins to specific classes of mammalian cells has been studied extensively, often with the goal of developing new treatments for malignancies. One approach to targeting involves replacing the receptor-binding domain of a toxin with a heterologous protein, such as a growth factor or antibody that binds to a specific cell-surface receptor.

Another approach is to link a heterologous protein to an altered form of the toxin in which the native receptor-binding function has been disrupted. Herein, the latter approach was used in the context of a binary toxin to redirect the receptor specificity of the transport moiety of anthrax toxin to heterologous receptors.

Accordingly, in some aspects of all the embodiments of the invention, the system or a composition comprising an altered binary toxin system for delivery of an active molecule to a target cell comprising: a fusion protein comprising a receptor-ablated pore-forming anthrax toxin unit fused to a non-anthrax-toxin-associated receptor-binding ligand specific for a target cell, and a complementary toxin unit capable of associating with the pore-forming toxin unit for delivery of a therapeutic protein to the cytosol of the target cell.

Anthrax toxin (ATx) is an ensemble of three large proteins: Protective Antigen (PA, 83 kDa), Lethal Factor (LF, 90 kDa), and Edema Factor (EF, 89 kDa). LF and EF are intracellular effector proteins: enzymes that modify substrates residing within the cytosolic compartment of mammalian cells. LF is a metalloprotease that cleaves most members of the MAP kinase family, and EF is a calmodulin- and Ca2+-dependent adenylyl cyclase, which elevates the level of cAMP within the cell. Leppla, 79 PNAS 3162 (1982); Duesbery et al., 280 Science 734 (1998); Vitale et al., 248 Biochem. Biophys. Res. Commn. 706 (1998). PA, the third component of the ensemble, is a receptor-binding transporter capable of forming pores in the endosomal membrane. Miller et al., 38 Biochem. 10432 (1999); Young & Collier, 76 Annu. Rev. Biochem. 243 (2007). These pores mediate the translocation of EF, LF, or various fusion proteins containing the N-terminal PA-binding domain of EF or LF, across the endosomal membrane to the cytosol. Collier, 30 Mol. Aspects Med. 413 (2009).

ATx action at the cellular level is initiated when PA binds to either of two receptors, ANTXR1 and ANTXR2, and is activated by a furin-class protease. Scobie, 100 PNAS 5170 (2003); Bradley et al., 414 Nature 225 (2001); Klimpel et al., 89 PNAS 10277 (1992). The cleavage yields a 20-kDa fragment, PA20, which is released into the surrounding medium, and a 63-kDa fragment, PA63, which remains bound to the receptor. Receptor-bound PA63 spontaneously self-associates to form ring-shaped heptameric and octameric oligomers (prepores), which are capable of binding LF and/or EF with nM affinity. Kintzer et al., 392 J. Mol. Biol. 614 (2009); Milne et al., 269 J. Biol. Chem. 20607 (1994); Mogridge et al., 99 PNAS 7045 (2002); Cunningham et al., 99 PNAS 7049 (2002). The resulting heterooligomeric complexes are endocytosed and delivered to the endosomal compartment, where acidic pH induces the prepores to undergo a major conformational rearrangement that allows them to form pores in the endosomal membrane. Young & Collier, 2007. These pores serve as protein translocases, which unfold bound LF and EF molecules and transport them across the endosomal membrane, where they refold and modify their respective intracellular targets.

The two known PA receptors, ANTXR1 (also called TEM8) and ANTXR2 (also called CMG2) are type 1 membrane proteins containing a von Willebrand/Integrin A (VWA) MIDAS domain. Within PA, both domain 4, the so-called receptor-binding domain, and domain 2, the pore-forming domain, participate in binding to the MIDAS domain of the receptors. Lacy et al., 101 PNAS 13147 (2004). ANTXR1 and ANTXR2 have differences in affinity for PA (Scobie et al., 2005; Wigelsworth, 279 J. Biol. Chem. 23349 (2004)), but both of these receptors bind PA in a manner that allows it to be activated and to oligomerize; and both receptors mediate trafficking of prepore:effector complexes to the endosomal compartment and translocation across the endosomal membrane.

In particular embodiments of the present invention, the receptor-binding activity of PA was ablated by mutating two residues of domain 4, and then fusing the C terminus of the mutated protein with heterologous receptor-binding proteins: human epidermal growth factor (EGF) (see FIG. 1), HER2 affibody (ZHER2), or the receptor-binding domain of diphtheria toxin (DTR). The resulting fusion proteins mediated the entry of effector enzymes, and entry was dependent on the cellular receptors for EGF, ZHER2, and DTR.

Figure 2A:
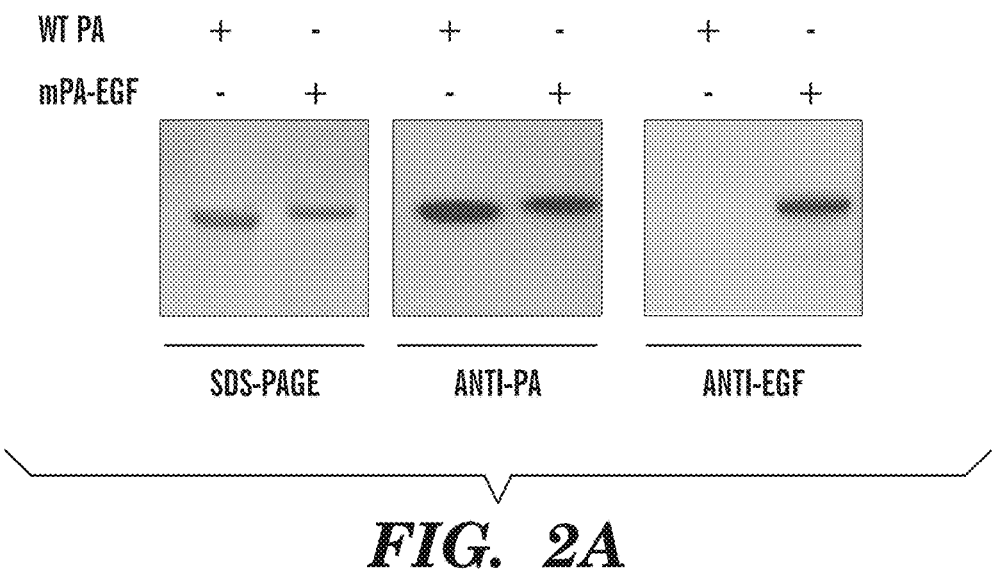
FIGS. 2A-2B show characterization of purified mPA-EGF.
Figure 2B:
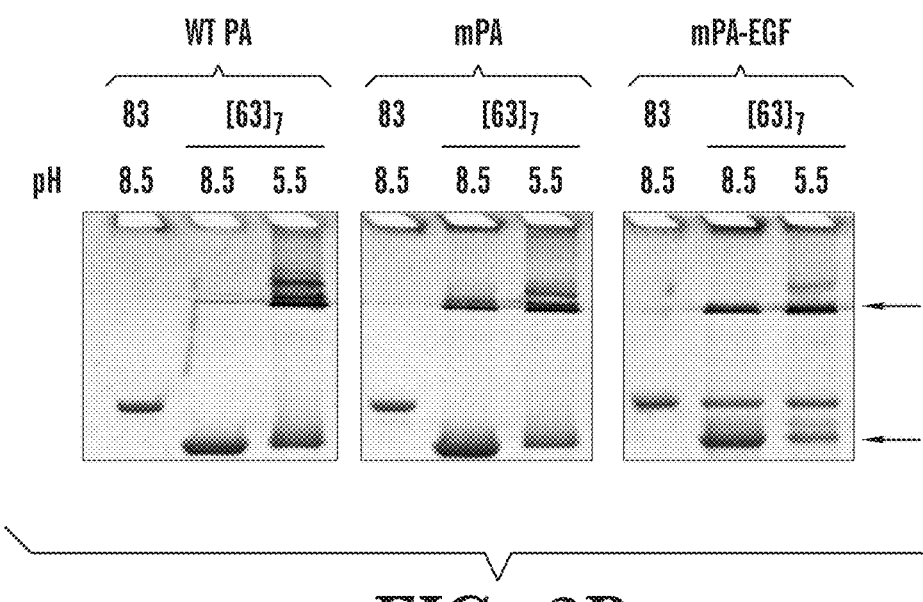

In one example, two mutations in the domain 4 of the PA, N682A and D683A, were introduced into PA to ablate its native receptor-binding function (Rosovitz et al., 278 J. Biol. Chem. 30936 (2003)), and the mutated protein (mPA) was expressed in *E. coli* BL21 (DE3). SEQ ID NO: 10 provides the amino acid reference sequence for these mutants. The purified product failed to promote entry of $LF_N$-DTA into either CHO-K1 cells or A431 cells at the highest concentration tested (10 nM), as measured by the inhibition of protein synthesis in the presence of $LF_N$-DTA. $LF_N$-DTA is a fusion between $LF_N$, the N-terminal PA63-binding domain of LF, and DTA, the catalytic domain of diphtheria toxin. See PCT US2012/20731. The DTA moiety catalyzes the ADP-ribosylation of eukaryotic elongation factor-2 (eEF-2) within the cytosol, blocking protein synthesis and causing cell death. Collier & Cole, 164 Science 1179 (1969); Collier, 25 J. Mol. Biol. 83 (1967). The proteolytically activated form of PA, mPA63, was able to form SDS-resistant, high molecular weight aggregates, characteristic of pores, although pH dependence of pore formation was somewhat altered (FIG. 2B).

Then, the PA N682A/D683A double mutant (mPA), with its virtually ablated the receptor-binding function, was fused to human EGF to the C-terminus of the mutated protein. Purified monomeric mPA-EGF was stable and ran slightly slower than native PA on SDS polyacrylamide gels, consistent with its higher molecular weight (FIG. 2A). Western blots showed that the product reacted with both anti-PA and anti-EGF antibodies. Also, it was also shown the mPA63-EGF fragment derived by trypsin treatment formed high molecular weight aggregates on SDS-PAGE similar to those seen with mPA63 (FIG. 2B). PA 63 refers to amino acids 197-764 of SEQ ID NO: 9.

Although the complete anthrax PA amino acid sequence well known, it is provided herein for reference. The sequence includes a 29 amino acid signal peptide marked with bold and italicized:

MKKRKVLIPL MALSTILVSS TGNLEVIQAE VKQENRLLNE SESSSQGLLG YYFSDLNFQA PMVVTSSTTG DLSIPSSELE NIPSENQYFQ SAIWSGFIKV KKSDEYTFAT SADNHVTMWV DDQEVINKAS NSNKIRLEKG RLYQIKIQYQ RENPTEKGLD FKLYWTDSQN KKEVISSDNL QLPELKQKSS NSRKKRSTSA GPTVPDRDND GIPDSLEVEG YTVDVKNKRT FLSPWISNIH EKKGLTKYKS SPEKWSTASD PYSDFEKVTG RIDKNVSPEA RHPLVAAYPI VHVDMENIIL SKNEDQSTQN TDSQTRTISK NTSTSRTHTS

EVHGNAEVHA SFFDIGGSVS AGFSNSNSST VAIDHSLSLA GERTWAETMG LNTADTARLN ANIRYVNTGT APIYNVLPTT SLVLGKNQTL ATIKAKENQL SQILAPNNYY PSKNLAPIAL NAQDDFSSTP ITMNYNQFLE LEKTKQLRLD TDQVYGNIAT YNFENGRVRV DTGSNWSEVL PQIQETTARI IFNGKDLNLV ERRIAAVNPS DPLETTKPDM TLKEALKIAF GFNEPNGNLQ YQGKDITEFD FNFDQQTSQN IKNQLAELNA TNIYTVLDKI KLNAKMNILI RDKRFHYDRN NIAVGADESV VKEAHREVIN SSTEGLLLNI DKDIRKILSG YIVEIEDTEG LKEVINDRYD MLNISSLRQD GKTFIDFKKY NDKLPLYISN PNYKVNVYAV TKENTIINPS ENGDTSTNGI KKILIFSKKG YEIG (SEQ ID NO: 9), Anthrax Protective antigen, with 29 aa signal peptide; UniProtKB NO. P13423 (PAG_BACAN)

The following shows the anthrax PA amino acid sequence without the 29 amino acid signal peptide. The numbering references to the mutants throughout this specification relate to the sequence without the signal peptide. In the following, the N682A/D683A mutant is indicated with bold:

(SEQ ID NO: 10)
E VKQENRLLNE SESSSQGLLG YYFSDLNFQA PMVVTSSTTG

DLSIPSSELE NIPSENQYFQ SAIWSGFIKV KKSDEYTFAT

SADNHVTMWV DDQEVINKAS NSNKIRLEKG RLYQIKIQYQ

RENPTEKGLD FKLYWTDSQN KKEVISSDNL QLPELKQKSS

NSRKKRSTSA GPTVPDRDND GIPDSLEVEG YTVDVKNKRT

FLSPWISNIH EKKGLTKYKS SPEKWSTASD PYSDFEKVTG

RIDKNVSPEA RHPLVAAYPI VHVDMENIIL SKNEDQSTQN

TDSQTRTISK NTSTSRTHTS EVHGNAEVHA SFFDIGGSVS

AGFSNSNSST VAIDHSLSLA GERTWAETMG LNTADTARLN

ANIRYVNTGT APIYNVLPTT SLVLGKNQTL ATIKAKENQL

SQILAPNNYY PSKNLAPIAL NAQDDFSSTP ITMNYNQFLE

LEKTKQLRLD TDQVYGNIAT YNFENGRVRV DTGSNWSEVL

PQIQETTARI IFNGKDLNLV ERRIAAVNPS DPLETTKPDM

TLKEALKIAF GFNEPNGNLQ YQGKDITEFD FNFDQQTSQN

IKNQLAELNA TNIYTVLDKI KLNAKMNILI RDKRFHYDRN

NIAVGADESV VKEAHREVIN SSTEGLLLNI DKDIRKILSG

YIVEIEDTEG LKEVINDRYD MLNISSLRQD GKTFIDFKKY

NDKLPLYISN PNYKVNVYAV TKENTIINPS ENGDTSTNGI

KKILIFSKKG YEIG.

Figure 3A:
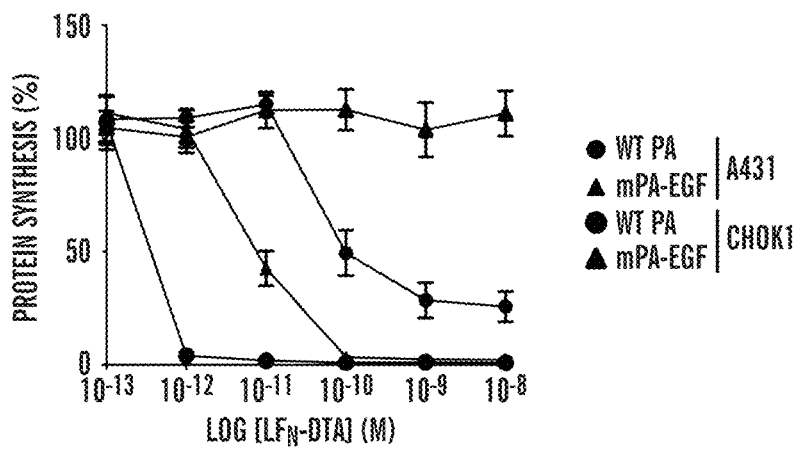
FIGS. 3A-3C reflect cytotoxicity assays demonstrating receptor-specific cell targeting of mPA-EGF.

A431 cells, which express high levels of the EGF receptor (Lin et al., 224 Science 843 (1984); Ullrich et al., 309 Nature 418 (1984)), were killed by $LF_N$-DTA (EC50~10 pM) in the presence of mPA-EGF, whereas CHO-K1 cells, which do not express the EGF receptor, were not killed (FIG. 3A). Wild-type PA also mediated the inhibition of protein synthesis in A431 cells, but a higher concentration of $LF_N$-DTA (EC50~100 pM) was needed, suggesting that these cells express a low level of ANTXR1, ANTXR2, or both. The translocation-deficient PA mutant, PAF427H (Krantz, 309 Science 777 (2005)), did not mediate killing on either A431 or CHO-K1 cells.

Figure 3B:
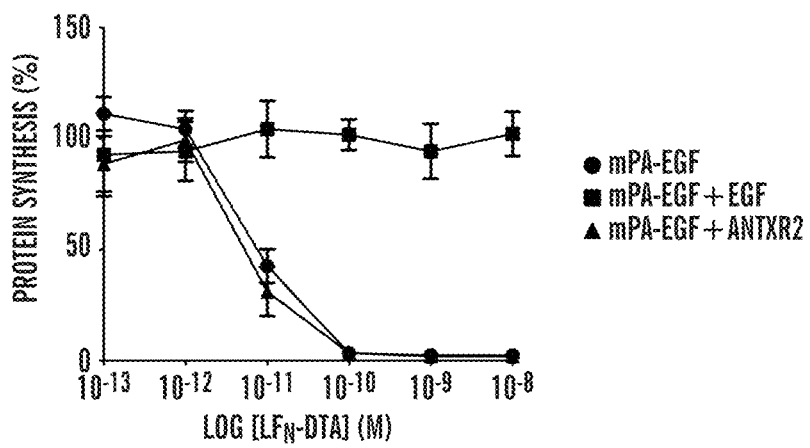
Figure 3C:
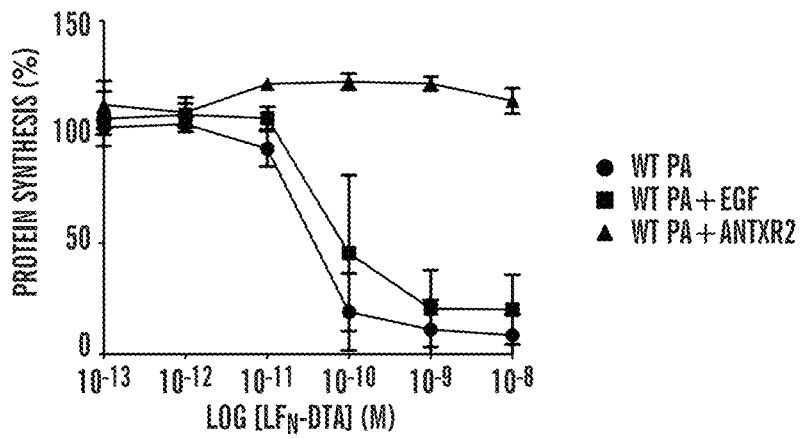

If the entry of $LF_N$-DTA into A431 cells mediated by mPA-EGF was dependent on binding to the EGF receptor, then addition of free EGF should compete for binding and block toxicity. As shown in FIG. 3B, a 50-fold excess of EGF completely protected the cells from the cytotoxic effects of $LF_N$-DTA, whereas the same concentration of the PA-binding VWA domain of ANTXR2 had no effect. In contrast, cytotoxicity mediated by wild-type PA on A431 cells was ablated by the ANTXR2 domain, but was not inhibited to a significant degree by EGF (FIG. 3C).

Figure 4A:
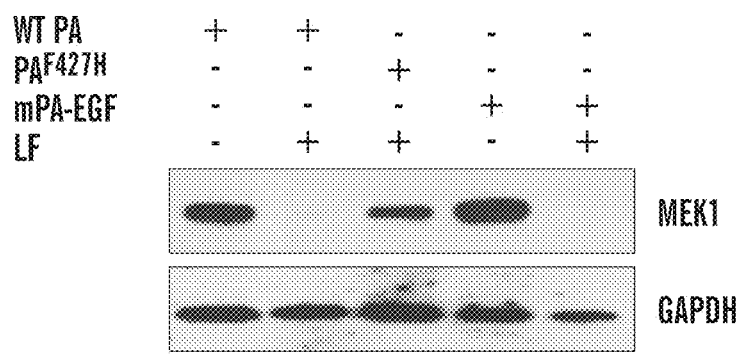
FIGS. 4A-4B demonstrates that mPA-EGF transports LF and EF into receptor-bearing cells.
Figure 4B:
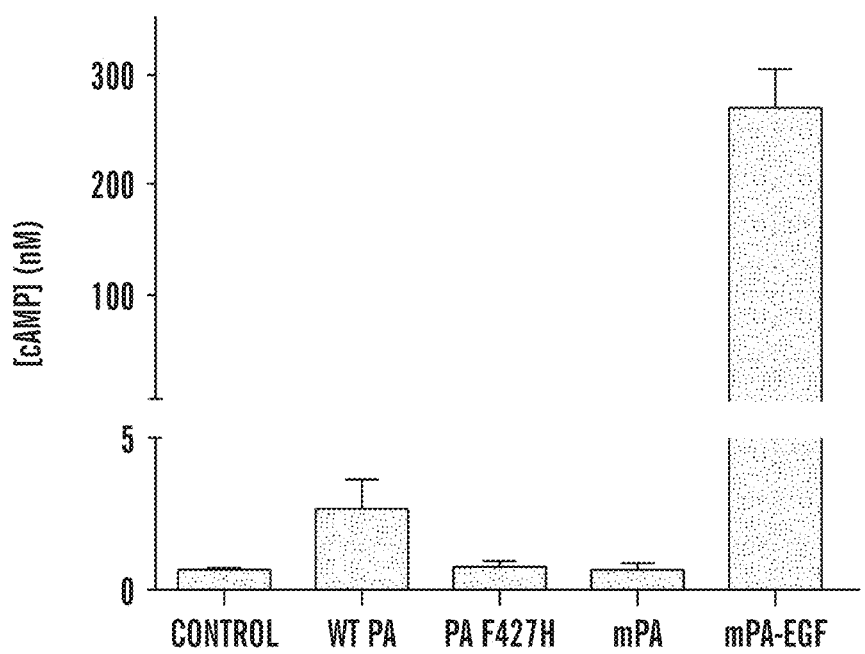

The ability the mPA-EGF to translocate LF and EF, the native effector moieties of anthrax toxin, into A431 cells was also demonstrated in an exemplary system. LF inactivates mitogen-activated protein kinase kinases (MEKs) by cleaving near their N-termini (Duesbery et al., 1998; Vitale et al., 1998), and LF entry was characterized by Western blotting of cell lysates with an anti-MEK1 antibody after incubating cells with LF plus PA or a variant thereof. MEK1 was cleaved completely with LF in combination with PA or mPA-EGF, but not in combination with the translocation-deficient mutant PA F427H (FIG. 4A). Entry of EF was measured using an enzyme-linked competition assay to determine the intracellular level of cyclic AMP (cAMP) and with mPA-EGF as the translocation vehicle observed a 400-fold elevation of cAMP (FIG. 4B). This level was ~100× higher than that with WT PA, and the level observed with mPA or PAF427H was at background. The strong elevation observed with mPA-EGF was likely due in part to the high level of EGFR on the A431 cells.

The following mutations in PA are known to reduce toxicity by reducing cell binding, and can thus be used alone or in combination to ablate PA receptor binding.

| MUTATION LOCATION IN SEQ ID NO: 9 | Effect on receptor binding |
| --- | --- |
| 686 | N → A: Decrease in cell binding. |
| 710 | Y → A: Decrease in cell binding. |
| 711 | N → A: Decrease in cell binding. |
| 712 | D → A: Decrease in cell binding. |
| 715 | P → A: Decrease in cell binding. |
| 716 | L → A: Decrease in cell binding. |
| 718 | I → A: Decrease in cell binding. |

In addition to $LF_N$, analogues of bacterial toxins such as diphtheria toxin and cholera toxin can be used to deliver the therapeutic proteins. Thus, in one embodiment, the invention provides a method of treating a subject by contacting cells of the subject either in vivo or ex vivo with a composition comprising a fusion molecule comprising the component A or a surrogate A component attached to the therapeutic moiety. See PCT US2012/20731.

Figures 5A, 5B:
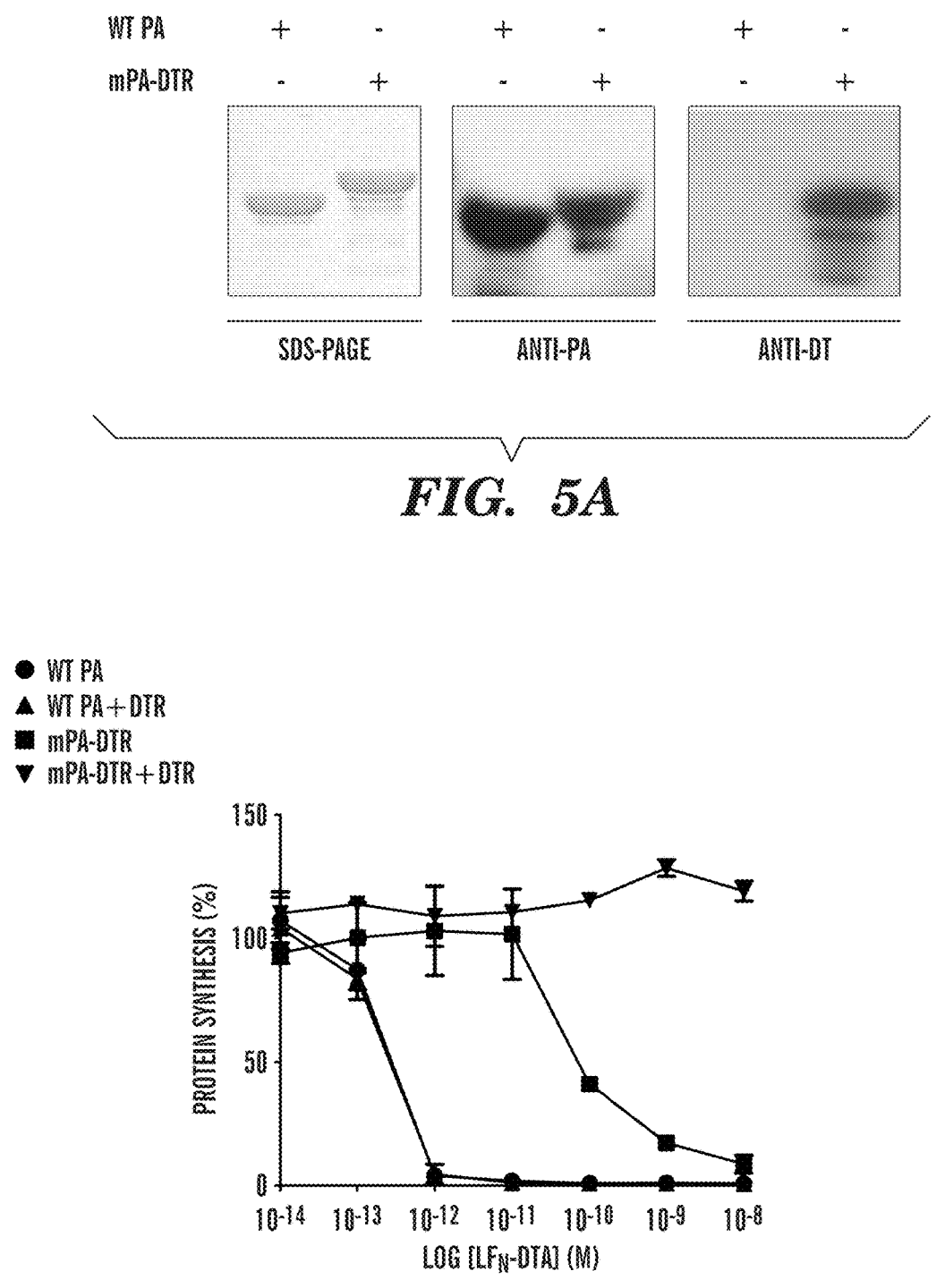

In another example, the 150-residue receptor-binding domain of diphtheria toxin (DTR) was fused to the C-terminus of mPA. The purified mPA-DTR fusion reacted with both anti-PA and anti-diphtheria toxin antibodies (FIG. 5) and retained the ability to oligomerize and form pores, and to bind and translocate cargo LFN-DTA in a planar bilayer system. The mPA-DTR variant delivered LFN-DTA into CHOK1 cells, inhibiting protein synthesis, and soluble DTR competitively blocked this inhibition (FIG. 5).

Figure 6:
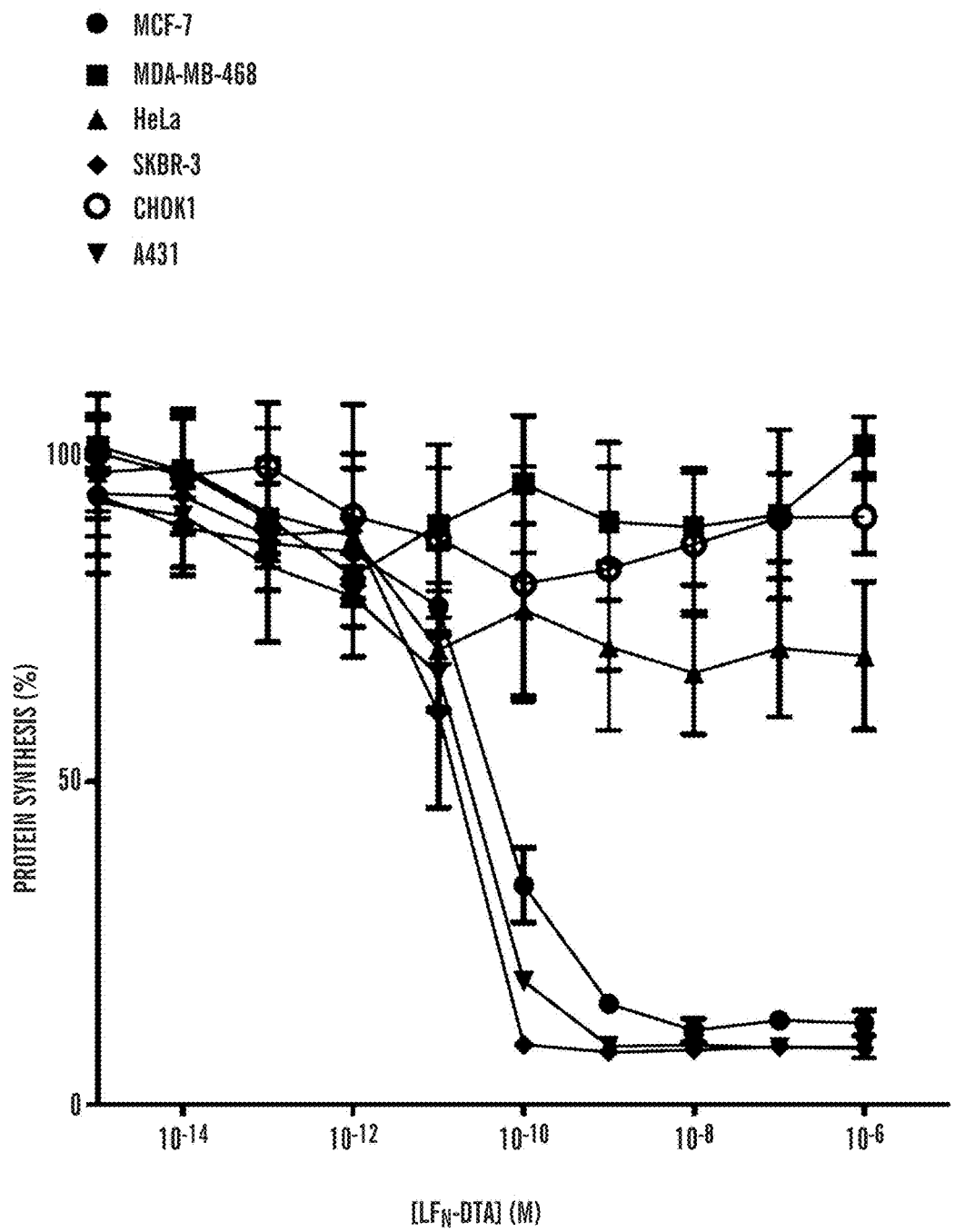
FIG. 6 presents data of cytotoxicity assays that confirm the receptor-specific targeting of mPA-ZHER2. HER2 receptor-positive (SKBR-3, A431, and MCF-7) and -negative (CHOK1, HeLA, and MDA-MB-468) cell lines ($3.5 \times 10^4$ cells) were exposed to a range of $LF_N$-DTA concentrations plus a constant concentration (20 nM) of the chimeric mPA-ZHER2 fusion protein. After a 4-hour incubation, the medium was replaced with medium containing 1 µCi of $^3$H-leucine/mL. Following a 1-hour incubation, the amount of radiolabeled leucine was determined by scintillation counting. Each point on the curves corresponds to the average of four experiments.

In yet another example, to specifically target HER2-positive cells, an Affibody (ZHER2; ~58 amino acids), known to bind the HER2 receptor with high affinity, was fused to the C-terminus of a receptor-recognition-deficient, mutated form of PA. Cell cytotoxicity assays using mPA-ZHER2 demonstrated that LFN-DTA inhibited protein synthesis in the cytosol of cells expressing the HER2 receptor, whereas HER-negative cells were unaffected (FIG. 6).

Because amplification of the HER2 gene or overexpression of HER2 occurs in 20% to 30% of early stage breast cancer patients, and because patients overexpressing the HER2 receptor have decreased overall survival, PA-based targeting of HER2 receptor-positive cells is an important example of cancer cells that can be targeted by the present strategy.

HER2 is a receptor tyrosine kinase belonging to the same family as EGFR. Unlike EGFR, however, HER2 has no known natural ligand. In the present study we developed a redirected binary toxin by fusing a high affinity Affibody specific for the HER2 receptor ($Z_{HER2:342}$) (Orlova et al. 2006) to the C terminus of receptor recognition-deficient PA (mPA), creating the fusion mPA-ZHER2. Affibodies represent a class of targeting polypeptides derived from the Z domain of *Staphylococcus aureus* protein A. Advantages over other receptor-targeting ligands derive from the fact that Affibodies are small (58 amino acids; ~6 kDa), pH- and thermo-stable, lack Cys residues, and fold independently and reversibly (Nord et al. 1997; Löfblom et al. 2010). Further, they may be rapidly evolved in vitro by phage-display technologies to affinity levels comparable to those observed with monoclonal antibodies.

Our results show that a receptor-recognition ablated B unit, such as mPA, with the HER2 targeting moiety, such as a $Z_{HER2:342}$ affibody fused to the C terminus of the receptor ablated B unit, can direct the action of either of two cytocidal effector proteins to HER2-positive tumor cells. These cells, including a HER2-positive trastuzumab-resistant tumor cell line, were ablated, and specific killing was observed regardless of whether the cultures consisted of a homogeneous population or had been mixed with cells lacking the HER2 marker. The amino acid sequence of the $Z_{HER2:342}$ affibody used in the examples is as follows:

```
                                    (SEQ ID NO: 11)
VDNKFNKEMRNAYWEIALLPNLNNQQKRAFIRSLYDDPSQSANLLAEAKK

LNDAQAPK.
```

Although the inventors used a specific AFFIBODY described in the examples to show proof of concept, in view of the results, any AFFIBODY or antibody that specifically binds to a cell surface protein of choice can be used.

In some aspects of all the embodiments of the invention, the cell non-toxin-associated receptor-binding ligand specific for a target cell comprises an antibody and/or an antigen-binding portion or fragment of an antibody.

An example antibody to target HER2 is trastuzumab, a recombinant monoclonal antibody used in therapeutics (HERCEPTIN). Another monoclonal antibody that targets HER2 positive cells and prevents dimerization of HER2 and HER3 is Pertuzumab (also called 2C4, trade name PERJETA). Either one of these antibodies can be used to fuse with the receptor ablated PA86 subunit, such as the mPA.

The term "antibody" refers to an immunoglobulin (e.g., IgG, IgM, IgA, IgE, IgD, etc.).

The basic functional unit of each antibody is an immunoglobulin (Ig) monomer (containing only one immunoglobulin ("Ig") unit). Included within this definition are monoclonal antibodies, chimeric antibodies, recombinant antibodies, and humanized antibodies.

In one embodiment, the invention's antibodies are monoclonal antibodies produced by hybridoma cells.

In particular, the invention contemplates antibody fragments that contain the idiotype ("antigen-binding fragment") of the antibody molecule. For example, such fragments include, but are not limited to, the Fab region, F(ab')2 fragment, pFc' fragment, and Fab' fragments.

The "Fab region" and "fragment, antigen binding region," interchangeably refer to portion of the antibody arms of the immunoglobulm "Y" that function in binding antigen. The Fab region is composed of one constant and one variable domain from each heavy and light chain of the antibody. Methods are known in the art for the construction of Fab expression libraries (Huse et al., Science, 246: 1275-1281 (1989)) to allow rapid and easy identification of monoclonal Fab fragments with the desired specificity. In another embodiment, Fc and Fab fragments can be generated by using the enzyme papain to cleave an immunoglobulin monomer into two Fab fragments and an Fc fragment. The enzyme pepsin cleaves below the hinge region, so a "F(ab')2 fragment" and a "pFc' fragment" is formed. The F(ab')2 fragment can be split into two "Fab' fragments" by mild reduction.

The invention also contemplates a "single-chain antibody" fragment, i.e., an amino acid sequence having at least one of the variable or complementarity determining regions (CDRs) of the whole antibody, and lacking some or all of the constant domains of the antibody. These constant domains are not necessary for antigen binding, but constitute a major portion of the structure of whole antibodies. Single-chain antibody fragments are smaller than whole antibodies and may therefore have greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely to provoke an immune response in a recipient than whole antibodies. Techniques for the production of single-chain antibodies are known (U.S. Pat. No. 4,946,778). The variable regions of the heavy and light chains can be fused together to form a "single-chain variable fragment" ("scFv fragment"), which is only half the size of the Fab fragment, yet retains the original specificity of the parent immunoglobulm.

The "Fc" and "Fragment, crystallizable" region interchangeably refer to portion of the base of the immunoglobulin "Y" that function in role in modulating immune cell activity. The Fc region is composed of two heavy chains that contribute two or three constant domains depending on the class of the antibody. By binding to specific proteins, the Fc region ensures that each antibody generates an appropriate immune response for a given antigen. The Fc region also binds to various cell receptors, such as Fc receptors, and other immune molecules, such as complement proteins. By doing this, it mediates different physiological effects including opsonization, cell lysis, and degranulation of mast cells, basophils and eosinophils. In an experimental setting, Fc and Fab fragments can be generated in the laboratory by cleaving an immunoglobulin monomer with the enzyme papain into two Fab fragments and an Fc fragment.

In some aspects of all the embodiment of the invention, the non-toxin-associated receptor-binding ligand specific for a target cell comprises an affibody.

"Affinity body," "Affibody®," and "affibody" molecules are antibody mimetic proteins that, like antibodies, can specifically bind target antigens (Nord, K., et al. (1997) Nature Biotechnol. 15: 772-777). Affibody molecules can be designed and used like aptamers. In one embodiment, Affibody molecules comprise a backbone derived from an IgG-binding domain of Staphylococcal Protein A (Protein A produced by *S. aureus*). The backbone can be derived from an IgG binding domain comprising the three alpha helices of the IgG-binding domain of Staphlococcal Protein A termed the B domain. The amino acid sequence of the B domain is described in Uhlen et al, J. Biol. Chem. 259: 1695-1702 (1984). Alternatively, the backbone can be derived from the three alpha helices of the synthetic IgG-binding domain known in the art as the Z domain, which is described in Nilsson et al., Protein Eng. 1: 107-113 (1987). The backbone of an affibody comprises the amino acid sequences of the IgG binding domain with amino acid substitutions at one or more amino acid positions. The affibody, for example, comprises the 58 amino acid sequence of the Z domain (VDNKFDKEXXXAXXEIXXLPNLNXXQXXAFIXS-LXDDPSQSADLLAEAKKLDD AQAPK, SEQ ID NO: 12), wherein X at each of positions 9, 10, 11, 13, 14, 17, 18, 24, 25, 27, 28, 32, and 35 is any amino acid (Capala et al, U.S. Pat. Appl. No. US20100254899).

The affibody molecule constitutes a highly suitable carrier for directing molecules of interest (e.g., toxins, radioisotopes, therapeutic peptides) to, e.g., tumor cells due to specific target binding and lack of irrelevant interactions, such as the Fc receptor binding displayed by some antibodies.

Common advantages of AFFIBODY® molecules over antibodies are better solubility, tissue penetration, stability towards heat and enzymes, and comparatively low production costs.

Affibodies are exemplified by, but not limited to, Anti-ErbB2 AFFIBODY® (also referred to as anti-HER2 AFFIBODY®), Anti-EGFR AFFIBODY®, Anti-TNF alpha AFFIBODY®, Anti-fibrinogen AFFIBODY®, Anti-transferrin AFFIBODY®, Anti-HSA AFFIBODY®, Anti-Insulin AFFIBODY®, Anti-IgG AFFIBODY®, Anti-IgM AFFIBODY®, Anti-IgA AFFIBODY®, and Anti-IgE AFFIBODY® (e.g., from Abcaem, Cambridge, Mass.).

Affibodies with an affinity of down to sub-nanomolar have been obtained from naive library selections, and affibodies with picomolar affinity have been obtained following affinity maturation (Orlova et al. (2006). "Tumor imaging using a picomolar affinity HER2 binding affibody molecule". Cancer Res. 66 (8): 4339-48. PMID 16618759). Affibodies conjugated to weak electrophiles bind their targets covalently (Holm et al., Electrophilic affibodies forming covalent bonds tp protein targets, J Biol Chem. 2009 Nov. 20; 284(47):32906-13. PMID 19759009).

Affibody molecules can be synthesized chemically or in bacteria or purchased from a commercial source (e.g., Affibody AB, Bromma, Sweden; Abeam, Cambridge, Mass.).

Affibody molecules can also be obtained by constructing a library of affibodies as described in U.S. Pat. No. 5,831,012, which is incorporated herein by reference. The affibody library can then be screened for affibodies which bind to target antigens of interest (e.g., HER-2, EGFR) by methods known in the art.

Affibody molecules are based on a three-helix bundle domain, which can be expressed in soluble and proteolytically stable forms in various host cells on its own or via fusion with other protein partners (Stahl et al. (1997). "The use of gene fusions to protein A and protein G in immunology and biotechnology". Pathol. Biol. (Paris) 45: 66-76. PMID 9097850. "

Affibodies tolerate modification and are independently folding when incorporated into fusion proteins. Head-to-tail fusions of Affibody molecules of the same specificity have proven to give avidity effects in target binding, and head-to-tail fusion of Affibody molecules of different specificities makes it possible to get bi-specific or multi-specific affinity proteins. Fusions with other proteins can also be created (Ronnmark et al. (2002) "Construction and characterization of affibody-Fc chimeras produced in *Escherichia coli*," J. Immunol. Methods 261: 199-211. PMID 11861078; Ronnmark et al. (2003) "Affibody-beta-galactosidase immunoconjugates produced as soluble fusion proteins in the *Escherichia coli* cytosol," J. Immunol. Methods 281: 149-160. PMID 14580889). A site for site-specific conjugation is facilitated by introduction of a single cysteine at a desired position.

A number of different Affibody molecules have been produced by chemical synthesis. Since they do not contain cysteines or disulfide bridges, they fold spontaneously and reversibly into the correct three-dimensional structures when the protection groups are removed after synthesis (Nord et al. (2001) "Recombinant human factor VIII-specific affinity ligands selected from phage-displayed combinatorial libraries of protein A," Eur. J. Biochem. 268: 1-10. PMID 11488921; Engfeldt et al. (2005) "Chemical synthesis of triple-labeled three-helix bundle binding proteins for specific fluorescent detection of unlabeled protein," Chem. BioChem. 6: 1043-1050. PMID 15880677).

We hypothesized that the ability of PA to transport two structurally disparate enzymes, LF and EF, into cells might suggest it is be capable of delivering heterologous proteins. Delivery of several such proteins and peptides has been demonstrated following their fusion to the PA63-binding domain of LF. Pentelute et al., 5 ACS Chem. Biol. 359 (2010); Pentelute et al., 2011; Arora & Leppla, 62 Infect. & Immun. 4955 (1994); Arora et al., 267 J. Biol. Chem. 15542 (1992); Hu & Leppla, 4 PLoS ONE 4 e7946 (2009a); Milne et al., 15 Molec. Microbiol. 661 (1995). A second mode of adaptability is illustrated by studies in which the furin activation site within PA was replaced with sites specific for other proteases for the purpose of tumor targeting. Liu et al., 60 Cancer Res. 6061 (2000); Abi-Habib et al., 5 Molec. Cancer Therap. 2556 (2006). The current study demonstrates that a third mode of adaptability, namely that the protein transport activity of PA, can be readily channeled through heterologous cell-surface receptors.

Given that the toxins have very specific receptors, it was not sure if the new target receptors would be able to allow pore formation and transport of the complexes to the cells. However, we showed that the exemplary mPA-EGF fusion construct was surprisingly able to transport LF, EF, and the $LF_N$-DTA fusion protein to the cytosol, suggesting that the essential oligomerization and transport functions of PA were not perturbed by channeling entry through surrogate receptors. One of the surrogate binding domains examined, DTR, performs an analogous function in an unrelated toxin (Louie et al., 1 Molec. Cell 67 (1997)), whereas the other, EGF, has no apparent relationship to bacterial toxin action. Both proteins bind to receptors that, like ANTXR1 and ANTXR2, internalize their ligands and traffic them to an acidic intracellular compartment. It is likely that entry into an acidic compartment is important for proper functioning of PA fusion proteins, because (a) acidic intravesicular pH plays a crucial role in promoting conversion of the PA prepore to the pore (Miller et al., 38 Biochem. 10432 (1999); Collier, 2009); and (b) the pH gradient across the endosomal membrane is essential for protein translocation (Krantz et al., 2006).

In view of the above, we can conclude that any novel receptor-targeting domain should function similarly when added to a receptor ablated PA83, for example, mPA as described herein. In some aspects of all the embodiments of the invention, the receptor-targeting domain is added to the C-terminus of the receptor-ablated PA83. Thus, in some aspects, the invention provides a composition comprising a fusion protein comprising a receptor-ablated pore-forming PA, such as mPA fused to a non-toxin-associated receptor-binding ligand specific for a target cell, wherein the non-toxin-associated receptor-binding ligand specific for a target cell is added to the C-terminus of the receptor-ablated PA. The composition may further comprise a complementary toxin unit capable of associating with the pore-forming toxin unit for delivery of a therapeutic protein to the cytosol of the target cell, such as LF or a fusion protein comprising the N-terminal PA-binding portion of the LF ($LF_N$).

The decision to fuse surrogate receptor ligands to the C terminus of mPA, instead of replacing domain 4 with these ligands, was based on results indicating that domain 4 stabilizes the prepore. Katayama et al., 107 PNAS 3453 (2010). Domain 4 must pivot away from domain 2 to allow the pore-forming loop to be relocated to the base of the structure, so that the transmembrane 0-barrel stem of the pore can be formed. Three-dimensional structure of the anthrax toxin pore inserted into lipid nanodiscs and lipid vesicles with the remainder of PA63 inhibit this pivoting and prevent premature conversion of the prepore to the pore (Katayama H, Wang J, Tama F, Chollet L, Gogol E P, Collier R J, Fisher M T. Interactions of domain 4, Proc Natl Acad Sci USA. 2010 Feb. 23; 107(8):3453-7). Thus, retaining domain 4 in mutated form allowed modification of receptor specificity while minimizing the likelihood that the process of prepore-to-pore conversion would be perturbed. That said, the double mutation used to ablate the receptor binding activity of domain 4 apparently slightly perturbed stability of the mPA63 prepore, as mPA prepore, unlike native prepore, underwent some degree of conversion to pore at pH 8.5 (FIG. 2A).

In addition to the recombinant technologies employed herein to fuse the receptor-specific ligand of the target cell to the B unit or create a cytotoxic A unit fusion, these constructs can also be produced by obtaining isolated components and conjugating them using chemical ligation or other conjugation techniques. See, e.g., Dawson et al., Synthesis of Proteins by Native Chemical Ligation, 266 Science 776 (1994); Muir et al., Expressed Protein Ligation: A General Method for Protein Engineering, 95 PNAS 6705 (1998); Nilsson et al., Chemical Synthesis of Proteins, 34 Ann. Rev. Biophys. Biomol. Struct. 91 (2005).

Redirecting PA-dependent protein transport through heterologous cellular receptors has applications both in experimental science and medicine. Leppla and coworkers have explored targeting of PA to tumor cells by changing the proteolytic activation site. Modified forms of PA were used to deliver FP59, a cytotoxic fusion protein similar to $LF_N$-DTA, to the cytosol of cells enriched in urokinase- or matrix metalloprotease. Abi-Habib et al., 5 Molec. Cancer Therap. 2556 (2006); Liu et al., 2000. Like these proteases, EGFR is also enriched on several tumors (Ciardiello & Tortora, 358 N. Engl. J. Med. 1160 (2008)). Thus mPA-EGF can also serve as an alternative means of targeting. Other ligands whose receptors are enriched on target cells, including cancer cells or virus-infected cells, would also be candidates for fusion to mPA or other B components of AB toxins.

Examples of other receptors that may be targeted for the treatment of cancer by fusing a receptor-binding moiety, e.g., an agonist, with the pore-forming portion of an AB toxin include estrogen receptors, e.g., in certain breast cancers, progesterone receptors, insulin-like growth factor, e.g., in certain prostate cancers.

Based on our examples, one can envision use of receptor-targeted PA variants to deliver a wide variety of proteins, nontoxic, as well as toxic, to chosen classes of cells. Fusion to LFN does not necessarily render all proteins transportable by PA, however. Like DTA, the catalytic domains of shiga toxin and *pseudomonas* exotoxin A, and some nontoxic proteins, including beta-lactamase, dihydrofolate reductase (DHFR), and ciliary neurotrophic factor, were found to be transported by PA when fused to LFN (Arora & Leppla, 1994; Arora et al., 1992; Hu & Leppla, 2009b; Wesche et al., 37 Biochem. 15737 (1998)); but LFN fusions of others, including tetanus toxin light chain, botulinum toxin E light chain, acidic fibroblast growth factor, basic fibroblast growth factor, and HIV Tat protein, were not transported. Introduction of an artificial disulfide into the DTA moiety of LFN-DTA blocked translocation, as did liganding of LFN-DTA and LFN-DHFR by adenine and methotrexate, respectively. Wesche et al., 1998. These findings are consistent with a requirement that proteins unfold in order to be translocated through the PA pore, and the propensity to unfold under acidic conditions may therefore be a major determinant of ability of a protein to be translocated. Nevertheless, analogues of bacterial toxins such as diphtheria toxin and cholera toxin, can be used to deliver other chemical entities or proteinaceous therapeutics.

Thus, in one embodiment, the invention provides a method of treating a subject by contacting cells of the subject either in vivo or ex vivo with a composition comprising a therapeutic intended to be delivered into the targeted cells of the subject with a fusion molecule comprising the component A or a surrogate A component attached to the therapeutic agent.

In some aspects of all the embodiments, the subject has cancer. In some aspects of all the embodiments, the subject has cancer wherein the cancer cells express HER2, and the toxin system delivered to the cancer patient comprises a fusion of protein as exemplified in Example 8, except that the targeting moiety can be changed to another HER2-specific affibody or an antibody specific to HER2.

Amplification or over-expression of the HER2 gene occurs in approximately 30% of breast cancers. It is strongly associated with increased disease recurrence and a worse prognosis (Roy V, Perez E A (November 2009). "Beyond trastuzumab: small molecule tyrosine kinase inhibitors in HER-2-positive breast cancer". Oncologist 14 (11): 1061-9). Over-expression is also known to occur in ovarian, stomach, and aggressive forms of uterine cancer, such as uterine serous endometrial carcinoma (Tan M, Yu D (2007). "Molecular mechanisms of HER2-mediated breast cancer chemoresistance". Adv. Exp. Med. Biol. 608: 119-29). Accordingly, the systems and methods described herein are useful in treatment of at least HER2 overexpressing breast cancer, ovarian cancer, stomach cancer, and aggressive forms of uterine cancer, such as uterine serous endometrial carcinoma. Uses of the altered binary toxin system for the treatment of these cancers are thus also provided.

The compositions, systems and uses of the present invention can be delivered in a pharmaceutically acceptable carrier. As used herein, the terms "pharmaceutically acceptable" refers to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation.

Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques.

The term "subject" as used herein and throughout the specification is intended to include organisms with eukaryotic cells, including mammals, such as humans and domestic animals, laboratory animal models, including rodent, canine, and primate models.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Some embodiments of the invention are listed in the following paragraphs:

1. An altered binary toxin system for delivery of an active molecule to a target cell comprising:
    a fusion protein comprising a receptor-ablated pore-forming binary or AB toxin unit fused to a non-toxin-associated receptor-binding ligand specific for a target cell, and
    a complementary toxin unit capable of associating with the pore-forming toxin unit for delivery of a therapeutic protein to the cytosol of the target cell.
2. The altered binary toxin system of paragraph 1, wherein the receptor-ablated pore-forming unit is anthrax toxin protective antigen (PA).
3. The altered binary toxin system of paragraph 2, wherein the PA is $PA^{N682A,D683A}$.
4. The altered binary toxin system of any one of paragraphs 1-3, wherein the non-toxin associated specific target receptor-binding ligand is an epidermal growth factor-1 or epidermal growth factor 2; or wherein the non-toxin associates specific receptor binding ligand targets epidermal growth factor receptor 1 (EGFR) or epidermal growth factor receptor 2 (HER2).
5. The altered binary toxin system of any one of paragraphs 1-4, wherein the complementary toxin unit is anthrax toxin lethal factor (LF or EF).
6. The altered binary toxin system of any one of paragraphs 1-5, wherein the complementary toxin unit the amino terminal portion of anthrax toxin lethal factor ($LF_N$ or $EF_N$).
7. The altered binary toxin system of any one of paragraphs 1-6, wherein the therapeutic protein is the catalytic domain of diphtheria toxin (DTA), ricin, shiga toxin, or *pseudomonas* exotoxin A.
8. The altered binary toxin system of any one of paragraphs 1-7, wherein the AB toxin is botulinum neurotoxin, anthrax toxin, diphtheria toxin, ricin, shiga toxin, shiga like toxin, exotoxin A, or cholera toxin.
9. The altered binary toxin system of paragraph 8, wherein the binary toxin is *Clostridium perfringens* toxins alpha, beta, epsilon or iota; *Clostridium botulinum* C2 toxin; or *Clostridium spiroforme* Iota-like toxin.
10. The altered binary toxin system of any one of paragraphs 1-9, wherein the receptor-binding ligand binds to a receptor selected from epidermal growth factor receptors HER1, HER2, HER3 or HER4; vascular endothelial growth factor receptors VEGFR-1, VEGFR-2 or VEGFR-3; insulin-like growth factor 1 receptor; fibroblast growth factor receptors; thrombospondin 1 receptor; estrogen receptors; urokinase receptors; progesterone receptors; testosterone receptors; carcinoembryonic antigens; prostate-specific antigens; farnesoid X receptors; transforming growth factor receptors; transferrin receptors; hepatocyte growth factor receptors; or vasoactive intestinal polypeptide receptors 1 and 2.
11. The altered binary toxin system of any one of paragraphs 1-10, wherein the receptor-binding ligand is selected from an antibody or an affibody.
12. The altered binary toxin system of paragraph 11, wherein the affibody is a HER2 affibody.
13. The altered binary toxin system of paragraph 12, wherein the HER2 affibody is ZHER2.
14. The altered binary toxin system of any one of paragraphs 1-13, wherein the therapeutic protein is the cytotoxic domain of shiga toxin, shiga-like toxin 1 and 2, ricin, ricin toxin A chain, abrin, gelonin, pokeweed antiviral protein, saporin, trichsanthin, pepcin, maize RIP, alpha-sarcin, *Clostridium perfringens* epsilon toxin, *Botulinum* neurotoxins, *Staphylococcus* enterotoxins, *Clostridium difficile* toxins, pertussis toxins, or *pseudomonas* exotoxin.
15. A kit for delivering bioactive molecules to a eukaryotic cell, comprising an altered binary toxin system of any one of paragraphs 1-14.
16. A method for treating cancer comprising administering to a subject diagnosed with cancer the altered binary toxin system of any one of the paragraphs 1-14.

17. The method of paragraph 16, wherein the altered binary toxin system comprises a receptor-redirected anthrax protective antigen.
18. The method of any one of paragraphs 16-17, wherein the cancer is a HER2 positive cancer and the anthrax protective antigen is fused with a HER2 binding ligand.
19. The method of paragraph 18, wherein the HER2 binding ligand is an antibody or an affibody.
20. Use of a binary toxin system of any one of the paragraphs 1-14 for the treatment of cancer.
21. Use of a receptor-redirected anthrax protective antigen for the treatment of cancer.
22. A pharmaceutical composition comprising the toxin system of any of the paragraphs 1-14 and a pharmaceutically acceptable carrier.

EXAMPLES

The following describes examples that were performed to show proof of concept of the general invention which outlines using a receptor-ablated pore forming subunit of AB toxins fused with a non-native (i.e., not the natural receptor for the toxin) receptor binding molecule to deliver toxic or non-toxic therapeutic drugs to a cell expressing the receptor. The specific examples can be expanded to more broadly encompass classes of toxins, ablation mutations, receptor binding domains and such with the knowledge in the art and the instructions provided herein.

Example 1

Generation of PA Expression Plasmids

One can construct the expression plasmids with any known sequences for the toxins according to routine methods and following, e.g., the principles used to make the below-described exemplary expression plasmid. In our examples we made the two PA chimeras used in this work: PAN682AD683A-EGF (mPA-EGF) and PAN682AD683A-DTR (mPA-DTR) were created by overlap extension PCR using a previously generated PAN682AD683A (mPA) gene coding sequence. In both cases the first PCR step consisted of two reactions (a) using a forward primer (PAFor—GATTTAGTAATTCGAATTCAAGTACGG) (SEQ ID NO:2), plus either PARevEGF (CATTCAGAGTCGCT-GTTTGGTTGCGTTTTATG) (SEQ ID NO:3), or PARevDTR (GTTTTATGCCCCGGAGATCCTATCT-CATAGCC) (SEQ ID NO:4) reverse primers, which contained the EGF and DTR overlapping regions, respectively; and (b) using forward and reverse primers to amplify the EGF (EGFFor—CATAAAACGCAACCAAACAGCGAC-TATGAATG) (SEQ ID NO:5) and (EGFRev—GGTGGT-GCTCGAGTCAACGGAGCTCCCACCATTTC) (SEQ ID NO:6) and DTR (DTRFor-GGCTATGAGATAGGATCTC-CGGGGCATAAAAC) (SEQ ID NO:7) and (DTRRev-GTGGTGGTGGTGGTGCTCGAGTCAGCTTTT-GATTTC) (SEQ ID NO:8) sequences. The PCR-generated DNA fragments were then subjected to a second PCR step using forward primer PAFor in combination with either the EGFRev or DTRRev primer, for PA-EGF and PA-DTR, to stitch and amplify the two fragments together. In both cases the full-length PCR products encoded EcoRI and XhoI restriction sites, in the forward and reverse primers, respectively. The PCR products were restriction digested and cloned into the pet22b expression vector following standard protocols. Each clone also coded for an 8-residue linker (SPGHKTQP, SEQ ID NO: 1) between PA and either EGF or DTR, which is part of the natural linker between the transmembrane and receptor-binding domains of diphtheria toxin.

Oligonucleotides were from Integrated DNA Technologies (Coralville, Iowa). Sigma-Aldrich (St. Louis, Mo.) supplied all chemicals unless noted otherwise. A synthetic human EGF gene, adjusted for *E. coli* expression, was a generous gift from Prof E. Joop van Zoelen (Department of Cell Biology and Applied Biology, Heijendaalseweg, Nijmegen). Soluble EGF was from ProSpec-Tany Technogene Ltd (East Brunswick, N.J.).

Example 2

Protein Expression and Purification

Recombinant wild-type PA (WT PA), PAF427H, mPA, mPA-EGF, and mPA-DTR were overexpressed in the periplasm of the BL21 (DE3) *E. coli* strain (Invitrogen, Carlsbad, Calif.). The resulting bacterial pellets were lysed and purified as described (Miller et al., 1999). Oligomeric prepores of WT PA and the various PA variants were produced by limited trypsin digestion at a final trypsin:PA ratio of 1:1000 (wt:wt) for 30 min at RT. The nicked proteins were subjected to anion-exchange chromatography, resulting in the separation of PA63 and PA20 fragments. PA63 spontaneously oligomerized to form porepore.

Purified mPA-EGF and mPA-DTR fusions were characterized by Western blot analysis. PA83 variants along with WT PA were subjected to SDS-PAGE and transferred to a polyvinylidene difluoride membrane (PVDF; Invitrogen, Carlsbad, Calif.). The membranes were blocked with Tris-buffered saline, pH 7.4; containing 2% BSA and hybridized with either mouse anti-PA (1:4000; cat. no. MAB8082; Millipore, Billerica, Mass.), rabbit anti-EGF (1:50000; cat. no. Ab9695; Abcam Cambridge, Mass.), or rabbit anti-DT antibodies (1:20000; cat. no. Ab53828; Abcam). Primary antibodies were detected with either goat anti-rabbit IgG (1:20000; Santa Cruz Biotechnology, Inc, Santa Cruz, Calif., cat. no. sc-2004) or rabbit anti-mouse IgG conjugated to HRP (1:10000; Santa Cruz, cat. no. sc-358914) with enhanced chemiluminescence (ECL) reagents (Pierce, Rockford, Ill.).

LF, EF, DTR, and $LF_N$-DTA were expressed in BL21 (DE3) *E. coli* (Invitrogen), under induction with 1 mM isopropyl β-D-1-thiogalactopyranoside (IPTG) for 4 hours, using the Champion pet-SUMO expression system (Invitrogen). Cell pellets were lysed by sonication in lysis buffer (20 mM Tris-HCl pH 8.0, 150 mM NaCl, 10 mM imidazole, 10 mg lysozyme, 2 mg DNAase I, supplemented with a complete Roche protease inhibitor tablet). Following sonication, the lysates were cleared by centrifugation and loaded onto a 3 ml bed volume of Ni-NTA agarose (Qiagen, Valencia, Calif.). The resin was washed with 15 column volumes of wash buffer (20 mM Tris-HCl pH 8.0, 150 mM NaCl, 20 mM imidazole) and eluted with the same buffer supplemented with 250 mM imidazole. The resulting purified protein was exchanged into 20 mM Tris-HCl, pH 8.0, 150 mM NaCl, and cleaved with SUMO protease (Invitrogen) overnight at 4° C. Uncleaved His-SUMO fusion and SUMO protease were removed by a second round of Ni-NTA chromatography, in which the flow-thru contained the cleaved product of interest.

Example 3

SDS Resistance

Exposure to acidic pH causes the structural transformation from PA prepore to pore, which is marked by the presence of SDS-resistant oligomers. WT PA, mPA, mPA-EGF, and mPA-DTR prepores (5 μg) were incubated in pH 5.5 buffer (100 mM KCl, 1 mM EDTA, and 10 mM each sodium oxalate, potassium phosphate, and MES, pH 5.5) or pH 8.5 buffer (20 mM Tris pH 8.5+150 nM NaCl) for 30 min at room temperature. Each sample was then exposed to SDS sample buffer and resolved by SDS-PAGE electrophoresis. Protein bands were visualized by Coomassie blue staining.

Example 4

Cell Culture

The CHO-K1 cell line was from the American Type Culture Collection (cat no. CCL-61, Manassas, Va.). Cells were maintained in Ham's F-12 medium supplemented with 10% fetal bovine serum (FBS), 500 units/ml penicillin G and 500 units/ml streptomycin sulfate (Life Technologies, Inc., Carlsbad, Calif.). The A431 cell line, also from the American Type Culture Collection (cat no. CCL-1555) was grown in Dulbecco's Modified Eagle's Medium, with 10% FBS, 500 units/ml penicillin G, 500 units/ml streptomycin sulfate, and 1 mM sodium pyruvate (American Type Culture Collection).

Example 5

Cytotoxicity Assays

Protein synthesis inhibition was used to measure the ability of WT PA and its derivatives to deliver LFN-DTA to the cytosol. CHO-K1 and A431 cells ($3.5 \times 10^4$ per well) were exposed to six 10-fold serial dilutions of LFN-DTA (starting with 10 nM) in combination with one of the PA83 variants (10 nM). Cells were either incubated for 4 hours (A431) or overnight (CHO-K1) at 37° C. Toxin containing medium was removed and the cells were incubated for 1 hr at 37° C. with leucine-deficient medium supplemented with 1 μCi of [3H]-leucine/ml (Perkin Elmer, Billerica, Mass.). The plates were washed twice with cold PBS and protein synthesis was measured by the amount of 3H-leucine protein, as determined by scintillation counting. Percent protein synthesis was plotted versus the log concentration of LFN-DTA where each bar represents the average of three experiments.

Competition experiments were performed as described above but with a 50-fold molar excess of soluble EGF (Prospec, East Brunswick, N.J.) or 10-fold excess of DTR to compete with mPA-EGF and mPA-DTR, respectively. Control experiments were also performed with a 10-fold excess of the PA-binding VWA domain of ANTRX2 (ANTHRX2), which was produced recombinantly as described (Scobie et al., 2005).

Example 6

MEK Cleavage

Translocation of LF to the cytosol of A431 cells was monitored by Western blot against cell lysates for mitogen-activated protein kinase kinase 1 (MEK1). A431 cells ($1 \times 10^6$ cells) were exposed to lethal toxin (10 nM PA83 variant and 100 nM LF) for 3 hr at 37° C. Cells were harvested in 100 μl of Tris-buffered saline (20 mM Tris-HCl, 150 mM NaCl pH 7.4), suspended in SDS-PAGE sample buffer and immediately incubated at 100° C. for 20 min. The lysates were resolved by SDS-PAGE and transferred to a PVDF membrane (Invitrogen). The membranes were blocked with Tris-buffered saline, pH 7.4, containing 2% BSA and hybridized with either anti-MEK1 (1:1000; Abcam, cat. No. Ab32071) or anti-GAPDH (1:2500; Abcam cat. No. Ab9485) antibodies. Primary antibodies were detected with goat anti-rabbit IgG conjugated to HRP (1:20000; Santa Cruz, cat. no. sc-2004) and ECL reagents (Pierce).

Example 7

Edema Factor Adenylate Cyclase Assay

A competition enzyme-linked immunoassay (Cell Signaling Technology, Danvers, Mass.) was used to determine the amount of cAMP generated in A431 cells upon exposure to EF. A431 cells ($3.5 \times 10^4$) were plated in a 96-well tissue culture plate and incubated with EF (50 nM) in the presence or absence of a PA variant (10 nM of WT PA, PAF427H, mPA, or mPA-EGF). After one hour the medium was removed and cells were washed twice with 200 μl of ice-cold PBS. Adherent cells were lysed with 100 μl 1× cell lysis buffer and incubated on ice for 10 min. Each cell lysis supernatant (50 μl) was combined with HRP-linked cAMP solution (50 μl), added to the cAMP assay plate, and incubated at room temperature for 3 hr. Wells were then washed four times with 200 μl of 1× wash buffer, and TMB substrate (100 μl) was added to each and let stand for 10 min. Following the addition of STOP solution (100 μl) the absorbance of each well was read at 450 nm and used to estimate cAMP based a standard curve. The amount of intracellular cAMP produced by EF+/−each PA variant was plotted as a histogram where each bar represents the average of four experiments.

Example 8

Targeting HER2-Positive Cancer Cells with Receptor Re-Directed Anthrax Protective Antigen We created a targeted toxin in which the receptor-binding and pore-forming moiety of anthrax toxin, termed Protective Antigen (PA), was modified to redirect its receptor specificity to HER2, a marker expressed at the surface of a significant fraction of breast and ovarian tumors. The resulting fusion protein (mPA-ZHER2) delivered cytocidal effectors specifically into HER2-positive tumor cells, including a trastuzumab-resistant line, causing death of the cells. No off-target killing of HER2-negative cells was observed, either with homogeneous populations or with mixtures of HER2-positive and HER2-negative cells. A mixture of mPA variants targeting different receptors mediated killing of cells bearing either receptor, without affecting cells devoid of these receptors. Anthrax toxin may serve as an effective platform for developing therapeutics to ablate cells bearing HER2 or other tumor-specific cell-surface markers.

Amplification and/or overexpression of the HER2 gene at the mRNA or protein level occurs in 20-25% of breast, gastric, and ovarian carcinomas (Berchuck et al. 1990; Gravalos & Jimeno 2008; Arteaga et al. 2012; Slamon et al. 1989). Particularly in breast cancer, increased expression of HER2 is associated with an aggressive form of the disease, which shows signs of increased tumor growth, recurrence, and resistance to therapy, all contributing to decreased patient survival (Arteaga et al. 2012). Although the FDA-approved monoclonal antibody, trastuzumab (trade name, HERCEPTIN®), is effective at slowing tumor growth, it remains ineffective at tumor elimination. New therapeutics that actively kill tumor cells thus remain a major goal of cancer-related research. A promising example of this strategy is to target the action of cytocidal protein toxins to specific cancer cells (Pastan et al. 2007).

We developed a straightforward way to redirect the receptor specificity of anthrax toxin (Mechaly et al. 2012). First we ablated the native receptor-binding activity of protective antigen (PA), the receptor-binding/pore-forming component of anthrax toxin, and then appended a heterologous, receptor-binding ligand to the C terminus of the mutated protein (mPA). Using this approach we created fusion proteins that direct toxin action specifically to two different receptors: the diphtheria toxin (DT) receptor (HB-EGF) and the epidermal growth factor receptor (EGFR) (Mechaly et al. 2012). In the current study we used this approach to redirect toxin action to cells bearing the HER2 receptor.

Anthrax toxin is an ensemble of three nontoxic, monomeric proteins (Young & Collier 2007). Two of them, the Lethal Factor and the Edema Factor (LF and EF), are enzymatic "effector proteins," which covalently modify molecular targets within the cytosol. LF is a metalloprotease, which inactivates most members of the mitogen-activated protein kinase kinase (MEK) family (Duesbery et al. 1998; Vitale et al. 1998), and EF is a calmodulin- and Ca2+-dependent adenylate cyclase, which increases the intracellular concentration of cyclic AMP (Leppla 1982). The third protein, PA, transports LF and EF from the extracellular milieu to the cytosol by a process that begins with its binding to specific cell-surface receptors and culminates in its forming pores in the endosomal membrane (Collier 2009).

After binding to either of its two known receptors—ANTXR1 (also called TEM8) and ANTXR2 (also called CMG2) (Scobie 2003; Bradley et al. 2001)—PA is proteolytically activated by a furin-family protease (Klimpel et al. 1992). The activated form self-assembles into heptameric (Milne et al. 1994) or octameric (Kintzer et al. 2009) ring-shaped oligomers (pore precursors, or "prepores"), which bind effector proteins with high (nM) affinity (Cunningham et al. 2002; Mogridge et al. 2002). The resulting complexes are endocytosed and delivered to the endosomal compartment, where the acidic pH causes a conformation change in the prepores that enables them to form pores in the endosomal membrane (Miller et al. 1999). The pores, in turn, actively unfold the bound effector proteins and transport them across the membrane to the cytosol (Young & Collier 2007). There they refold into active enzymes and modify their cytosolic substrates, causing major perturbations of cellular processes and, in some cases, cell death.

HER2 is a receptor tyrosine kinase belonging to the same family as EGFR. Unlike EGFR, however, HER2 has no known natural ligand. In the present study we developed a redirected binary toxin by fusing a high affinity Affibody specific for the HER2 receptor ($Z_{HER2:342}$) (Orlova et al. 2006) to the C terminus of receptor recognition-deficient PA (mPA), creating the fusion mPA-ZHER2. Affibodies represent a class of targeting polypeptides derived from the Z domain of Staphylococcus aureus protein A. Advantages over other receptor-targeting ligands derive from the fact that Affibodies are small (58 amino acids; ~6 kDa), pH- and thermo-stable, lack Cys residues, and fold independently and reversibly (Nord et al. 1997; Löfblom et al. 2010). Further, they may be rapidly evolved in vitro by phage-display technologies to affinity levels comparable to those observed with monoclonal antibodies.

Our results show that mPA with the $Z_{HER2:342}$ affibody fused to the C terminus can direct the action of either of two cytocidal effector proteins to HER2-positive tumor cells. These cells, including a HER2-positive trastuzumab-resistant tumor cell line, were ablated, and specific killing was observed regardless of whether the cultures consisted of a homogeneous population or had been mixed with cells lacking the HER2 marker.

Material and Methods
Reagents and Chemicals

Oligonucleotides and the $Z_{HER2:342}$ gene were synthesized by Integrated DNA Technologies (Coralville, Iowa). The $Z_{HER2:4}$ and $Z_{HER2:342}$ expression plasmids were kindly provided by Dr. Gregory Poon (Washington State University, Pullman, Wash.). All chemicals were purchased from Sigma-Aldrich (St. Louis, Mo.), unless noted otherwise.

Generation of LFN-RTA Expression Plasmid

The A chain of ricin (RTA) was fused to the C terminus of the N terminal PA-binding domain of LF ($LF_N$) by overlap extension PCR and cloned into the pet-SUMO expression vector (Invitrogen, Carlsbad, Calif.). The first PCR step consisted of two reactions (i) using a forward primer for $LF_N$ (LFNFOR—GCGGGCGGTCATGGTGAT-GTAGGT, SEQ ID NO: 13) and a reverse primer for $LF_N$ containing a GS spacer (in bold) and an overlap sequence for RTA (underlined)

($LF_N$-RTA$^{REV}$-

<u>AATTGGGTATTGTTTGGGGAATAT</u>ACTACCCCGTTGATCTTGAAGTTCTT

CCAA, SEQ ID NO: 14), and (ii) using a forward primer for RTA with a GS spacer (bold) and a 5' overlap region with LFN (underlined)

($LF_N$-RTA$^{FOR}$-

<u>TTGGAAGAACTTAAAGATCAACGG</u>GGTAGTATATTCCCCAAACAATACCC

AATT, SEQ ID NO: 15)

and a reverse primer for RTA encoding a double stop codon (in bold) (RTA$^{REV}$—CTATTA AAACTGTGACGATGGTG-GAGGTGC, SEQ ID NO: 16). A final PCR reaction using the two previous templates was performed with primers $LF_N^{FOR}$ and RTA$^{REV}$ to combine the two PCR products, which was subsequently ligated into the pet-SUMO expression vector (Invitrogen).

Protein Expression and Purification

Recombinant WT PA, mPA, mPA-ZHER2, and mPA-EGF were expressed and purified as described (Miller et al. 1999; Mechaly et al. 2012). Recombinant $LF_N$-DTA and $LF_N$-RTA were expressed as hexahistidine-SUMO fusions ("hexahistidine" disclosed as SEQ ID NO: 17) for 4 hours at 30° C. under the induction of 1 mM Isopropyl β-D-1-thiogalactopyranoside (IPTG) in the BL21 (DE3) Star strain of E. coli (Invitrogen). Cell pellets were suspended in 100 ml of lysis buffer (20 mM Tris-HCl pH 8.0, 150 mM NaCl, 10 mM imidazole, 10 mg lysozyme, 2 mg DNAse I, supplemented with a Roche complete protease inhibitor tablet per 50 ml) and lysed by sonication. Cell lysates were loaded onto a Ni2+-NTA agarose column, washed with 100 ml of wash buffer (20 mM Tris-HCl pH 8.0, 150 mM NaCl, and 20 mM imidazole), and eluted with wash buffer supplemented with 250 mM imidazole. The resulting purified protein was exchanged into 20 mM Tris-HCl pH 8.0 and 150 mM NaCl and cleaved with SUMO protease overnight at 4° C. to separate the LFN-DTA/RTA from the His6-SUMO protein ("His6" disclosed as SEQ ID NO: 17). Cleaved proteins were then subjected to a second Ni2+-NTA column to bind His6-SUMO ("His6" disclosed as SEQ ID NO: 17), leaving the protein of interest (LF$_N$-DTA/RTA) in the flow-thru fraction.

Affibodies ($Z_{HER2:4}$ and $Z_{HER2:342}$) were expressed from the pet15b expression vector (EMD Millipore, Billerica, Mass.) and purified in the same manner as LF$_N$-DTA, without the need for a cleavage step.

Cell Lines and Maintenance

The A431 (cat no. CCL-1555) and CHO-K1 (cat. no. CCL-61) cell lines were purchased from ATCC (Manassas, Va.). BT-474, MDA-MB-468, and SKBR3 cell lines were generously provided by Dr. Jean Zhao (Dana Farber Cancer Institute, Boston, Mass.). The MDA-MB-231 cell line was provided by Dr. Gregory Poon (Washington State University). The JIMT-1 cell line was purchased from AddexBio (cat. no. C0006005; San Diego, Calif.).

A431 and JIMT-1 cells were maintained in DMEM supplemented with 10% FCS, 500 units/ml penicillin G and 500 units/ml streptomycin sulfate (Invitrogen). CHO-K1 and all other cell lines were grown in Ham's F12 or RPMI medium (Invitrogen), respectively, supplemented with 10% FCS, 500 units/ml penicillin G and 500 units/nil streptomycin sulfate.

Stable cell lines expressing fluorescent proteins were produced by puromycin-selectable lentiviral particles coding for CFP, RFP, or GFP (GenTarget, San Diego, Calif.). Lentiviruses were transduced (MOI=1) into A431 (CFP), SKBR3 (RFP), and MDA-MB-468 (GFP) cell lines. At 48 hours post-transduction, the medium was replaced with medium containing 1 µg/ml puromycin to select for fluorescent cells that were puromycin resistant. Cells were passaged three more times in medium containing 1-5 µg/ml puromycin and analyzed by fluorescence-activated cell sorting (FACS) to ensure a homogenous, fluorescently-labeled population of cells were selected.

Quantifying Surface HER2 and EGF Receptor Levels

Cells ($1\times10^5$/experiment) were dissociated using a non-enzymatic reagent (Cellstripper™, Cellgro, Herndon, Va.) to eliminate the potential for receptor cleavage. Cells were re-suspended in either 200 µl of PBS or PBS with 1 µg/ml FITC-labeled anti-EGFR (cat. no. ab81872; Abcam, Cambridge, Mass.) or 2 µg/ml FITC-labeled anti-HER2 (cat. no. ab31891; Abcam) affibodies. Cells were incubated for 1-hour at 4° C., washed twice with 200 µl of PBS, and re-suspended in PBS. FACS was performed using a BD FACSCalibur flow cytometer. FACS histograms were analyzed using the FlowJo flow cytometry analysis software (Tree Star Inc., Ashland, Oreg.), while mean fluorescence intensity (MFI) was plotted using the GRAPHPAD PRISM® software package (GraphPad software Inc., La Jolla, Calif.). Each plot corresponds to three experiments where 50,000 events/condition were counted.

Cytotoxicity and Competition Assays 2.6.1 Protein synthesis inhibition—Cells were plated in appropriate medium at densities of $2.5\times10^4$ (BT-474) or $3.5\times10^4$ cells/well (all other cell lines) in 96 well plates and incubated overnight at 37° C. The following day, cells were exposed to ten 10-fold serial dilutions of LF$_N$-DTA or LF$_N$-RTA (starting with a final concentration of 1 µM) in medium supplemented with 20 nM mPA variant. After a 4-hour incubation, toxin-containing medium was removed and replaced with leucine-deficient medium supplemented with 1 µCi of [$^3$H]-leucine/ml (Perkin Elmer, Billerica, Mass.) and incubated for an additional hour. Plates were washed twice with cold PBS (200 µl) prior to the addition of 200 µl of scintillation fluid. The amount of [$^3$H]-leucine incorporated was determined by scintillation counting using a Wallac MicroBeta TriLux 1450 LSC (PerkinElmer, Waltham, Mass.). Percent protein synthesis was normalized against cells treated with the mPA variant alone and was plotted versus the concentration of LF$_N$-DTA or LF$_N$-RTA in GraphPad Prism, where each point on the curve corresponds to the average of four experiments.

Competition assays were performed as described above with increasing concentrations of free i) high-affinity ($Z_{HER2:342}$) or (ii) lower-affinity ($Z_{HER2:4}$) affibody added to medium containing 20 nM mPA-ZHER2 and LFN-DTA. MDA-MB-231 cells which express low levels of HER2 had to be challenged with a higher concentration of LF$_N$-DTA (1 µM), compared to all other cell lines (10 nM). Percent protein synthesis was normalized against cells treated with mPA-ZHER2 alone and plotted using GRAPHPAD PRISM, where each point on the curve corresponds to the average of four experiments.

Cell viability—Cell viability was measured by an XTT assay, following the manufacturers protocol (Biotium, Hayward, Calif.). Cells ($10^4$/well) were plated in the appropriate medium in 96 well optical bottom plates, incubated overnight at 37° C., and exposed to ten 10-fold serial dilutions of LF$_N$-DTA in medium supplemented with 20 nM mPA-ZHER2. After 48 or 72 h, 25 µl of XTT (sodium 2,3,-bis (2-methoxy-4-nitro-5-sulfophenyl)-5-[(phenylamino)-carbonyl]-2H-tetrazolium inner salt) reagent was added to each well, and the absorbance of reduced XTT was measured at 475 nm, using a SpectraMax M2e microplate reader (Molecular Devices, Sunnyvale, Calif.). Percent cell viability was normalized against cells treated with mPA-ZHER2 alone and plotted in GRAPHPAD PRISM, versus the concentration of LF$_N$-DTA. Each data point corresponds to the average of measurements performed in quadruplicate.

Apoptosis Assay

A cell-based apoptosis assay measuring the activation of known apoptotic markers, caspase 3/7, was performed according the supplier's protocol (Caspase-Glo 3/7 Assay; Promega, Madison, Wis.). Cells (104/well) were seeded in 96 well optical bottom plates and exposed to eight 10-fold serial dilutions of LFN-DTA in medium supplemented with 20 nM mPA-ZHER2. After 24 or 48 h, a proluminescent caspase 3/7 substrate was added to each well, followed by incubation at room temperature for 30 min. Luminescence resulting from substrate cleavage by caspase 3/7 was measured with a Wallac MicroBeta TriLux 1450 LSC (PerkinElmer). Relative luminescence was plotted versus the concentration of LF$_N$-DTA using GRAPHPAD PRISM, where each data point represents the average of four independent measurements.

Microscopy

Fluorescent cells were mixed ($2\times10^4$ cells each) as described above and grown on tissue culture treated coverslips overnight at 37° C. Coverslips were exposed to 10 nM LF$_N$-DTA and mPA, mPA-ZHER2, mPA-EGF, or mPA-ZHER2 and mPA-EGF (20 nM each). After 24 hours, cells were washed twice with PBS, fixed with 4% formaldehyde, and mounted on glass slides. Images were taken with a Nikon Eclipse TE2000-U fluorescence inverted microscope and analyzed using the MetaMorph software package (Molecular Devices, Sunnyvale, Calif.).

Co-Culture Cytotoxicity Assay (Protein Synthesis)

Fluorescence—Fluorescent cell lines (A431$^{CFP}$, MDA-MB-468$^{GFP}$, and SKBR3$^{RFP}$) were mixed equally ($10^5$ cells each) with unlabeled CHO-K1 cells, seeded into 6-well tissue culture dishes in RPMI medium, and incubated overnight at 37° C. The next day, cells were treated with 10 nM $LF_N$-DTA and either mPA, mPA-ZHER2, mPA-EGF, or mPA-ZHER2 and mPA-EGF (20 nM each). Cells were incubated an additional 24 hours, washed 2 times with PBS, and detached with trypsin. Cell populations were washed again in PBS and sorted based on fluorescence using a BD FACSCalibur flow cytometer (BD Biosciences, Sari Jose, Calif.). Each bar on the graphs corresponds to three experiments where at least 75,000 events were counted. FACS data was analyzed using the FlowJo analysis software and plotted using the GRAPHPAD PRISM® software package.

Protein synthesis—A panel of cancer cell lines and CHO-K1 cells were seeded ($3.5 \times 10^4$ cells/well) in partitioned sections of a chambered tissue culture slide. After an overnight incubation, the medium was removed, and the partitioning element was discarded. The slides were washed twice with PBS and incubated for 4 hours with RPMI containing 10 nM LFN-DTA with 20 nM of either (i) mPA, (ii) mPA-ZHER2, (iii) mPA-EGF, or (iv) a mixture of both mPA variants. Slides were removed from the toxin containing medium, washed with 15 ml of PBS, and incubated for an additional hour in leucine-deficient medium supplemented with 1 µCi of [$^3$H]-leucine/ml (Perkin Elmer). Slides were removed from the medium, washed with 30 ml of PBS, and dried. Individual cell populations were dissolved in 6 M Guanidine-HCl (75 µl) and added to scintillation fluid. The amount of [$^3$H]-leucine incorporated was determined by scintillation counting. The percent of protein synthesis was normalized against cells treated with mPA and $LF_N$-DTA and plotted using the GRAPHPAD PRISM software package.

Results mPA-ZHER2 Mediates the Killing of HER2 Positive Cells

We fused a high-affinity, 58-residue Affibody, $Z_{HER2:342}$, to the C terminus of mPA, a mutated, receptor-recognition-deficient form of PA. The resulting fusion protein (mPA-ZHER2) was tested in combination with the $LF_N$-DTA effector protein for ability to kill cancer cell lines displaying various levels of the HER2 receptor. Because LF and EF are not cytocidal for most cells, we used $LF_N$-DTA, a fusion of the N-terminal PA-binding domain of LF ($LF_N$) to the catalytic domain of diphtheria toxin (DTA), as intracellular effector. DTA ADP-ribosylates eukaryotic elongation factor 2 (eEF-2) in the cytosol, blocking protein synthesis and causing cell death (Collier & Cole 1969; Collier 1967; Honjo et al. 1968).

Figure 7A:
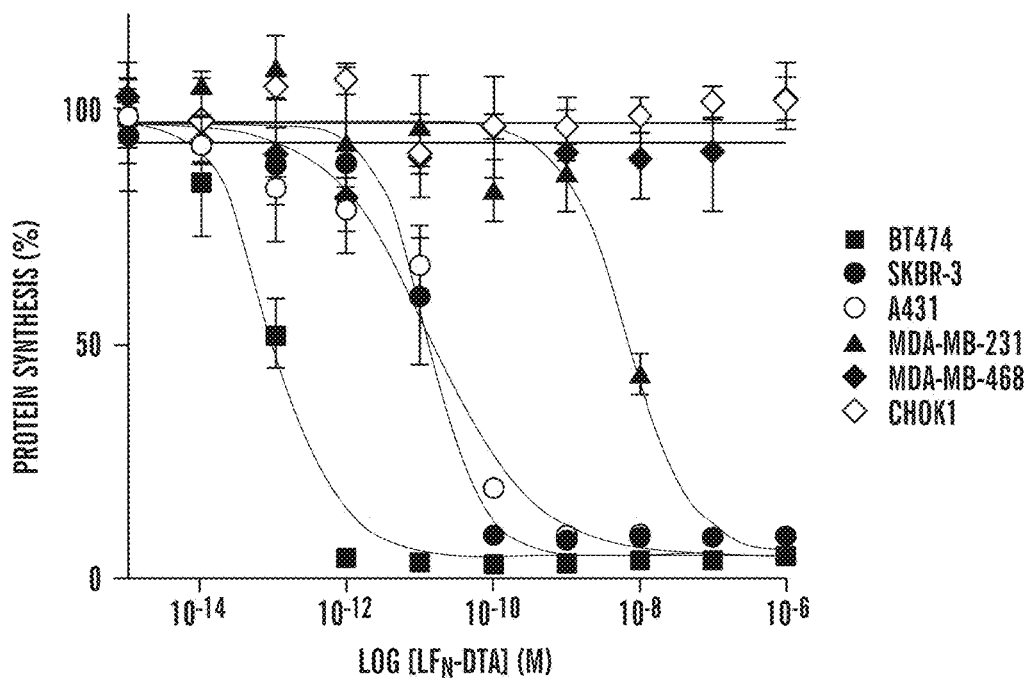
FIGS. 7A-7D show HER2-dependent killing of cell lines by mPA-ZHER2 plus $LF_N$-DTA.
Figure 7B:
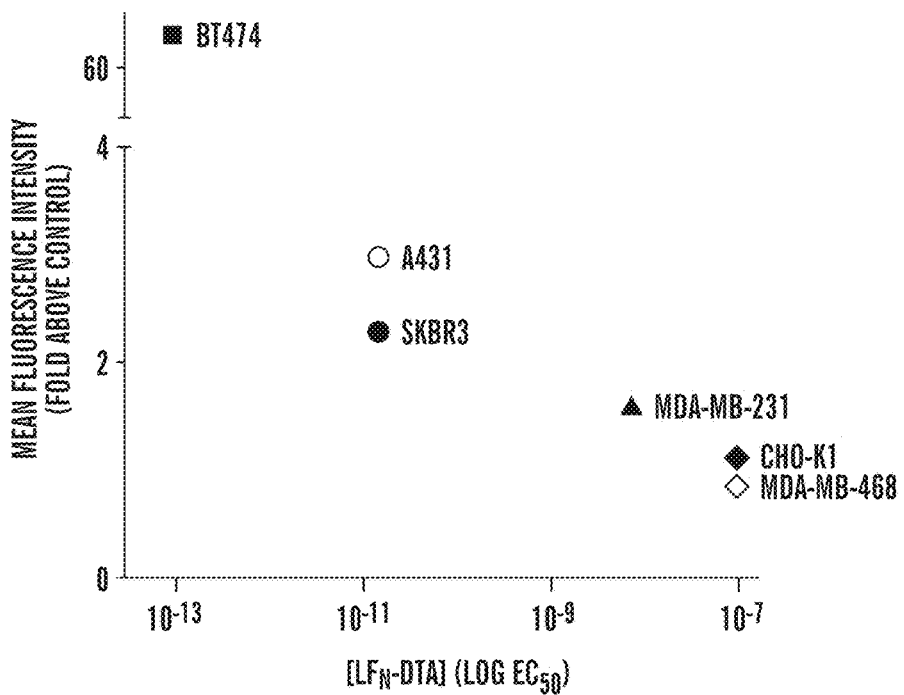

Various cell lines were incubated 4 h with a constant concentration of mPA-ZHER2 (20 nM) plus various concentrations of LFN-DTA, after which protein synthesis over a 1-h period was measured. The BT-474 cell line, which expressed the highest level of HER2 among the cell lines tested, was also the most sensitive; that is, it required the lowest concentration (EC50) of $LF_N$-DTA for 50% inhibition of protein synthesis (FIG. 7A). Two cell lines expressing moderate levels of HER2 (SKBR-3 and A431) showed intermediate levels of sensitivity; a line with a low level of HER2 (MDA-MB-231) showed low sensitivity ($EC_{50}$~10 nM); and two lines with no detectable HER2 (CHO-K1, MDA-MB-468) were unaffected, even at the highest concentrations of LFN-DTA tested. Thus, $EC_{50}$ was inversely related to the level of HER2 on the cell surface (FIG. 7B). Levels of HER2 on the various cell lines were determined by FACS analysis after incubation with a fluorescently labeled anti-HER2 Affibody.

Figure 7C:
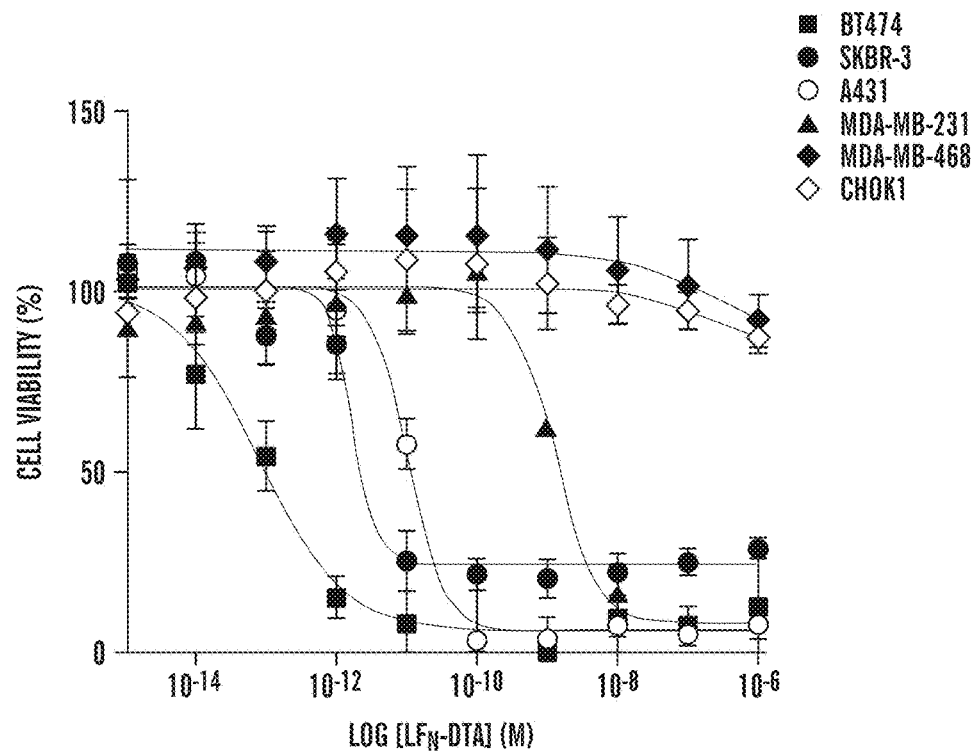
Figure 7D:
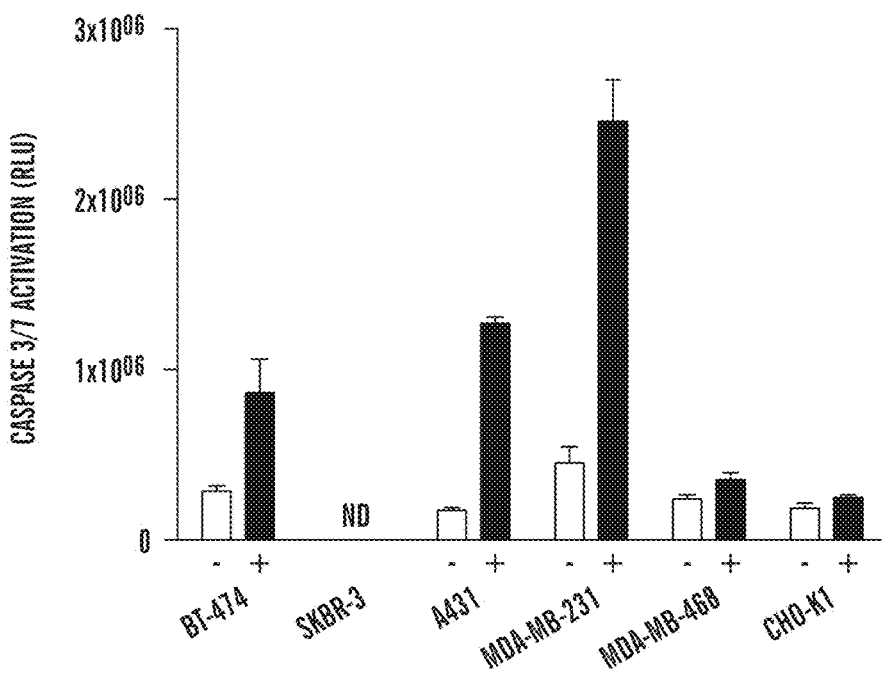

Cell viability confirmed that inhibition of protein synthesis by $LF_N$-DTA caused cell death. Cancer cell lines were exposed to mPA-ZHER2 (20 nM) and $LF_N$-DTA, at the indicated concentrations. After 48 h, cell viability was quantified by a cytotoxicity assay that quantifies the reduction of XTT reagent by mitochondrial enzymes that are active in live cells. Protein synthesis inhibition and cell death directly correlated (compare FIGS. 7A and 7C), with comparable EC50 values that reflect the amount of HER2 present on the cell surface (Table 1; FIG. 7B). Activation of known apoptotic markers, caspase 3/7, confirmed that cell death resulted from apoptosis (FIG. 7D). Caspase 3/7 activation did not increase after 24 h (data not shown) and was dose-dependent; cells expressing higher amounts of HER2 receptor showed caspase 3/7 activation at a lower $LF_N$-DTA concentration. The level of caspase 3/7 activation differed among various cell types and could not be confirmed for the SKBR3 cell line.

Figure 8A:
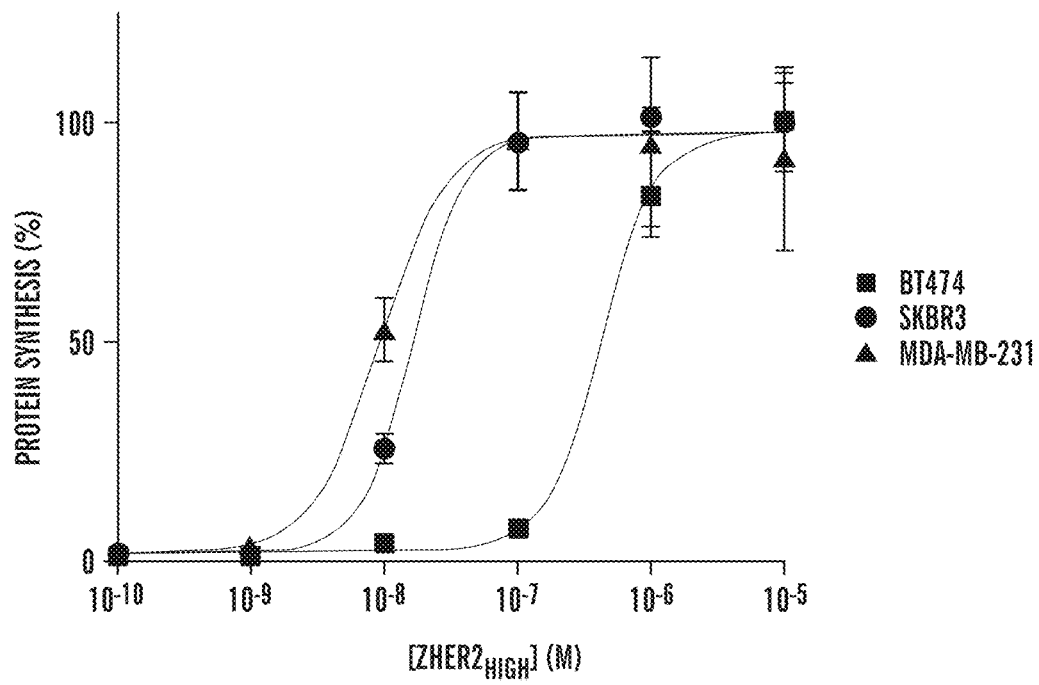
FIGS. 8A-8B show competition by high- and low-affinity ZHER2 Affibodies for mPA-ZHER2-dependent killing. Cells were exposed to a lethal dose of mPA-ZHER2 and LFN-DTA in the presence of increasing amounts of a high ($Z_{HER2:342}$, FIG. 8A) or lower ($Z_{HER2:4}$, FIG. 8B) affinity HER2 Affibody for 4 h, and the incorporation of [$^3$H]-leucine was measured and graphed as described in FIG. 7. High, moderate, and low HER2 expressing cell lines are shown in square, circle, and triangle, respectively. Each point on the curves represents the average of four experiments.
Figure 8B:
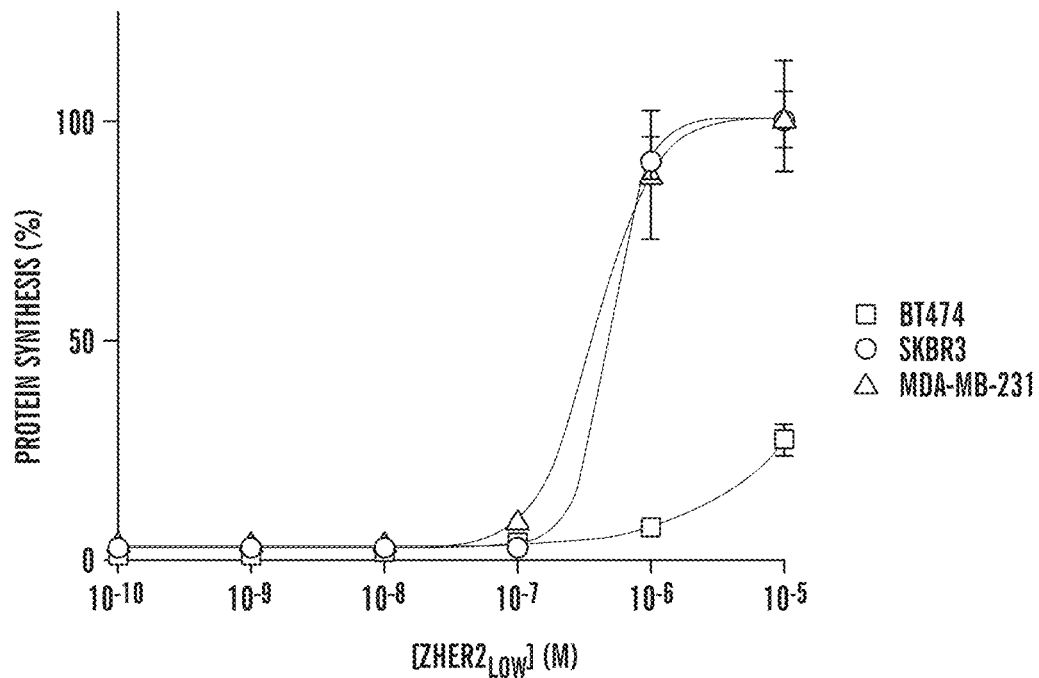

Free $Z_{HER2:342}$ affibody competitively inhibited mPA-ZHER2-dependent killing of HER2-positive cells (FIG. 8). BT474 cells expressing high levels of HER2 required a higher level of free Affibody ($EC_{50}$~400 nM) for toxin blockage relative to cell lines expressing low or moderate levels of HER2 ($EC_{50}$~20 nM) (FIG. 8A). A lower-affinity Affibody ($Z_{HER2:4}$) (Wikman et al. 2004) was less effective in blocking toxin action than the higher-affinity $Z_{HER2:342}$ Affibody (FIG. 8B).

Bafilomycin A1 protected A431 cells from $LF_N$-DTA-dependent killing mediated by either mPA-ZHER2 or mPA-EGF, indicating that translocation of effectors by mPA variants was dependent on the endosomal pH, as is the case with wild-type PA.

mPA-ZHER2 can Deliver Multiple Cytocidal Effectors

Figure 9A:
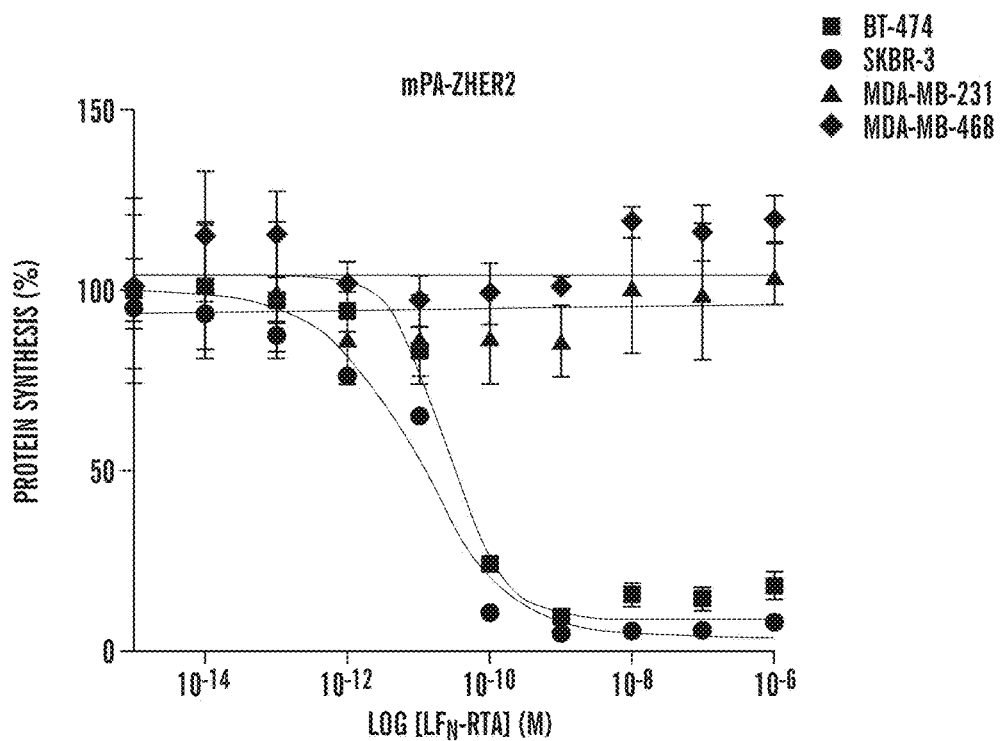
FIGS. 9A-9B show mPA-ZHER2- and mPA-EGF-directed killing of cell lines by $LF_N$-RTA. Cells were exposed to mPA-ZHER2 (FIG. 9A) or mPA-EGF (FIG. 9B) in combination with LFN-RTA, at the indicated concentrations for 4 h, and the level of protein synthesis was measured by scintillation counting. Cells expressing high, moderate, low, or no detectable levels of HER2 (epidermal growth factor 2) or EGFR (epidermal growth factor 1, or HER1) are indicated with square, circle, triangle and diamond in FIG. 9A; and square, circle, triangle and diamond in FIG. 9B, respectively.
Figure 9B:
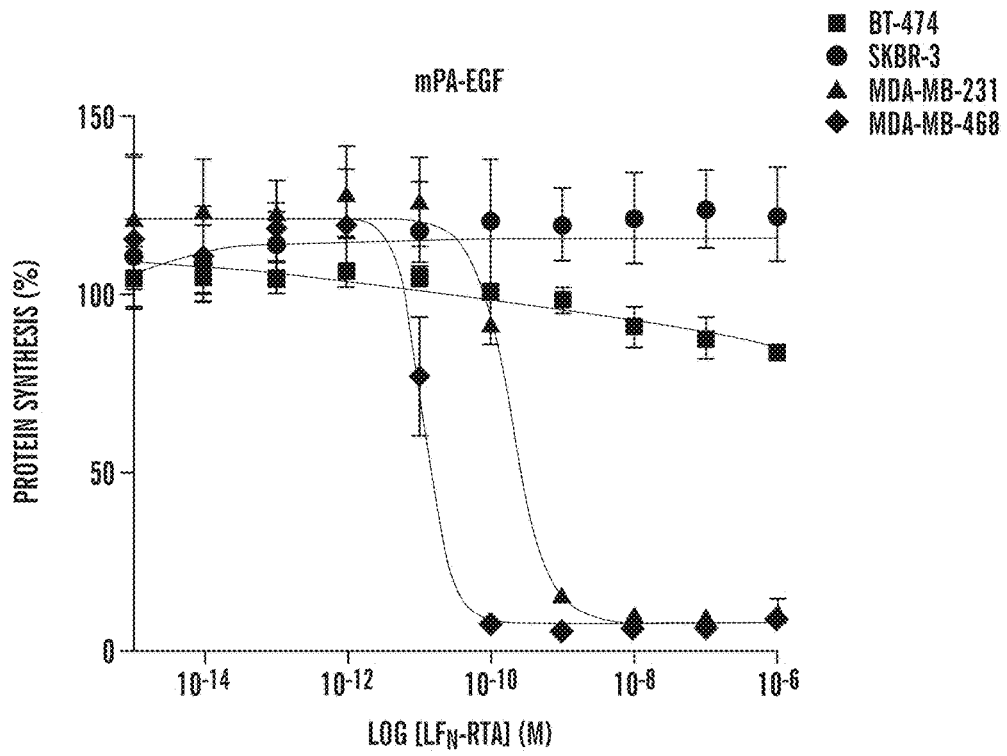

We tested an analog of $LF_N$-DTA in which DTA was replaced with the catalytic domain of ricin (RTA). RTA inhibits protein synthesis by a different biochemical mechanism than DTA, namely by depurinating a crucial adenosine residue in the 28S rRNA of the eukaryotic ribosome (Endo & Tsurugi 1987). $LF_N$-RTA combined with mPA-ZHER2 (FIG. 3A) or mPA-EGF (FIG. 9B) killed HER2-positive or EGFR-positive cells, respectively. Generally $LF_N$-RTA was 10-100 fold less efficient than $LF_N$-DTA in killing the cell lines tested. An exception was the SKBR-3 cell line, in which the $EC_{50}$ values for $LF_N$-RTA or $LF_N$-DTA combined with mPA-ZHER2 were about the same (compare FIG. 7A and FIG. 9A). Because SKBR-3 lacks detectable levels of EGF receptor, it was resistant to mPA-EGF-mediated killing.

HER2-Targeted Anthrax Toxin Kills a Trastuzumab-Resistant Tumor Cell Line

Figure 10A:
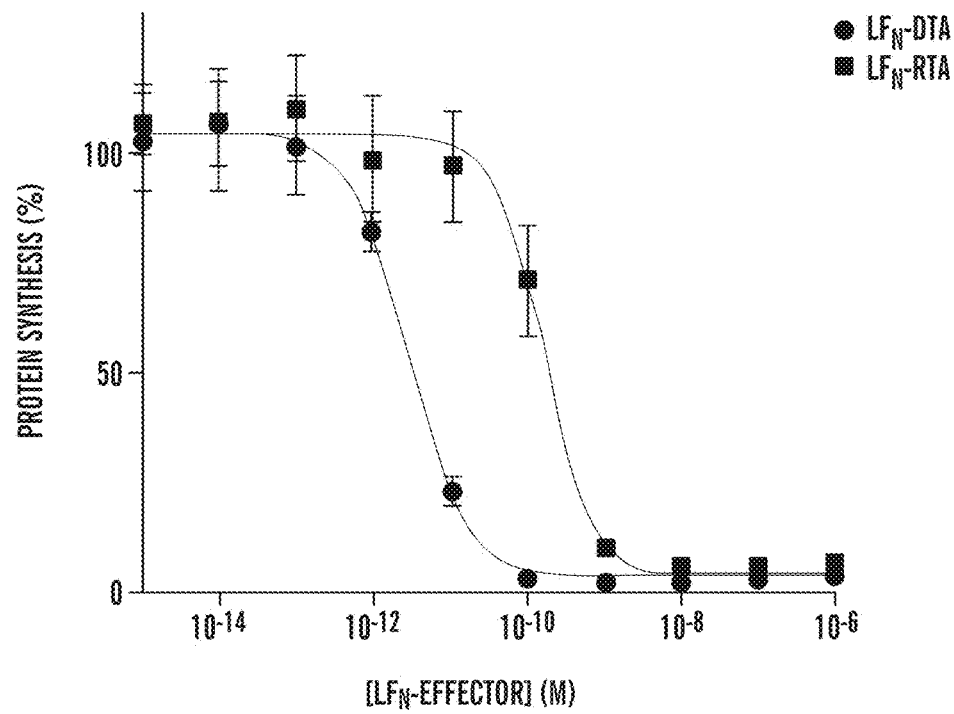
FIGS. 10A-10D show killing of a HER2-positive, trastuzumab-resistant tumor cell line by mPA-ZHER2 plus $LF_N$-DTA or $LF_N$-RTA.
Figure 10B:
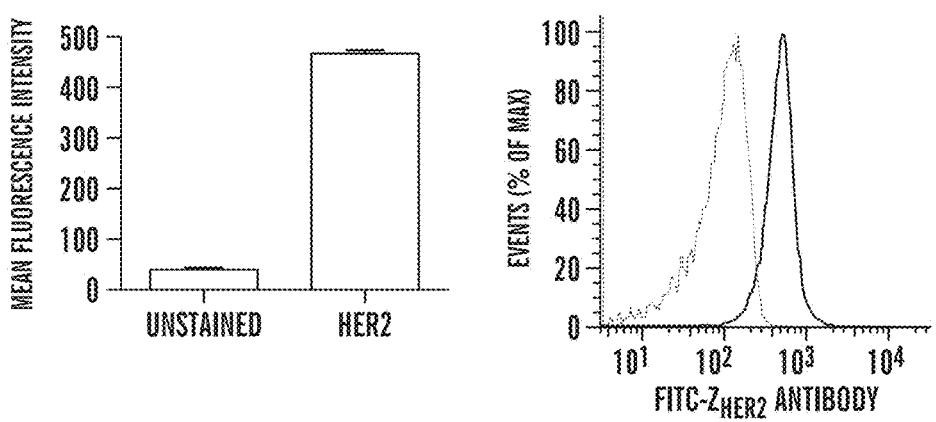
Figure 10C:
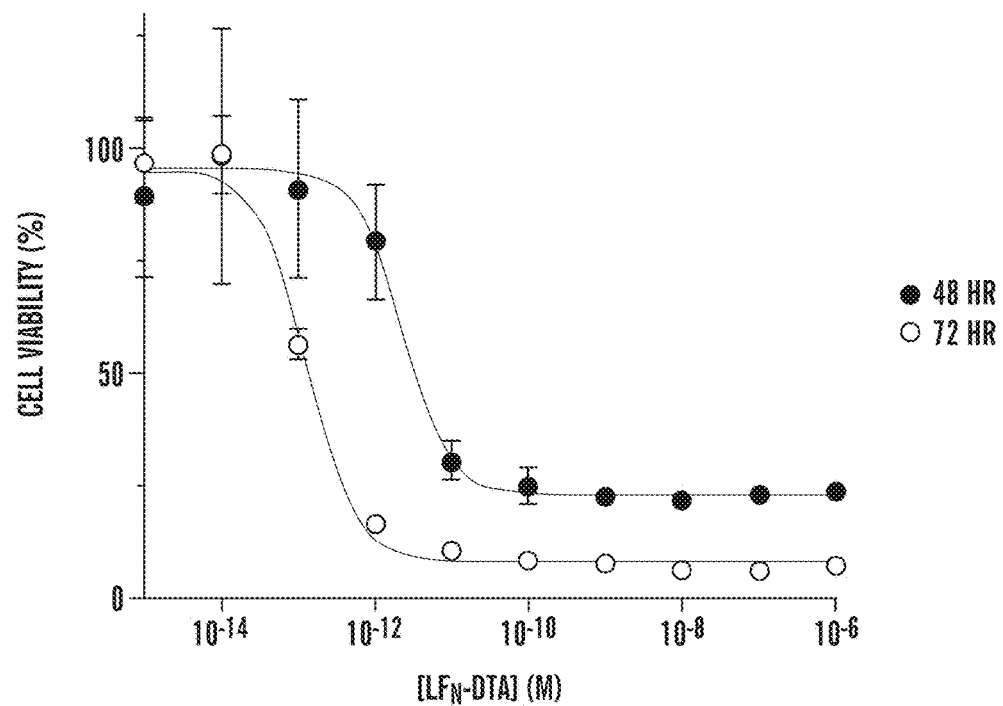
Figure 10D:
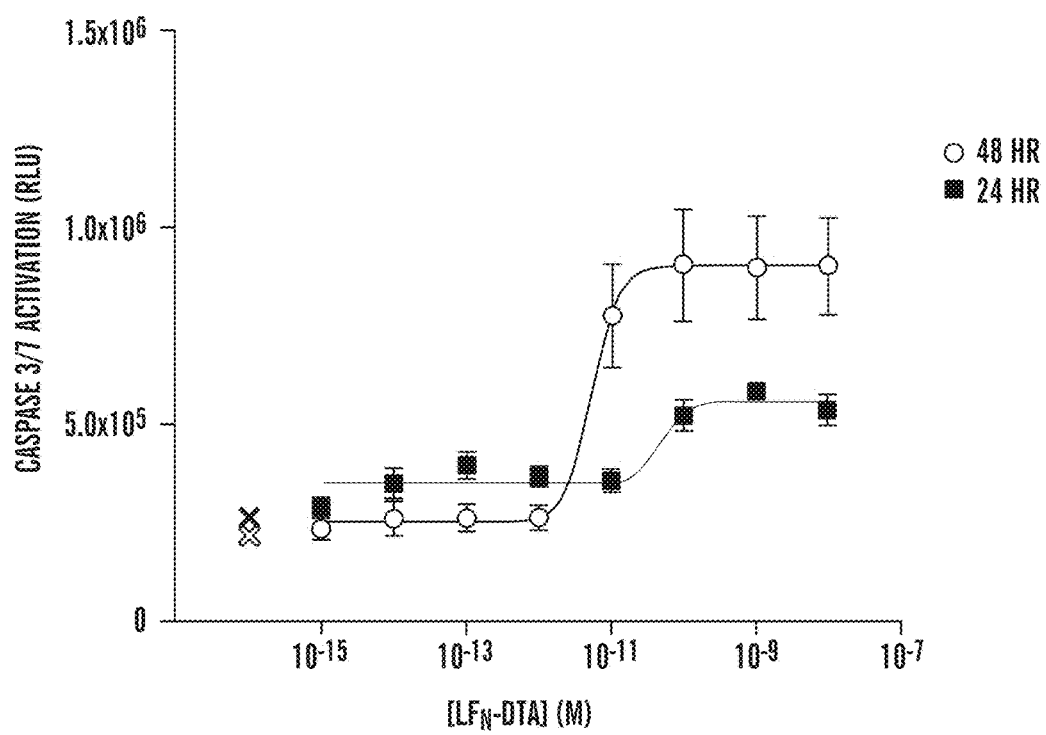

The FDA-approved monoclonal antibody trastuzumab has been effective in prolonging HER2-positive patient survival, but not all patients respond, and a large percentage develop therapeutic resistance over time (Arteaga et al. 2012). The JIMT-1 cell line recently isolated from a patient that had HER2 amplification and clinically resistant to trastuzumab (Tanner et al. 2004). As in other HER2-positive cell lines we tested, protein synthesis in JIMT-1 cells was inhibited in response to mPA-ZHER2 and $LF_N$-DTA, resulting in cell death by apoptosis (FIG. 10). The level of sensitivity was consistent with the HER2 level, and killing mediated by $LF_N$-RTA was less efficient than by $LF_N$-DTA (FIG. 10A). JIMT-1 cells required a longer duration of toxin exposure (additional 24 h) to achieve similar cell killing and caspase 3/7 activation, compared to other HER2-positive cell lines (FIGS. 10C and 10D).

Figure 11A:
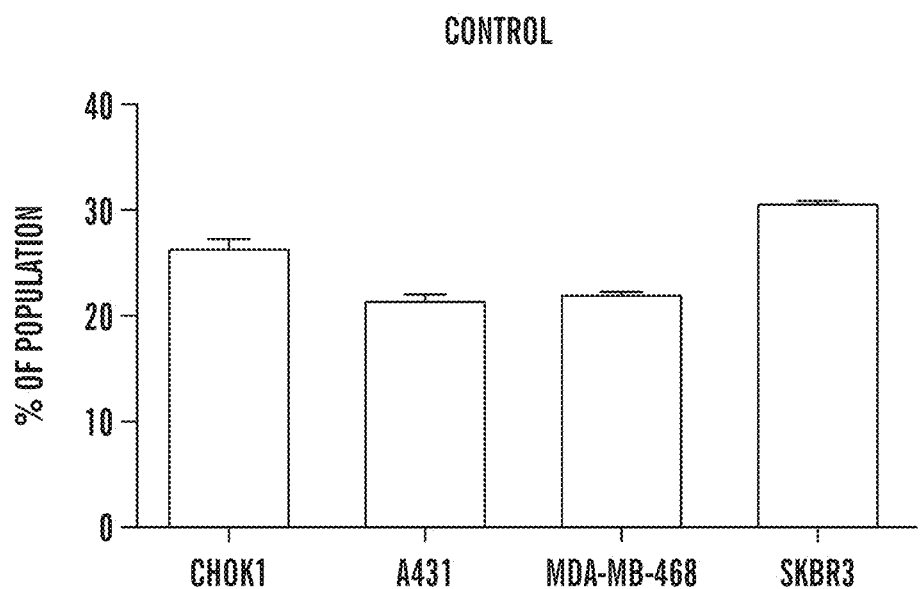
FIGS. 11A-11B shows that mPA-ZHER2 mediates specific killing of HER2-positive cells in a heterogeneous population. Fluorescent cells shown to be sensitive to the actions of mPA-ZHER2 and $LF_N$-DTA ($A431^{CFP}$ and $SKBR3^{RFP}$) were mixed equally with resistant cells (CHO-K1 and MDA-MB-468$^{GFP}$) and incubated with mPA-ZHER2 plus $LF_N$-DTA or with mPA plus $LF_N$-DTA (control; the control FACS data are identical to those in FIGS. 7C and 8A, as all of the experiments were conducted simultaneously). After 24 h, cells were detached with trypsin and quantified by FACS or washed with PBS and imaged with a fluorescence microscope (microscope slide FACS color photos not included). Each bar represents the average of experiments performed in triplicate. Control is shown in FIG. 11A and exposure to the re-directed fusion toxin is shown in FIG. 11B.
Figure 11B:
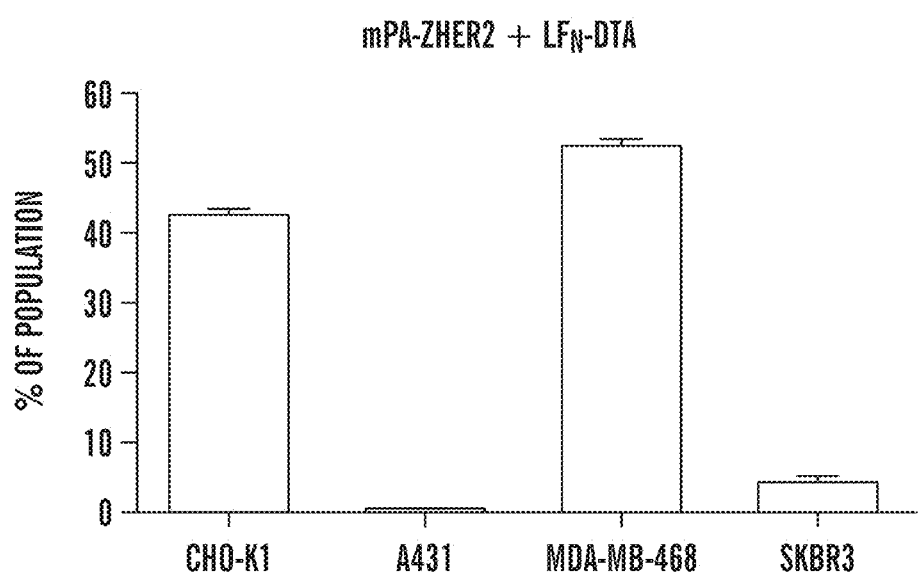

No Bystander Effect was Seen in Mixtures of HER2 Positive and HER2-Negative Cells To test for a possible bystander effect, we evaluated the specificity of mPA-ZHER2 in mixtures of HER2-positive and HER2-negative cells. First, to allow individual cell types to be distinguished by fluorescence microscopy or FACS, we labeled selected cell lines by transduction with puromycin-selectable lentiviruses encoding fluorescent proteins with distinguishable emission properties. Equal numbers of cells from each of 4 cell lines (2 HER2-positive and 2 HER2-negative lines) were mixed, and the resulting mixture was incubated 24 h with mPA-ZHER2 plus $LF_N$-DTA. Flow cytometry revealed that the HER2-negative cells, CHO-K1 (unlabeled) and MDA-MB-468$^{GFP}$ (green), now comprised almost the entire population; the HER2-positive A431$^{CFP}$ (cyan) and SKBR3$^{RFP}$ (red) cells had been reduced from ~50% to less than 5% of the total (FIG. 11A). Fluorescence microscopy of adherent cells gave comparable results (FIG. 11B). Because the small remaining population of SKBR-3 cells (~4%) appeared to be dead by microscopy, we believe that flow cytometry may have overestimated this population because of an inherently long half-life of the fluorescent protein used for labeling. Thus, the mPA-ZHER2/$LF_N$-DTA combination was able to kill the HER2-positive cells in a mixed cell population, with no evident bystander effect on HER2-negative cells.

Figure 12:
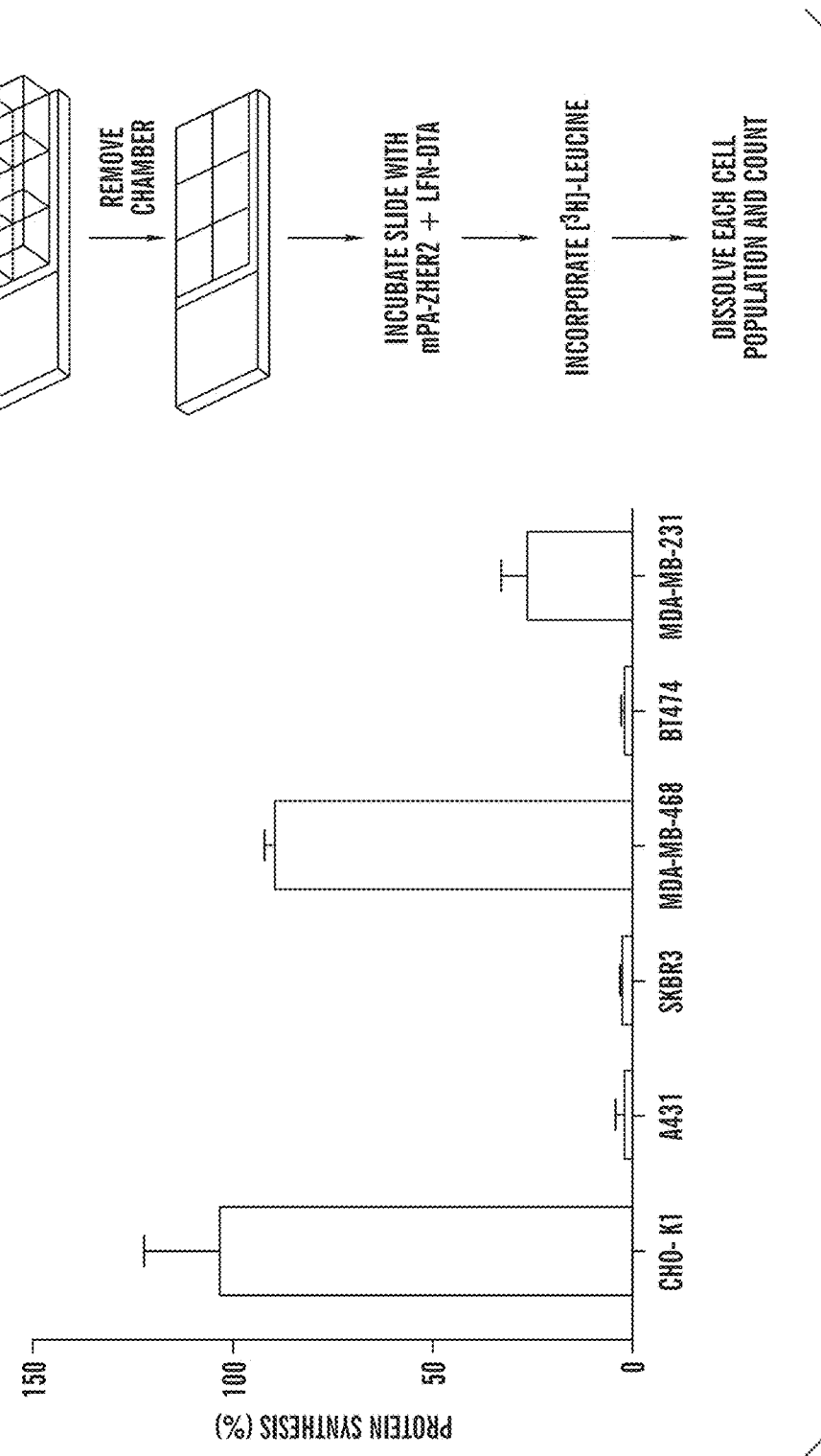
FIG. 12 shows that mPA-ZHER2-mediated killing in a heterogeneous cell population. Tumor cells were plated in separate compartments of a chambered slide (right panel) and incubated at 37° C. The following day, the chambers were removed, and the slide was incubated with mPA-ZHER2 plus $LF_N$-DTA. After 4 h, cells were incubated with medium supplemented with [$^3$H]-leucine for 1 h and dissolved in 6 M guanidine-HCl, and the incorporated radiolabel was quantified by scintillation counting. Percent protein synthesis was normalized against cells treated with mPA+$LF_N$-DTA.

We also used another approach to test for bystander effects. Multiple cell lines were grown in separate wells of a chambered slide (FIG. 12). The partitioning element was removed from the slide, and the slide, containing all cell lines, was then incubated in medium containing mPA-ZHER2 and $LF_N$-DTA. After a 4-hour incubation, the slide was washed and transferred to medium supplemented with [$^3$H]-leucine. After a further 1-hour incubation, the cells were washed, individual cell populations were dissolved with 6M guanidine-HCl, and the incorporated radioactive leucine was quantified by scintillation counting. FIG. 6 shows that cells expressing high and moderate levels of HER2 were killed, MDA-MB-231 cells with low HER2 expression maintained limited resistance, and cells lacking HER2 (CHO-K1 and MDA-MB-468) were unaffected.

Figure 13A:
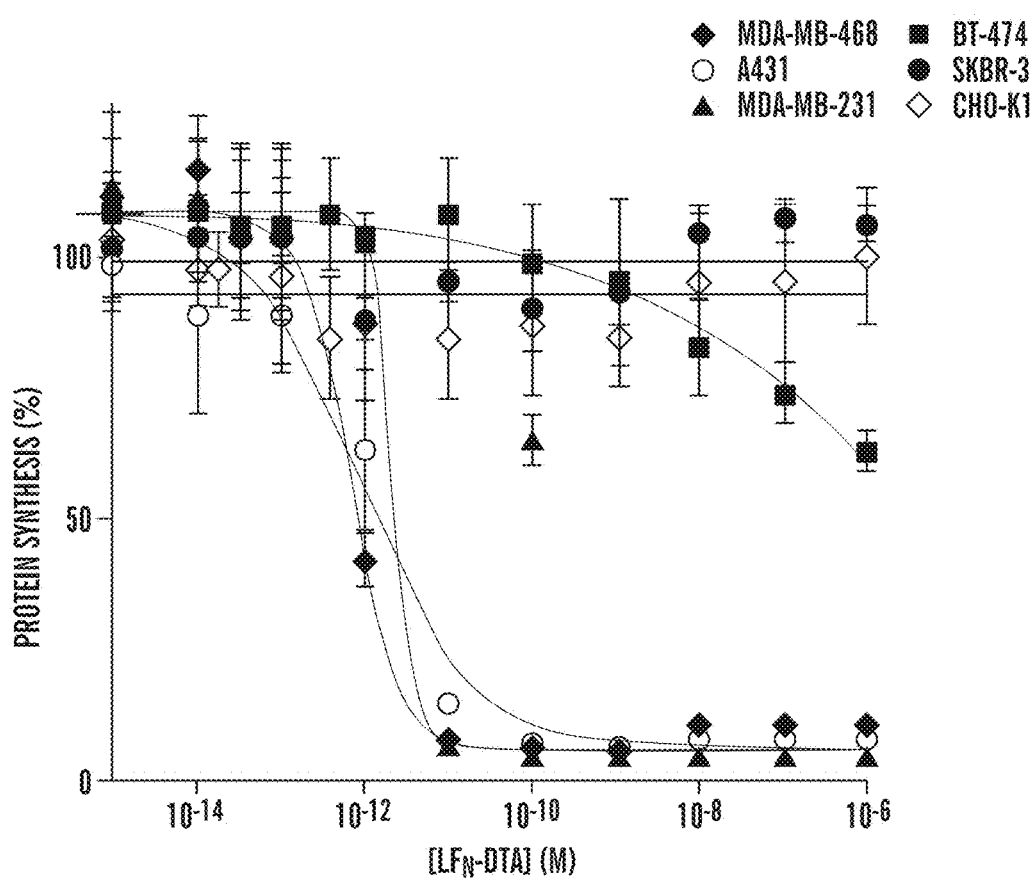
FIGS. 13A-13C show that mPA-EGF specifically kills EGF-expressing cells in a heterogeneous population.
Figure 13B:
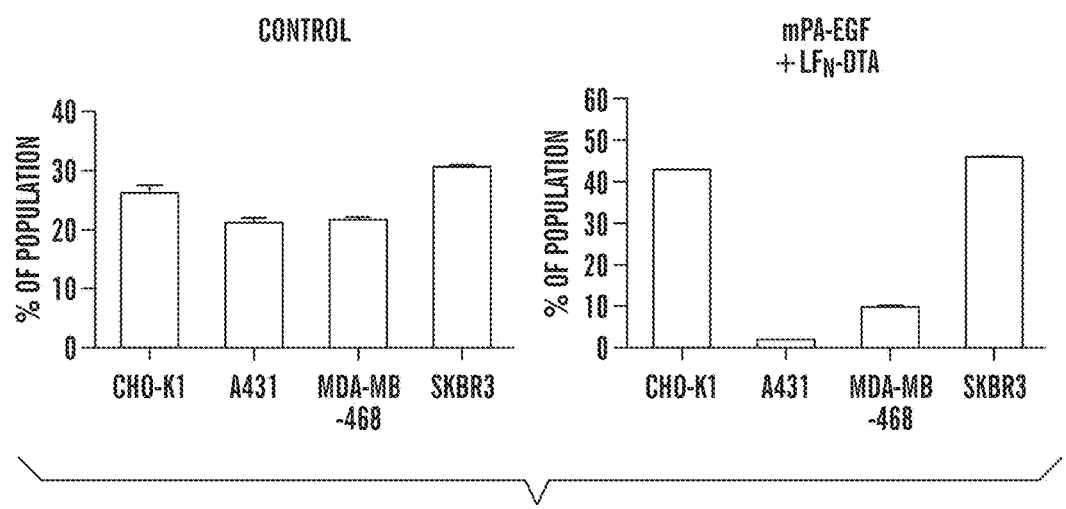
Figure 13C:
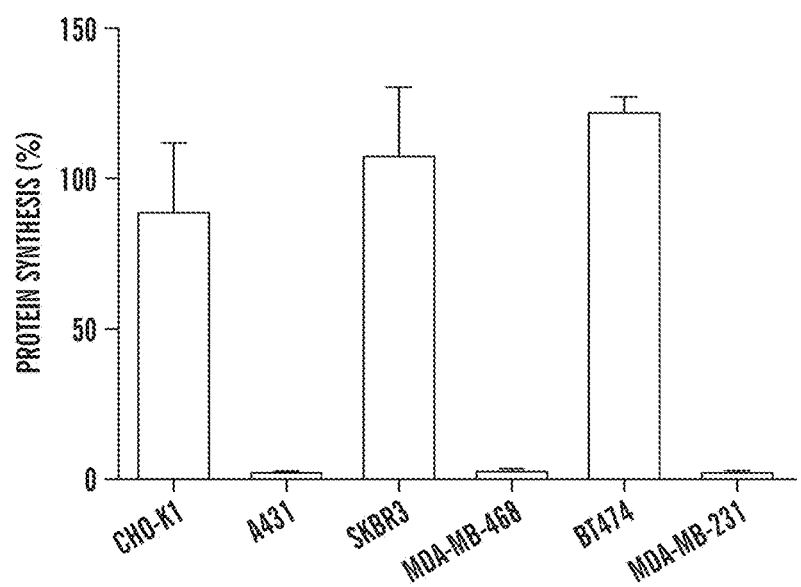

Mixing mPA-ZHER2 and mPA-EGF Allowed Killing of Both HER2- and EGFR Positive Cells in a Heterogeneous Cell Population Like mPA-HER2, mPA-EGF in combination with $LF_N$-DTA was able to kill cognate cell lines (EGFR-positive in this case) in both homogeneous (FIG. 13A) and heterogeneous cell populations, with no effects on cells lacking the EGF receptor (FIG. 13). Killing a mixed population of fluorescent cells by mPA-EGF presented the same caveats as those described for mPA-ZHER2, where a small population of EGFR-positive cells (MDA-MB-468, colored green) remained (FIGS. 13B and 13C). Once again, a more sensitive' assay measuring protein synthesis by incorporation of radioactive leucine showed that EGFR-positive cells were killed, and cells with very low or no EGFR expression survived (FIG. 13D).

Figure 14A:
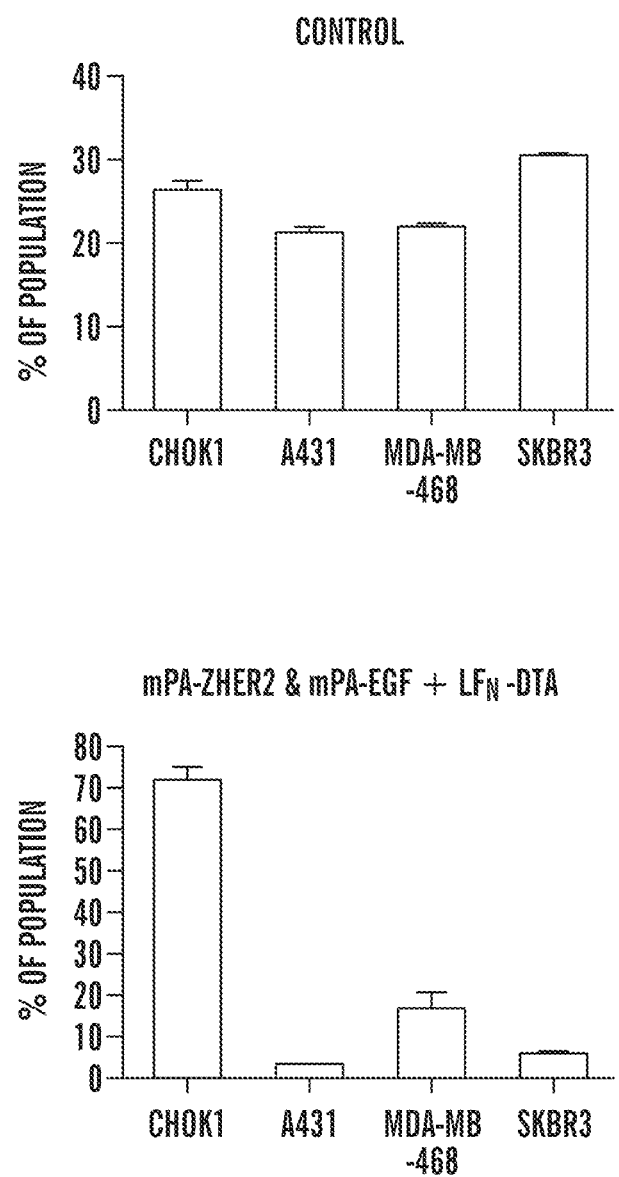
FIGS. 14A-14B show that re-directed mPA variants act together to eliminate heterogeneous tumor cell populations.
Figure 14B:
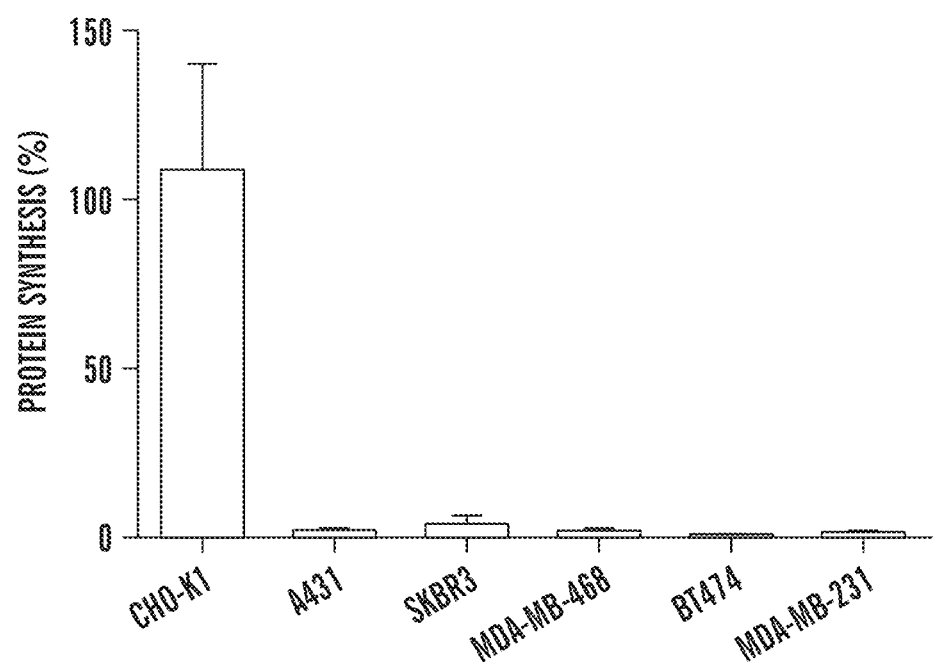

We also tested the ability of a mixture of mPA-ZHER2 and mPA-EGF to target specific receptor-bearing cells in a mixed population of cancer cells. As shown in FIG. 14, the combination of mPA-ZHER2 and mPA-EGF was able to kill both HER2-positive and EGFR-positive cells in the presence of $LF_N$-DTA, while CHO-K1 cells, which do not express either receptor, remained unaffected.

Quantification of HER2 and EGFR Levels on Cell Lines

Cells ($10^5$) were incubated with either a FITC-conjugated HER2- or EGFR-specific Affibody and analyzed by FACS. (Left panels). The mean fluorescence intensity for 50,000 events was calculated in FlowJo and plotted in the GRAPHPAD PRISM® software package. Histograms (not shown) of the raw data displayed the shift in fluorescence compared to unstained cells for EGF and HER2 receptors in CHOK1, A431, BT474, MDA-MB-231, MDA-MB-468, SKBR-3 cells.

Delivery of LFN-DTA Causes Cell Death by Apoptosis

Apoptosis was measured by caspase 3/7 activation, after exposing various cell lines (MDA-MB-231, MDA-MB-468, and CHOK1) to mPA-ZHER2 and LFN-DTA, at concentrations $10^{15}$ M, $10^{-13}$ M, $10^{-11}$ M, $10^{-9}$ M, $10^{-7}$ M for 24 h. Relative light units (RLU) generated by caspase 3/7 activation and cleavage of a pre-luminescent substrate are plotted against LFN-DTA concentration. Each data point represented the average of 4 experiments. Control cells exposed to mPA-ZHER2 alone. Data not shown.

Entry of Effectors Mediated by Wild-Type and Redirected mPA Variants is Dependent on Endosomal pH A431 cells ($3 \times 10^5$) were exposed to $LF_N$-DTA (1 nM) and either mPA-ZHER2, mPA-EGF, or WT PA (20 nM) in the absence or presence of bafilomycin A at concentrations $10^{-11}$ M, $10^{-10}$ M, $10^{-9}$ M, $10^{-8}$ M, $10^{-7}$ M. After 4-hours, cells were washed with PBS and incubated with medium containing [$^3$H]-leucine. After 1-hour, the level of protein synthesis was measured by scintillation counting. Percent protein synthesis was normalized against cells treated with the mPA variant alone and plotted using the GRAPHPAD PRISM software package. Each point on the curves represented the average of four experiments. Data not shown. The level of cell surface HER2, EGFR, and ANTRX1/2 were quantified on A431 cells using either anti-HER2 or EGFR affibodies or FITC-labeled PA. Data not shown.

Discussion

Cell-surface markers on aggressive forms of certain cancers have been an important focus of efforts to develop targeted anticancer therapies. A prominent example is the monoclonal anti-HER2 antibody trastuzumab, which is effective in slowing tumor growth and prolonging patient survival (Vogel et al. 2002). However, most patients develop resistance to this antibody over time due to its ineffectiveness in eliminating tumors (Arteaga et al. 2012). Antibody therapies have been combined with conventional chemotherapy or radiation to circumvent such resistance, and antibody-drug conjugates (ADC's), which kill cells through the action of a linked cytotoxic small molecule compound ("payload"), have recently emerged as an alternative mode of targeted therapy (Carter & Senter 2008).

Modifying intracellularly acting toxins to direct their actions to tumor cells represents an attractive approach to targeted therapy, in part because the catalytic mode of action of the effector moieties renders these toxins so potent. Replacing the native receptor-binding domain of toxins such as DT or *Pseudomonas* exotoxin A (ETA) with a heterologous receptor-binding protein has been employed effectively to target the cytocidal actions of these toxins (Pastan et al. 2007). This line of investigation has led to a licensed treatment for cutaneous T-cell lymphomas, termed denileukin diftitox (trade name, ONTAK®) (Foss 2000; Williams et al. 1987), and other targeted protein toxins are currently under investigation (Madhumathi J & Verma 2012). ONTAK is a fusion protein created by replacing the receptor-binding domain of DT with interleukin-2 (IL-2). The IL-2 moiety binds the fusion toxin to high-affinity IL-2 receptors on tumor cells, and the catalytic moiety of DT (DTA) is transported to the cytosol, where it blocks protein synthesis and causes cell death (Collier & Cole 1969; Collier 1967).

Elucidation of the structure and activities of anthrax toxin in recent years has led to experiments to explore its potential as a platform for developing anticancer chemotherapeutics.

In one study the furin site of PA was mutated to prevent activation of the protein, and the native receptor binding activity of the modified PA was exploited to inhibit vascular endothelial growth factor-induced and basic fibroblast growth factor-induced angiogenesis (Rogers et al. 2007). In other studies lethal factor combined with native PA was found to induce apoptosis in human melanoma cells, suggesting possible applications for this and other cancers in which disease progression is due in part to constitutive activation of MAPK signaling (Duesbery et al. 2001; Koo et al. 2002). One approach to targeting PA has been to replace its furin cleavage site with a site selective for a different protease—metalloproteinase or urokinase plasminogen activator—that is overexpressed on the surface of cancer cells (Abi-Habib et al. 2006; Liu et al. 2000).

In the current work we changed the receptor recognition specificity of PA as an approach to using the protein as a vehicle for introducing cytotoxic effectors specifically into HER2-positive cells. mPA-ZHER2 proved to be a highly selective mediator of the entry of $LF_N$-DTA and $LF_N$-RTA into HER2-positive cells. The EC50 of LFN-DTA showed an inverse relationship to the level of HER2 on the cell lines tested (FIG. 7). Why LFN-RTA was 10- to 100-fold less potent than LFN-DTA (FIG. 9) is unclear, but may be related to differences in stability of the effectors in the cytosol, the kinetics of inactivation of target molecules, or any of a number of other factors.

The specificity of mPA-ZHER2 for cells bearing the HER2 receptor was shown by competition assays (FIG. 8) and by its ability to target only HER2-positive tumor cells in a mixed cell population (FIGS. 12 and 11). No off-target effects were observed when HER2-negative cells were mixed with HER2-positive cells before treatment with $LF_N$-DTA plus mPA-ZHER2. The affinity of monomeric ZHER2 Affibody for the HER2 marker rivals that of the best antibodies (~20 pM) (Orlova et al. 2006), and the natural oligomerization properties of mPA-ZHER2 presumably increase the avidity of the interaction of the complex for the HER2 receptor on cells. Once oligomerization takes place, the avidity for the receptor would be such that effectively no dissociation of toxic complexes from cells would occur.

The entry of the cytocidal effectors mediated by either mPA-ZHER2 or mPA-EGF was pH-dependent, as is the case for wild-type PA. The difference in the inhibitory concentration of BFA for the different PA variants is likely due to their respective receptor abundance where EGFR>ANTXR1/2>HER2. Alternatively the pH threshold of PA pore formation may vary for the three receptors, as the pH threshold of WT PA bound to ANTXR1 is a full unit higher than when it is bound to ANTXR2, which has higher affinity (Lacy et al. 2004; Rainey et al. 2005).

A HER2-positive, trastuzumab-resistant tumor cell line (JIMT-1) was also susceptible to toxin action (FIG. 10). The JIMT-1 cell line, isolated from a patient clinically-resistant to trastuzumab, displays properties thought to be associated with the development of HER2-targeted antibody resistance, including low expression of HER2 (despite gene amplification), receptor masking by other cell surface proteins (an event which can mask up to 80% of the trastuzumab binding sites), low PTEN expression, activation of the PIK3CA gene, and high expression of neuregulin-1 (NRG-1) (Tanner et al. 2004; Nagy et al. 2005; Koninki et al. 2010). The EC50 in relation to HER2 level was consistent with our data on trastuzumab-sensitive HER2-positive cell lines. $LF_N$-RTA was also effective in killing JIMT-1 cells, but higher concentrations than $LF_N$-DTA were needed (FIG. 4A). The delivery of $LF_N$-DTA, into the cytosol of JIMT-1 cells, led to apoptotic cell death, as assessed by an XTT cytotoxicity assay and caspase 3/7 activation (FIGS. 10C and 10D). The redirected toxin was able to kill most cells (>75%) after 48 h and achieved almost complete elimination (~95%) after 72 h (FIG. 10C). The greater exposure required to achieve complete cell killing could have resulted from any of a number of differences that increased the time to reach caspase 3/7 activation (48 h versus 24 h; FIG. 10D).

The elimination of a trastuzumab-resistant cell line by anthrax toxin represents potential advantage over current antibody therapies. Some ADC's have been shown to kill trastuzumab-resistant tumor cell lines (such as JIMT-1), but are significantly less effective than $LF_N$-DTA plus mPA-ZHER2, and require high doses (μg/ml versus pg/ml) to achieve moderate killing (~25% cell death) (Lewis Phillips et al. 2008; Koninki et al. 2010). This difference in potency (~5000 fold) could result from efficient delivery of a cytocidal enzyme into the cytosol, reflecting the strength of the interaction between mPA-ZHER2 and the HER2 receptor, as well as the catalytic inactivation of the cytosolic substrate. The accessibility of the mPA-ZHER2 binding site on the surface of JIMT-1 cells compared to the antibody binding site, estimated to be 20% available, could also be a factor (Nagy et al. 2005).

Because tumors are composed of a heterogeneous population of cells that have different receptor expression levels, it is unlikely that any single anti-cancer therapy can achieve complete tumor elimination. Combinations of small molecules, antibodies, and radiation have been used with some success. The binary nature of anthrax toxin and the ability of mPA to oligomerize also suggests that one may be able to combine mPA-ZHER2 with other forms of mPA targeted to different overexpressed surface tumor markers to eliminate heterogeneous populations of cells. Consistent with this notion, as mPA-ZHER2 and mPA-EGF, in combination with $LF_N$-DTA completely eliminated a panel of tumor cells with different HER2 and EGF receptor expression levels (FIG. 14).

The ability of mPA-ZHER2 to act cooperatively with an analogous mPA-variant targeting a different tumor marker highlights the adaptability of targeting with mPA. In addition to combining mPA variants, the ability of the PA pore to translocate any of a variety of intracellular effector enzymes allows the possibility of using combinations of effectors that kill by different biochemical mechanisms. The enzymatic destruction of targeted cells from within by multiple effectors should minimize the likelihood of resistant escape mutants arising, a universal problem in chemotherapy.

Our in vitro data indicate that the targeting of the HER2 receptor by modified, receptor-targeted anthrax toxin is specific and potent, and displays no off-target toxicity towards HER2-negative cell lines. The susceptibility of a HER2-positive trastuzumab-resistant tumor cell line to toxin action highlights a significant potential advantage of our system over current FDA-approved antibody therapies. For these reasons and the advantages described above, the PA-based targeting of distinct populations of cancer cells represents a promising therapeutic strategy for cancer treatment.

Table 1 below shows in vitro activity of mPA-ZHER2 and $LF_N$-DTA against various cancer cell lines:

| | Cell line EC$_{50}$ (M) | | | | | | |
|---|---|---|---|---|---|---|---|
| Assay | BT-474 | JIMT-1 | SKBR-3 | A431 | MDA-MB-231 | MDA-MB-468 | CHO-K1 |
| Protein Synthesis Inhibition[a] | $9.4 \times 10^{-14}$ | $3.0 \times 10^{-12}$ | $1.3 \times 10^{-11}$ | $1.5 \times 10^{-11}$ | $7.0 \times 10^{-9}$ | $>1 \times 10^{-6}$ | $>1 \times 10^{-6}$ |
| Cell Viability[b] | $8.0 \times 10^{-14}$ | $2.5 \times 10^{-12}$ | $1.6 \times 10^{-12}$ | $4.1 \times 10^{-11}$ | $1.3 \times 10^{-9}$ | $>1 \times 10^{-6}$ | $>1 \times 10^{-6}$ |
| Apoptosis[c] | $7.2 \times 10^{-13}$ | $5.1 \times 10^{-11}$ | ND | $1.6 \times 10^{-11}$ | $1.1 \times 10^{-9}$ | $>1 \times 10^{-6}$ | $>1 \times 10^{-6}$ |

[a]Measured by [3H]-leucine incorporation after 4 hr toxin exposure
[b]Measured by XIT cell viability assay after 48 hr toxin exposure
[c]Measured by caspase 3/7 activation after 24 hr toxin exposure We have also shown that the system works with cytocidal effector proteins, e.g., LF$_N$ fused to the catalytic domain of ricin, and demonstrated the killing of a Herceptin resistant cell line, JIMT-1, using the system as described. For example, killing by an alternative cytocidal LFN-fusion (LFN fused to the catalytic domain of ricin; LFN-RTA) is demonstrated in FIGS. 9A and B. Killing of a Herceptin-resistant cell line is shown, e.g, in FIGS. 10A-D.

REFERENCES

Abi-Habib, R. J. et al., 2006. A urokinase-activated recombinant anthrax toxin is selectively cytotoxic to many human tumor cell types. Molecular Cancer Therapeutics, 5(10), pp. 2556-2562.

Arteaga, C. L. et al., 2012. Treatment of HER2-positive breast cancer: current status and future perspectives. Nature reviews. Clinical oncology, 9(1), pp. 16-32.

Berchuck, A. et al., 1990. Overexpression of HER-2/neu is associated with poor survival in advanced epithelial ovarian cancer. Cancer Research, 50(13), pp. 4087-4091.

Bradley, K. A. et al., 2001. Identification of the cellular receptor for anthrax toxin. Nature, 414(6860), pp. 225-229.

Carter, P. J. & Senter, P. D., 2008. Antibody-drug conjugates for cancer therapy. Cancer journal (Sudbury, Mass.), 14(3), pp. 154-169.

Collier, R. J., 1967. Effect of diphtheria toxin on protein synthesis: inactivation of one of the transfer factors. Journal of Molecular Biology, 25(1), pp. 83-98.

Collier, R. J., 2009. Membrane translocation by anthrax toxin. Molecular Aspects of Medicine, 30(6), pp. 413-422.

Collier, R. J. & Cole, H. A., 1969. Diphtheria toxin subunit active in vitro. Science, 164(884), pp. 1179-1181.

Cunningham, K. et al., 2002. Mapping the lethal factor and edema factor binding sites on oligomeric anthrax protective antigen. Proceedings of the National Academy of Sciences of the United States of America, 99(10), pp. 7049-7053.

Duesbery, N. S. et al., 1998. Proteolytic inactivation of MAP-kinase-kinase by anthrax lethal factor. Science, 280(5364), pp. 734-737.

Duesbery, N. S. et al., 2001. Suppression of ras-mediated transformation and inhibition of tumor growth and angiogenesis by anthrax lethal factor, a proteolytic inhibitor of multiple MEK pathways. Proceedings of the National Academy of Sciences of the United States of America, 98(7), pp. 4089-4094.

Endo, Y. & Tsurugi, K., 1987. RNA N-glycosidase activity of ricin A-chain. Mechanism of action of the toxic lectin ricin on eukaryotic ribosomes. The Journal of biological chemistry, 262(17), pp. 8128-8130.

Foss, F. M., 2000. DAB(389)IL-2 (denileukin diftitox, ONTAK): a new fusion protein technology. Clinical lymphoma, 1 Suppl 1, pp. S27-31.

Gravalos, C. & Jimeno, A., 2008. HER2 in gastric cancer: a new prognostic factor and a novel therapeutic target. Annals of oncology: official journal of the European Society for Medical Oncology/ESMO, 19(9), pp. 1523-1529.

Honjo, T., Nishizuka, Y. & Hayaishi, O., 1968. Diphtheria toxin-dependent adenosine diphosphate ribosylation of aminoacyl transferase II and inhibition of protein synthesis. The Journal of biological chemistry, 243(12), pp. 3553-3555.

Kintzer, A. F. et al., 2009. The Protective Antigen Component of Anthrax Toxin Forms Functional Octameric Complexes. Journal of Molecular Biology, 392(3), pp. 614-629.

Klimpel, K. R. et al., 1992. Anthrax toxin protective antigen is activated by a cell surface protease with the sequence specificity and catalytic properties of furin. Proceedings of the National Academy of Sciences of the United States of America, 89(21), pp. 10277-10281.

Koo, H.-M. et al., 2002. Apoptosis and melanogenesis in human melanoma cells induced by anthrax lethal factor inactivation of mitogen-activated protein kinase kinase. Proceedings of the National Academy of Sciences of the United States of America, 99(5), pp. 3052-3057.

Koninki, K. et al., 2010. Multiple molecular mechanisms underlying trastuzumab and lapatinib resistance in JIMT-1 breast cancer cells. Cancer letters, 294(2), pp. 211-219.

Lacy, D. B. et al., 2004. Structure of heptameric protective antigen bound to an anthrax toxin receptor: a role for receptor in pH-dependent pore formation. Proceedings of the National Academy of Sciences of the United States of America, 101(36), pp. 13147-13151.

Leppla, S. H., 1982. Anthrax toxin edema factor: a bacterial adenylate cyclase that increases cyclic AMP concentrations of eukaryotic cells. Proceedings of the National Academy of Sciences of the United States of America, 79(10), pp. 3162-3166.

Lewis Phillips, G. D. et al., 2008. Targeting HER2-positive breast cancer with trastuzumab-DMI, an antibody-cytotoxic drug conjugate. Cancer Research, 68(22), pp. 9280-9290.

Liu, S. et al., 2000. Tumor cell-selective cytotoxicity of matrix metalloproteinase-activated anthrax toxin. Cancer Research, 60(21), pp. 6061-6067.

Löfblom, J. et al., 2010. Affibody molecules: engineered proteins for therapeutic, diagnostic and biotechnological applications. FEBS Letters, 584(12), pp. 2670-2680.

Madhumathi J & Verma, R. S., 2012. Therapeutic targets and recent advances in protein immunotoxins. Current Opinion in Microbiology.

Mechaly, A., McCluskey, A. J. & Collier, R. J., 2012. Changing the Receptor Specificity of Anthrax Toxin. mBio, 3(3), pp. e00088-12. Available at: http://mbio.asm.org/content/3/3/e00088-12.

Miller, C. J., Elliott, J. L. & Collier, R. J., 1999. Anthrax Protective Antigen: Prepore-to-Pore Conversion t. Biochemistry, 38(32), pp. 10432-10441.

Milne, J. C. et al., 1994. Anthrax protective antigen forms oligomers during intoxication of mammalian cells. The Journal of biological chemistry, 269(32), pp. 20607-20612.

Mogridge, J. et al., 2002. The lethal and edema factors of anthrax toxin bind only to oligomeric forms of the protective antigen. Proceedings of the National Academy of Sciences of the United States of America, 99(10), pp. 7045-7048.

Nagy, P. et al., 2005. Decreased accessibility and lack of activation of ErbB2 in JIMT-1, a herceptin-resistant, MUC4-expressing breast cancer cell line. Cancer Research, 65(2), pp. 473-482.

Nord, K. et al., 1997. Binding proteins selected from combinatorial libraries of an alpha-helical bacterial receptor domain. Nature Biotechnology, 15(8), pp. 772-777.

Orlova, A. et al., 2006. Tumor imaging using a picomolar affinity HER2 binding affibody molecule. Cancer Research, 66(8), pp. 4339-4348.

Pastan, I. et al., 2007. Immunotoxin treatment of cancer. Annual review of medicine, 58, pp. 221-237.

Rainey, G. J. A. et al.; 2005. Receptor-specific requirements for anthrax toxin delivery into cells. Proceedings of the National Academy of Sciences of the United States of America, 102(37), pp. 13278-13283.

Rogers, M. S. et al., 2007. Mutant Anthrax Toxin B Moiety (Protective Antigen) Inhibits Angiogenesis and Tumor Growth. Cancer Research, 67(20), pp. 9980-9985.

Scobie, H. M., 2003. Human capillary morphogenesis protein 2 functions as an anthrax toxin receptor. Proceedings of the National Academy of Sciences, 100(9), pp. 5170-5174.

Slamon, D. J. et al., 1989. Studies of the HER-2/neu proto-oncogene in human breast and ovarian cancer. Science, 244(4905), pp. 707-712.

Tanner, M. et al., 2004. Characterization of a novel cell line established from a patient with Herceptin-resistant breast cancer. Molecular Cancer Therapeutics, 3(12), pp. 1585-1592.

Vitale, G. et al., 1998. Anthrax lethal factor cleaves the N-terminus of MAPKKs and induces tyrosine/threonine phosphorylation of MAPKs in cultured macrophages. Biochemical and Biophysical Research Communications, 248(3), pp. 706-711.

Vogel, C. L. et al., 2002. Efficacy and safety of trastuzumab as a single agent in first-line treatment of HER2-overexpressing metastatic breast cancer. Journal of clinical oncology: official journal of the American Society of Clinical Oncology, 20(3), pp. 719-726.

Wikman, M. et al., 2004. Selection and characterization of HER2/neu-binding affibody ligands. Protein engineering, design & selection: PEDS, 17(5), pp. 455-462.

Williams, D. P. et al., 1987. Diphtheria toxin receptor binding domain substitution with interleukin-2: genetic construction and properties of a diphtheria toxin-related interleukin-2 fusion protein. Protein engineering, 1(6), pp. 493-498.

Young, J. A. T. & Collier, R. J., 2007. Anthrax Toxin: Receptor Binding, Internalization, Pore Formation, and Translocation. Annual Review of Biochemistry, 76(1), pp. 243-265.

We claim:

1. An altered binary toxin system for delivery of a therapeutic protein to a target cell comprising:
    a fusion protein comprising a receptor-ablated pore-forming AB toxin unit fused to a non-toxin-associated receptor-binding ligand specific for the target cell, wherein the receptor-ablated pore-forming AB toxin unit comprises an anthrax toxin protective antigen (PA) with a domain 4 mutation that ablates receptor binding; and
    a complementary toxin unit comprising anthrax toxin lethal factor (LF) or the amino terminal portion of anthrax toxin lethal factor ($LF_N$).

2. The altered binary toxin system of claim 1, wherein the PA is $PA^{N682AD683A}$.

3. The altered binary toxin system of claim 1, wherein the non-toxin associated receptor-binding ligand specific for the target cell is an epidermal growth factor-1 or epidermal growth factor 2.

4. The altered binary toxin system of claim 1, wherein the therapeutic protein is the catalytic domain of diphtheria toxin (DTA), ricin, shiga toxin, or *pseudomonas* exotoxin A.

5. The altered binary toxin system of claim 1, wherein the non-toxin-associated receptor-binding ligand specific for the target cell binds to a receptor selected from epidermal growth factor receptors HER1, HER2, HER3 or HER4; vascular endothelial growth factor receptors VEGFR-1, VEGFR-2 or VEGFR-3; insulin-like growth factor 1 receptor; fibroblast growth factor receptors; thrombospondin 1 receptor; estrogen receptors; urokinase receptors; progesterone receptors; testosterone receptors; carcinoembryonic antigens; prostate-specific antigens; farnesoid X receptors; transforming growth factor receptors; transferrin receptors; hepatocyte growth factor receptors; or vasoactive intestinal polypeptide receptors 1 and 2.

6. The altered binary toxin system of claim 1, wherein the non-toxin-associated receptor-binding ligand specific for the target cell is selected from an antibody or an affibody.

7. The altered binary toxin system of claim 6, wherein the affibody is a HER2 affibody.

8. The altered binary toxin system of claim 7, wherein the HER2 affibody is ZHER2.

9. The altered binary toxin system of claim 1, wherein the therapeutic protein is the cytotoxic domain of shiga toxin, shiga-like toxin 1 and 2, ricin, ricin toxin A chain, abrin, gelonin, pokeweed antiviral protein, saporin, trichsanthin, pepcin, maize RIP, alpha-sarcin, *Clostridium perfringens* epsilon toxin, *Botulinum* neurotoxins, *Staphylococcus* enterotoxins, *Clostridium difficile* toxins, pertussis toxins, or *pseudomonas* exotoxin.

10. A kit for delivering bioactive molecules to a eukaryotic cell, comprising an altered binary toxin system of claim 1 and a pharmaceutically acceptable carrier.

11. A method for treating cancer comprising administering to a subject diagnosed with cancer the altered binary toxin system of claim 1.

12. The method of claim 11, wherein the altered binary toxin system comprises a receptor-redirected anthrax protective antigen.

13. The method of claim 12, wherein the cancer is a HER2 positive cancer and the anthrax protective antigen is fused with a HER2 binding ligand.

14. The method of claim 13, wherein the HER2 binding ligand is an antibody or an affibody.

* * * * *

SEQUENCE LISTING

```
<160> NUMBER OF SEQ ID NOS: 17

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Pro Gly His Lys Thr Gln Pro
1               5

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gatttagtaa ttcgaattca agtacgg                                              27

<210> SEQ ID NO 3
<211> LENGTH: 32
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 3
cattcagagt cgctgtttgg ttgcgtttta tg                                     32

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gttttatgcc ccggagatcc tatctcatag cc                                     32

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cataaaacgc aaccaaacag cgactatgaa tg                                     32

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggtggtgctc gagtcaacgg agctcccacc atttc                                  35

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggctatgaga taggatctcc ggggcataaa ac                                     32

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtggtggtgg tggtgctcga gtcagctttt gatttc                                 36

<210> SEQ ID NO 9
<211> LENGTH: 764
<212> TYPE: PRT
<213> ORGANISM: Bacillus anthracis
```

<400> SEQUENCE: 9

```
Met Lys Lys Arg Lys Val Leu Ile Pro Leu Met Ala Leu Ser Thr Ile
1               5                   10                  15
Leu Val Ser Ser Thr Gly Asn Leu Glu Val Ile Gln Ala Glu Val Lys
            20                  25                  30
Gln Glu Asn Arg Leu Leu Asn Glu Ser Glu Ser Ser Gln Gly Leu
        35                  40                  45
Leu Gly Tyr Tyr Phe Ser Asp Leu Asn Phe Gln Ala Pro Met Val Val
    50                  55                  60
Thr Ser Ser Thr Thr Gly Asp Leu Ser Ile Pro Ser Ser Glu Leu Glu
65                  70                  75                  80
Asn Ile Pro Ser Glu Asn Gln Tyr Phe Gln Ser Ala Ile Trp Ser Gly
                85                  90                  95
Phe Ile Lys Val Lys Lys Ser Asp Glu Tyr Thr Phe Ala Thr Ser Ala
            100                 105                 110
Asp Asn His Val Thr Met Trp Val Asp Asp Gln Glu Val Ile Asn Lys
        115                 120                 125
Ala Ser Asn Ser Asn Lys Ile Arg Leu Glu Lys Gly Arg Leu Tyr Gln
130                 135                 140
Ile Lys Ile Gln Tyr Gln Arg Glu Asn Pro Thr Glu Lys Gly Leu Asp
145                 150                 155                 160
Phe Lys Leu Tyr Trp Thr Asp Ser Gln Asn Lys Lys Glu Val Ile Ser
                165                 170                 175
Ser Asp Asn Leu Gln Leu Pro Glu Leu Lys Gln Lys Ser Ser Asn Ser
            180                 185                 190
Arg Lys Lys Arg Ser Thr Ser Ala Gly Pro Thr Val Pro Asp Arg Asp
        195                 200                 205
Asn Asp Gly Ile Pro Asp Ser Leu Glu Val Glu Gly Tyr Thr Val Asp
210                 215                 220
Val Lys Asn Lys Arg Thr Phe Leu Ser Pro Trp Ile Ser Asn Ile His
225                 230                 235                 240
Glu Lys Lys Gly Leu Thr Lys Tyr Lys Ser Ser Pro Glu Lys Trp Ser
                245                 250                 255
Thr Ala Ser Asp Pro Tyr Ser Asp Phe Glu Lys Val Thr Gly Arg Ile
            260                 265                 270
Asp Lys Asn Val Ser Pro Glu Ala Arg His Pro Leu Val Ala Ala Tyr
        275                 280                 285
Pro Ile Val His Val Asp Met Glu Asn Ile Ile Leu Ser Lys Asn Glu
290                 295                 300
Asp Gln Ser Thr Gln Asn Thr Asp Ser Gln Thr Arg Thr Ile Ser Lys
305                 310                 315                 320
Asn Thr Ser Thr Ser Arg Thr His Thr Ser Glu Val His Gly Asn Ala
                325                 330                 335
Glu Val His Ala Ser Phe Phe Asp Ile Gly Gly Ser Val Ser Ala Gly
            340                 345                 350
Phe Ser Asn Ser Asn Ser Ser Thr Val Ala Ile Asp His Ser Leu Ser
        355                 360                 365
Leu Ala Gly Glu Arg Thr Trp Ala Glu Thr Met Gly Leu Asn Thr Ala
370                 375                 380
Asp Thr Ala Arg Leu Asn Ala Asn Ile Arg Tyr Val Asn Thr Gly Thr
385                 390                 395                 400
Ala Pro Ile Tyr Asn Val Leu Pro Thr Thr Ser Leu Val Leu Gly Lys
                405                 410                 415
```

```
Asn Gln Thr Leu Ala Thr Ile Lys Ala Lys Glu Asn Gln Leu Ser Gln
                420                 425                 430

Ile Leu Ala Pro Asn Asn Tyr Tyr Pro Ser Lys Asn Leu Ala Pro Ile
            435                 440                 445

Ala Leu Asn Ala Gln Asp Asp Phe Ser Ser Thr Pro Ile Thr Met Asn
450                 455                 460

Tyr Asn Gln Phe Leu Glu Leu Glu Lys Thr Lys Gln Leu Arg Leu Asp
465                 470                 475                 480

Thr Asp Gln Val Tyr Gly Asn Ile Ala Thr Tyr Asn Phe Glu Asn Gly
                485                 490                 495

Arg Val Arg Val Asp Thr Gly Ser Asn Trp Ser Glu Val Leu Pro Gln
            500                 505                 510

Ile Gln Glu Thr Thr Ala Arg Ile Ile Phe Asn Gly Lys Asp Leu Asn
        515                 520                 525

Leu Val Glu Arg Arg Ile Ala Ala Val Asn Pro Ser Asp Pro Leu Glu
    530                 535                 540

Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
                565                 570                 575

Thr Glu Phe Asp Phe Asn Phe Asp Gln Gln Thr Ser Gln Asn Ile Lys
            580                 585                 590

Asn Gln Leu Ala Glu Leu Asn Ala Thr Asn Ile Tyr Thr Val Leu Asp
        595                 600                 605

Lys Ile Lys Leu Asn Ala Lys Met Asn Ile Leu Ile Arg Asp Lys Arg
    610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
                645                 650                 655

Leu Leu Asn Ile Asp Lys Asp Ile Arg Lys Ile Leu Ser Gly Tyr Ile
            660                 665                 670

Val Glu Ile Glu Asp Thr Glu Gly Leu Lys Glu Val Ile Asn Asp Arg
        675                 680                 685

Tyr Asp Met Leu Asn Ile Ser Ser Leu Arg Gln Asp Gly Lys Thr Phe
    690                 695                 700

Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
                725                 730                 735

Ile Asn Pro Ser Glu Asn Gly Asp Thr Ser Thr Asn Gly Ile Lys Lys
            740                 745                 750

Ile Leu Ile Phe Ser Lys Lys Gly Tyr Glu Ile Gly
        755                 760

<210> SEQ ID NO 10
<211> LENGTH: 735
<212> TYPE: PRT
<213> ORGANISM: Bacillus anthracis

<400> SEQUENCE: 10

Glu Val Lys Gln Glu Asn Arg Leu Leu Asn Glu Ser Glu Ser Ser Ser
1               5                   10                  15

Gln Gly Leu Leu Gly Tyr Tyr Phe Ser Asp Leu Asn Phe Gln Ala Pro
            20                  25                  30
```

```
Met Val Val Thr Ser Ser Thr Thr Gly Asp Leu Ser Ile Pro Ser Ser
             35                  40                  45

Glu Leu Glu Asn Ile Pro Ser Glu Asn Gln Tyr Phe Gln Ser Ala Ile
 50                  55                  60

Trp Ser Gly Phe Ile Lys Val Lys Lys Ser Asp Glu Tyr Thr Phe Ala
 65                  70                  75                  80

Thr Ser Ala Asp Asn His Val Thr Met Trp Val Asp Asp Gln Glu Val
                 85                  90                  95

Ile Asn Lys Ala Ser Asn Ser Asn Lys Ile Arg Leu Glu Lys Gly Arg
                100                 105                 110

Leu Tyr Gln Ile Lys Ile Gln Tyr Gln Arg Glu Asn Pro Thr Glu Lys
            115                 120                 125

Gly Leu Asp Phe Lys Leu Tyr Trp Thr Asp Ser Gln Asn Lys Lys Glu
            130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
                180                 185                 190

Thr Val Asp Val Lys Asn Lys Arg Thr Phe Leu Ser Pro Trp Ile Ser
            195                 200                 205

Asn Ile His Glu Lys Lys Gly Leu Thr Lys Tyr Lys Ser Ser Pro Glu
            210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
                260                 265                 270

Lys Asn Glu Asp Gln Ser Thr Gln Asn Thr Asp Ser Gln Thr Arg Thr
            275                 280                 285

Ile Ser Lys Asn Thr Ser Thr Ser Arg Thr His Thr Ser Glu Val His
            290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
            340                 345                 350

Asn Thr Ala Asp Thr Ala Arg Leu Asn Ala Asn Ile Arg Tyr Val Asn
            355                 360                 365

Thr Gly Thr Ala Pro Ile Tyr Asn Val Leu Pro Thr Thr Ser Leu Val
            370                 375                 380

Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
                405                 410                 415

Ala Pro Ile Ala Leu Asn Ala Gln Asp Asp Phe Ser Ser Thr Pro Ile
                420                 425                 430

Thr Met Asn Tyr Asn Gln Phe Leu Glu Leu Glu Lys Thr Lys Gln Leu
            435                 440                 445
```

-continued

```
Arg Leu Asp Thr Asp Gln Val Tyr Gly Asn Ile Ala Thr Tyr Asn Phe
    450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
        515                 520                 525

Ile Ala Phe Gly Phe Asn Glu Pro Asn Gly Asn Leu Gln Tyr Gln Gly
    530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
                565                 570                 575

Val Leu Asp Lys Ile Lys Leu Asn Ala Lys Met Asn Ile Leu Ile Arg
            580                 585                 590

Asp Lys Arg Phe His Tyr Asp Arg Asn Asn Ile Ala Val Gly Ala Asp
        595                 600                 605

Glu Ser Val Val Lys Glu Ala His Arg Glu Val Ile Asn Ser Ser Thr
    610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
                645                 650                 655

Asn Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
        675                 680                 685

Ile Ser Asn Pro Asn Tyr Lys Val Asn Val Tyr Ala Val Thr Lys Glu
    690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                725                 730                 735

<210> SEQ ID NO 11
<211> LENGTH: 58
<212> TYPE: PRT
<213> ORGANISM: Staphylococcus aureus

<400> SEQUENCE: 11

Val Asp Asn Lys Phe Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
                20                  25                  30

Ser Leu Tyr Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 12
<211> LENGTH: 58
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (9)..(11)
<223> OTHER INFORMATION: Any amino acid
<220> FEATURE:
<221> NAME/KEY: MOD_RES
<222> LOCATION: (13)..(14)
<223> OTHER INFORMATION: Any amino acid
<220> FEATURE:
<221> NAME/KEY: MOD_RES
<222> LOCATION: (17)..(18)
<223> OTHER INFORMATION: Any amino acid
<220> FEATURE:
<221> NAME/KEY: MOD_RES
<222> LOCATION: (24)..(25)
<223> OTHER INFORMATION: Any amino acid
<220> FEATURE:
<221> NAME/KEY: MOD_RES
<222> LOCATION: (27)..(28)
<223> OTHER INFORMATION: Any amino acid
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (35)..(35)
<223> OTHER INFORMATION: Any amino acid

<400> SEQUENCE: 12

Val Asp Asn Lys Phe Asp Lys Glu Xaa Xaa Xaa Ala Xaa Xaa Glu Ile
1               5                   10                  15

Xaa Xaa Leu Pro Asn Leu Asn Xaa Xaa Gln Xaa Xaa Ala Phe Ile Xaa
            20                  25                  30

Ser Leu Xaa Asp Asp Pro Ser Gln Ser Ala Asp Leu Leu Ala Glu Ala
        35                  40                  45

Lys Lys Leu Asp Asp Ala Gln Ala Pro Lys
    50                  55

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcgggcggtc atggtgatgt aggt                                      24

<210> SEQ ID NO 14
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aattgggtat tgtttgggga atatactacc ccgttgatct tgaagttctt ccaa     54

<210> SEQ ID NO 15
<211> LENGTH: 54
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 15
ttggaagaac ttaaagatca acggggtagt atattcccca aacaataccc aatt          54

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctattaaaac tgtgacgatg gtggaggtgc                                      30

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 17

His His His His His His
1               5
```